US007473783B2

(12) United States Patent
Bounaud et al.

(10) Patent No.: US 7,473,783 B2
(45) Date of Patent: Jan. 6, 2009

(54) BICYCLIC PYRAZOLO PROTEIN KINASE MODULATORS

(75) Inventors: Pierre-Yves Bounaud, San Diego, CA (US); Andrew Vaino, San Diego, CA (US)

(73) Assignee: SGX Pharmaceuticals, Inc., San Diego, CA (US)

( * ) Notice: Subject to any disclaimer, the term of this patent is extended or adjusted under 35 U.S.C. 154(b) by 638 days.

(21) Appl. No.: 11/016,126

(22) Filed: Dec. 17, 2004

(65) Prior Publication Data

US 2005/0176786 A1 Aug. 11, 2005

Related U.S. Application Data

(60) Provisional application No. 60/530,111, filed on Dec. 17, 2003, provisional application No. 60/598,221, filed on Aug. 2, 2004.

(51) Int. Cl.
*C07D 513/00* (2006.01)
*A61K 31/425* (2006.01)
(52) U.S. Cl. ...................................... 548/153; 514/367
(58) Field of Classification Search ................. 548/153; 514/367
See application file for complete search history.

(56) References Cited

U.S. PATENT DOCUMENTS 6,566,363 B2   5/2003   Chong et al.

FOREIGN PATENT DOCUMENTS

| DE | 2429195 A1 | 2/1976 |
|---|---|---|
| JP | 07244361 A2 | 9/1995 |
| JP | 2003327860 A2 | 11/2003 |
| JP | 7-244361 A | 9/2005 |
| WO | WO/9808486 A2 | 3/1998 |
| WO | WO01/81348 A1 | 11/2001 |
| WO | WO/0212250 A2 | 2/2002 |
| WO | WO 02/12250 * | 12/2002 |
| WO | WO03/101989 A1 | 12/2003 |

OTHER PUBLICATIONS

Chande et al. Indian Journal of Chemistry, Section B: Organic Chemistry Including Medicinal Chemistry (1995), 34B(11), 985-989.*
Elnagdi et al. Journal of Heterocyclic Chemistry (1979), 16(1), 61-4.*
Chande, Madhukar S., et al. "A facile synthesis of novel nitrogen-sulphur heterocycles containing the amidino moiety and their antimicrobial activity-part 1", *Indian Journal of Chemistry, Section B: Organic Chemistry Including Medicinal Chemistry*, (2004) 43(B)2:378-384.
Chande, Madhukar S., et al. "New synthetic methods. Par 1. Regioselective 1,2-transposition of a carbonyl group in carbocyclic and heterocyclic ketones", *Indian Journal of Chemistry, Section B: Organic Chemistry Including Medicinal Chemistry*, (2003) 42B(10)2:2625-2627.
Giorgi, Gianluca, et al. "Mass spectrometric characterization of substituted 2-thiazolin-4-one derivatives", *Journal of Mass Spectrometry*, (2002) 37(7):709-715.
Kassab, Rafika Ramadan, (CAPLUS 1997).
Al-Mousawi, Saleh M., et al. "Studies with condensed azines: new routes to pyrazolo[3,4-b]pyridines and pyrrolo[3,2-b]pyridines", *Journal of Chemical Research, Synopses*, (1997) 9:318-319.
Ismail, M.M., et al. "Quinolones substituted by different moieties. III. Reactions of 1,2-dihydro-4-hydroxy-1-methyl-2-oxoquinoline-3 carboxaldehyde with some cyclic active methylene compounds", *Chemical Papers* (1997) 51(1):43-47.
Chande, Madhukar S., et al. 2-Alkyl/arylimono-5-carbethoxythiazolidin-4-ones: a new synthon for the synthesis of spiro and fused ring heterocycles. Part 1., *Indian Journal of Chemistry, Section B: Organic Chemistry Including Medicinal Chemistry* (1996), 35B(4):373-6.
Chande, Madhukar S., et al. "Synthesis of pyrazolothiazole and pyrimididiothiazole derivatives", *Indian Journal of Chemistry, Section B: Organic Chemistry Including Medicinal Chemistry* (1995), 34B(11):985-9.
Singh, R.V. K., et al. "Antimicrobial and antiamebic activity of some new thiazolidino-pyrazolines", *Journal of the Institution of Chemists* (India), (1992) 64(2):55-8.
Singh, R.V.K., et al. "Synthesis of some newer 2-phenyliminothiazolidinopyrazolines", *Journal of the Indian Chemical Society* (1991) 68(3):167-8.
Pawar, R.A., et al. "Studies on the Vilsmeier-Haack reaction. A versatile new synthesis of 4-chloro-2-phenylaminothiazole-5-carboxaldelhyde and related fused heterocyclic compounds and heterocyclic Schiff's bases", *Indian Journal of Chemistry, Section B: Organic Chemistry Including Medicinal Chemistry* (1989), 28B(10):866-7.
Hafez, Ebtisam Abdel Aziz, et al. "A new convenient synthesis of 1,6-diaryl-2-thioxoperhydor-4-pyrimidinones: reaction of 3-phenyl-2-propenoyl isothiocyanate with aromatic and heteroaromatic amines", *Liebigs Annalen der Chemie* (1987) 1:65-7.
Elnagdi, Mohamed Hilmy, et al. "Reactions with cyclic amidines. II. The behavior of cyclic amidines toward ethoxycarbonyl and aroyl isothiocyanates", *Journal of Heterocyclic Chemistry* (1979) 16(1):61-4.
Gakhar, H.K., et al. "Pyrazolothiazoles", *Journal of the Indian Chemcial Society* (1974) 51(11):941-943.
Patent Abstracts of Japan, vol. 1996, No. 1, Jan. 31, 1996.

* cited by examiner

*Primary Examiner*—D. Margaret Seaman
*Assistant Examiner*—Nizal S Chandrakumar
(74) *Attorney, Agent, or Firm*—Wilson Sonsini Goodrich & Rosati

(57) ABSTRACT

The present invention provides novel bicyclic pyrazolo kinase modulators and methods of using the novel bicyclic pyrazolo kinase modulators to treat diseases mediated by kinase activity.

27 Claims, No Drawings

SEQUENCE LISTING

```
<160> NUMBER OF SEQ ID NOS: 22

<210> SEQ ID NO 1
<211> LENGTH: 28
<212> TYPE: DNA
<213> ORGANISM: Artificial Sequence
<220> FEATURE:
<223> OTHER INFORMATION: Forward primer

<400> SEQUENCE: 1
cacaagtaca aaaagcaatt taggtatg                                           28

<210> SEQ ID NO 2
<211> LENGTH: 18
<212> TYPE: DNA
<213> ORGANISM: Artificial Sequence
<220> FEATURE:
<223> OTHER INFORMATION: Reverse primer

<400> SEQUENCE: 2
ccgaatcttc gacctgag                                                      18

<210> SEQ ID NO 3
<211> LENGTH: 26
<212> TYPE: DNA
<213> ORGANISM: Artificial Sequence
<220> FEATURE:
<223> OTHER INFORMATION: Gene sequence after ligation into vector

<400> SEQUENCE: 3
aagggcatca tcaccatcac cactga                                             26

<210> SEQ ID NO 4
<211> LENGTH: 24
<212> TYPE: DNA
<213> ORGANISM: Artificial Sequence
<220> FEATURE:
<223> OTHER INFORMATION: Forward primer

<400> SEQUENCE: 4
tcaaaaaaga ggcagtgggc tttg                                               24

<210> SEQ ID NO 5
<211> LENGTH: 21
<212> TYPE: DNA
<213> ORGANISM: Artificial Sequence
<220> FEATURE:
<223> OTHER INFORMATION: Reverse primer

<400> SEQUENCE: 5
```

```
ctgaatttgc tgtgatccag g                                              21
```

<210> SEQ ID NO 6
<211> LENGTH: 46
<212> TYPE: DNA
<213> ORGANISM: Artificial Sequence
<220> FEATURE:
<223> OTHER INFORMATION: Synthetic construct - sequence inserted into
      NdeI site

<400> SEQUENCE: 6

```
cataatgggc catcatcatc atcatcacgg tggtcatatg tcccTT                   46
```

<210> SEQ ID NO 7
<211> LENGTH: 27
<212> TYPE: DNA
<213> ORGANISM: Artificial Sequence
<220> FEATURE:
<223> OTHER INFORMATION: Synthetic construct - sequence inserted into
      BamHI site

<400> SEQUENCE: 7

```
aaggggatc ctaaactgca gagatcc                                         27
```

<210> SEQ ID NO 8
<211> LENGTH: 60
<212> TYPE: DNA
<213> ORGANISM: Artificial Sequence
<220> FEATURE:
<223> OTHER INFORMATION: Synthetic construct - portion of sequence of
      resulting plasmid

<400> SEQUENCE: 8

```
aaggaggaga tatacataat gggccatcat catcatcatc acggtggtca tatgtccctt    60
```

<210> SEQ ID NO 9
<211> LENGTH: 27
<212> TYPE: DNA
<213> ORGANISM: Artificial Sequence
<220> FEATURE:
<223> OTHER INFORMATION: Synthetic construct - portion of sequence of
      resulting plasmid after ORF

<400> SEQUENCE: 9

```
aaggggatc ctaaactgca gagatcc                                         27
```

<210> SEQ ID NO 10
<211> LENGTH: 13
<212> TYPE: PRT
<213> ORGANISM: Artificial Sequence
<220> FEATURE:
<223> OTHER INFORMATION: Synthetic construct - N-terminal end of
      expressed Aurora kinase

<400> SEQUENCE: 10

```
Met His His His His His His Gly Gly His Met Ser Leu
1               5                   10
```

<210> SEQ ID NO 11
<211> LENGTH: 4
<212> TYPE: PRT
<213> ORGANISM: Artificial Sequence
<220> FEATURE:
<223> OTHER INFORMATION: Synthetic construct - C-terminal end of
      expressed Aurora kinase

<400> SEQUENCE: 11

Glu Gly Gly Ser
1

<210> SEQ ID NO 12
<211> LENGTH: 51
<212> TYPE: DNA
<213> ORGANISM: Artificial Sequence
<220> FEATURE:
<223> OTHER INFORMATION: Forward primer (PPfor)

<400> SEQUENCE: 12
gcagagatcc gaattcgagc tccgtcgacg gatggagtga aagagatgcg c                51

<210> SEQ ID NO 13
<211> LENGTH: 55
<212> TYPE: DNA
<213> ORGANISM: Artificial Sequence
<220> FEATURE:
<223> OTHER INFORMATION: Reverse primer (PPrev)

<400> SEQUENCE: 13
ggtggtggtg ctcgagtgcg gccgcaagct ttcatcatgc gccttctccc tgtac           55

<210> SEQ ID NO 14
<211> LENGTH: 19
<212> TYPE: DNA
<213> ORGANISM: Artificial Sequence
<220> FEATURE:
<223> OTHER INFORMATION: Forward primer

<400> SEQUENCE: 14
gacaagtggg aaatggagc                                                   19

<210> SEQ ID NO 15
<211> LENGTH: 19
<212> TYPE: DNA
<213> ORGANISM: Artificial Sequence
<220> FEATURE:
<223> OTHER INFORMATION: Reverse primer

<400> SEQUENCE: 15
cgcctcgttt ccccagctc                                                   19

<210> SEQ ID NO 16
<211> LENGTH: 12
<212> TYPE: DNA
<213> ORGANISM: Artificial Sequence
<220> FEATURE:
<223> OTHER INFORMATION: Synthetic construct - sequence inserted into
      NdeI site

<400> SEQUENCE: 16
catatgtccc tt                                                          12

<210> SEQ ID NO 17
<211> LENGTH: 29
<212> TYPE: DNA
<213> ORGANISM: Artificial Sequence
<220> FEATURE:
<223> OTHER INFORMATION: Synthetic construct - sequence inserted into
      BamHI site

<400> SEQUENCE: 17
aagggcatca tcaccatcac cactgatcc                                        29

<210> SEQ ID NO 18

```
<211> LENGTH: 26
<212> TYPE: DNA
<213> ORGANISM: Artificial Sequence
<220> FEATURE:
<223> OTHER INFORMATION: Synthetic construct - portion of sequence of
      resulting plasmid

<400> SEQUENCE: 18
aaggaggaga tatacatatg tccctt                                         26

<210> SEQ ID NO 19
<211> LENGTH: 29
<212> TYPE: DNA
<213> ORGANISM: Artificial Sequence
<220> FEATURE:
<223> OTHER INFORMATION: Synthetic construct - portion of sequence of
      resulting plasmid after ORF

<400> SEQUENCE: 19
aagggcatca tcaccatcac cactgatcc                                      29

<210> SEQ ID NO 20
<211> LENGTH: 8
<212> TYPE: PRT
<213> ORGANISM: Artificial Sequence
<220> FEATURE:
<223> OTHER INFORMATION: Synthetic construct - C-terminal end of
      expressed C-Abl

<400> SEQUENCE: 20

Glu Gly His His His His His His
1               5

<210> SEQ ID NO 21
<211> LENGTH: 39
<212> TYPE: DNA
<213> ORGANISM: Artificial Sequence
<220> FEATURE:
<223> OTHER INFORMATION: Mm05582dS4 oligonucleotide used to prepare
      plasmid for Abl T315I

<400> SEQUENCE: 21
ccaccattct acataatcat tgagttcatg acctatggg                           39

<210> SEQ ID NO 22
<211> LENGTH: 39
<212> TYPE: DNA
<213> ORGANISM: Artificial Sequence
<220> FEATURE:
<223> OTHER INFORMATION: Mm05582dA4 oligonucleotide used to prepare
      plasmid for Abl T315I

<400> SEQUENCE: 22
cccataggtc atgaactcaa tgattatgta gaatggtgg                           39
```

BICYCLIC PYRAZOLO PROTEIN KINASE MODULATORS

CROSS-REFERENCES TO RELATED APPLICATIONS

This application claims the benefit of U.S. Provisional Application No. 60/530,111, filed Dec. 17, 2003, and U.S. Provisional Application No. 60/598,221, filed Aug. 2, 2004, each of which is herein incorporated by reference in their entirety for all purposes.

BACKGROUND OF THE INVENTION

Mammalian protein kinases are important regulators of cellular functions. Because disfunctions in protein kinase activity have been associated with several diseases and disorders, protein kinases are targets for drug development.

The tyrosine kinase receptor, FMS-like tyrosine kinase 3 (FLT3), is implicated in cancers, including leukemia, such as acute myeloid leukemia (AML), acute lymphoblastic leukemia (ALL), and myelodysplasia. About one-quarter to one-third of AML patients have FLT3 mutations that lead to constitutive activation of the kinase and downstream signaling pathways. Although in normal humans, FLT3 is expressed mainly by normal myeloid and lymphoid progenitor cells, FLT3 is expressed in the leukemic cells of 70-80% of patients with AML and ALL. Inhibitors that target FLT3 have been reported to be toxic to leukemic cells expressing mutated and/or constitutively-active FLT3. Thus, there is a need to develop potent FLT3 inhibitors that may be used to treat diseases and disorders such as leukemia.

The Abelson non-receptor tyrosine kinase (c-Abl) is involved in signal transduction, via phosphorylation of its substrate proteins. In the cell, c-Abl shuttles between the cytoplasm and nucleus, and its activity is normally tightly regulated through a number of diverse mechanisms. Abl has been implicated in the control of growth-factor and integrin signaling, cell cycle, cell differentiation and neurogenesis, apoptosis, cell adhesion, cytoskeletal structure, and response to DNA damage and oxidative stress.

The c-Abl protein contains approximately 1150 amino-acid residues, organized into a N-terminal cap region, an SH3 and an SH2 domain, a tyrosine kinase domain, a nuclear localization sequence, a DNA-binding domain, and an actin-binding domain.

Chronic myelogenous leukemia (CML) is associated with the Philadelphia chromosomal translocation, between chromosomes 9 and 22. This translocation generates an aberrant fusion between the bcr gene and the gene encoding c-Abl. The resultant Bcr-Abl fusion protein has constitutively active tyrosine-kinase activity. The elevated kinase activity is reported to be the primary causative factor of CML, and is responsible for cellular transformation, loss of growth-factor dependence, and cell proliferation.

The 2-phenylaminopyrimidine compound imatinib (also referred to as STI-571, CGP 57148, or Gleevec) has been identified as a specific and potent inhibitor of Bcr-Abl, as well as two other tyrosine kinases, c-kit and platelet-derived growth factor receptor. Imatinib blocks the tyrosine-kinase activity of these proteins. Imatinib has been reported to be an effective therapeutic agent for the treatment of all stages of CML. However, the majority of patients with advanced-stage or blast crisis CML suffer a relapse despite continued imatinib therapy, due to the development of resistance to the drug. Frequently, the molecular basis for this resistance is the emergence of imatinib-resistant variants of the kinase domain of Bcr-Abl. The most commonly observed underlying amino-acid substitutions include Glu255Lys, Thr315Ile, Tyr293Phe, and Met351Thr.

MET was first identified as a transforming DNA rearrangement (TPR-MET) in a human osteosarcoma cell line that had been treated with N-methyl-N'-nitro-nitrosoguanidine (Cooper et al. 1984). The MET receptor tyrosine kinase (also known as hepatocyte growth factor receptor, HGFR, MET or c-Met) and its ligand hepatocyte growth factor ("HGF") have numerous biological activities including the stimulation of proliferation, survival, differentiation and morphogenesis, branching tubulogenesis, cell motility and invasive growth. Pathologically, MET has been implicated in the growth, invasion and metastasis of many different forms of cancer including kidney cancer, lung cancer, ovarian cancer, liver cancer and breast cancer. Somatic, activating mutations in MET have been found in human carcinoma metastases and in sporadic cancers such as papillary renal cell carcinoma. The evidence is growing that MET is one of the long-sought oncogenes controlling progression to metastasis and therefore a very interesting target. In addition to cancer there is evidence that MET inhibition may have value in the treatment of various indications including: Listeria invasion, Osteolysis associated with multiple myeloma, Malaria infection, diabetic retinopathies, psoriasis, and arthritis.

The tyrosine kinase RON is the receptor for the macrophage stimulating protein and belongs to the MET family of receptor tyrosine kinases. Like MET, RON is implicated in growth, invasion and metastasis of several different forms of cancer including gastric cancer and bladder cancer.

Because kinases have been implicated in numerous diseases and conditions, such as cancer, there is a need to develop new and potent protein kinase inhibitors that can be used for treatment. The present invention fulfills these and other needs in the art. Although certain protein kinases are specifically named herein, the present invention is not limited to inhibitors of these kinases, and, includes, within its scope, inhibitors of related protein kinases, and inhibitors of homologous proteins.

BRIEF SUMMARY OF THE INVENTION

It has been discovered that, surprisingly, bicyclic pyrazolo compounds may be used to modulate kinase activity and to treat diseases mediated by kinase activity. These novel bicyclic pyrazolo kinase modulators are described in detail below. In addition, inhibitory activities of selected compounds are disclosed herein.

In one aspect, the present invention provides a bicyclic pyrazolo kinase modulator having the formula:

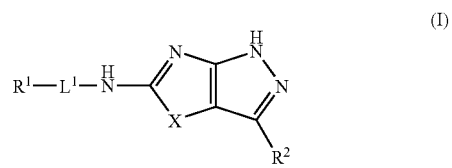

In Formula (I), X is —S—, —O—, or —N($R^{10}$)—. $R^{10}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$L^1$ is —C(Z)-, or —$SO_2$—. Z is =O, =S, or =$NR^{11}$. $R^{11}$ is hydrogen, —OH, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^1$ is hydrogen, —$CF_3$, amino, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, —$OR^{12}$, or —$NR^{13}R^{14}$. $R^{12}$, $R^{13}$, and $R^{14}$ are independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^2$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In another aspect, the present invention provides methods of modulating protein kinase activity using the bicyclic pyrazolo kinase modulators of the present invention. The method includes contacting the protein kinase with a bicyclic pyrazolo kinase modulator.

In another aspect, the present invention provides methods of treating a disease mediated by kinase activity in an organism. The method includes administering to the patient a therapeutically effective amount of a bicyclic pyrazolo kinase modulator of the present invention.

In another aspect, the present invention provides a pharmaceutical composition including a bicyclic pyrazolo kinase modulator in admixture with a pharmaceutically acceptable excipient.

DETAILED DESCRIPTION OF THE INVENTION

Definitions

Abbreviations used herein have their conventional meaning within the chemical and biological arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e. unbranched) or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl".

The term "alkylene" by itself or as part of another substituent means a divalent radical derived from an alkyl, as exemplified, but not limited, by —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or cyclic hydrocarbon radical, or combinations thereof, consisting of at least one carbon atoms and at least one heteroatom selected from the group consisting of O, N, P, Si and S, and wherein the nitrogen and sulfur atoms may optionally be oxidized and the nitrogen heteroatom may optionally be quatemized. The heteroatom(s) O, N, P and S and Si may be placed at any interior position of the heteroalkyl group or at the position at which alkyl group is attached to the remainder of the molecule. Examples include, but are not limited to, —$CH_2$-$CH_2$—O—$CH_3$, —$CH_2$-$CH_2$—NH—$CH_3$, —$CH_2$-$CH_2$—N($CH_3$)—$CH_3$, —$CH_2$—S—$CH_2$-$CH_3$, —$CH_2$-$CH_2$, —S(O)—$CH_3$, —$CH_2$-$CH_2$—S(O)$_2$—$CH_3$, —CH=CH—O—$CH_3$, —Si($CH_3$)$_3$, —$CH_2$-CH=N—$OCH_3$, —CH=CH—N($CH_3$)—$CH_3$, O—$CH_3$, —O—$CH_2$-$CH_3$, and —CN. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$-$CH_2$—S—$CH_2$-$CH_2$— and —$CH_2$—S—$CH_2$-$CH_2$—NH—$CH_2$—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O) OR'— represents both —C(O)OR'— and —R'OC(O)—. As described above, heteroalkyl groups, as used herein, include those groups that are attached to the remainder of the molecule through a heteroatom, such as —C(O)R', —C(O)NR', —NR'R", —OR', —SR', and/or —$SO_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

An "alkylesteryl," as used herein, refers to a moiety having the formula R'—C(O)O—R", wherein R' is an alkylene moiety and R" is an alkyl moiety.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

The term "cycloalkylalkyl" refers to a 3 to 7 membered cycloalkyl group attached to the remainder of the molecule via an unsubstituted alkylene group. Recitation of a specific number of carbon atoms (e.g. $C_1$-$C_{10}$ cycloalkylalkyl) refers to the number of carbon atoms in the alkylene group.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazoyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent derivatives of aryl and heteroaryl, respectively.

For brevity, the term "aryl" when used in combination with other terms (e.g., aryloxo, arylthioxo, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

The term "oxo" as used herein means an oxygen that is double bonded to a carbon atom.

Each of above terms (e.g., "alkyl," "heteroalkyl," "cycloalkyl, and "heterocycloalkyl", "aryl," "heteroaryl" as well as their divalent radical derivatives) are meant to include both substituted and unsubstituted forms of the indicated radical. Preferred substituents for each type of radical are provided below.

Substituents for alkyl, heteroalkyl, cycloalkyl, heterocycloalkyl monovalent and divalent derivative radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO$_2$R', —C(O)NR'R", —OC(O)NR'R", —NR"C(O)R', —NR"C(O)OR', —NR—C(NR'R"R'")=NR"", —NR—C(NR'R")=NR"', —S(O) R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From above discussion of substituents, one of skill in art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for alkyl radicals above, exemplary substituents for aryl and heteroaryl groups (as well as their divalent derivatives) are varied and are selected from, for example: halogen, —OR', —NR'R", —SR', -halogen, —SiR'R"R'", —OC(O)R', —C(O)R', —CO$_2$R', —C(O)NR'R", —OC(O)NR'R", —NR"C(O)R', —NR'—C(O)NR"R'", —NR"C(O)OR', —NR—C (NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro($C_1$-$C_4$)alkoxo, and fluoro ($C_1$-$C_4$)alkyl, in a number ranging from zero to the total number of open valences on aromatic ring system; and where R', R", R'" and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the invention includes more than one R group, for example, each of the R groups is independently selected as are each R', R", R'" and R"" groups when more than one of these groups is present.

Two of the substituents on adjacent atoms of aryl or heteroaryl ring may optionally form a ring of the formula -T-C(O)—(CRR')$_q$-U-, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)$_r$-B-, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'— (C"R'")$_d$—, where s and d are independently integers of from 0 to 3, and X' is —O—, —NR'—, —S—, —S(O)—, —S(O)$_2$—, or —S(O)$_2$NR'—. The substituents R, R', R" and R'" are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "heteroatom" or "ring heteroatom" is meant to include oxygen (O), nitrogen (N), sulfur (S), phosphorus (P), and silicon (Si).

The compounds of the present invention may exist as salts. The present invention includes such salts. Examples of applicable salt forms include hydrochlorides, hydrobromides, sulfates, methanesulfonates, nitrates, maleates, acetates, citrates, fumarates, tartrates (eg (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present invention contain relatively basic finctionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

The compounds of the present invention may also contain unnatural proportions of atomic isotopes at one or more of atoms that constitute such compounds. For example, the compounds may be radiolabeled with radioactive isotopes, such as for example tritium ($^{3}H$), iodine-125 ($^{125}I$) or carbon-14 ($^{14}C$). All isotopic variations of the compounds of the present invention, whether radioactive or not, are encompassed within the scope of the present invention.

The term "pharmaceutically acceptable salts" is meant to include salts of active compounds which are prepared with relatively nontoxic acids or bases, depending on the particular substituent moieties found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

The terms "a," "an," or "a(n)", when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, physiological conditions.

The terms "treating" or "treatment" in reference to a particular disease includes prevention of the disease.

I. Bicyclic Pyrazolo Kinase Modulators

In one aspect, the present invention provides a bicyclic pyrazolo kinase modulator having the formula:

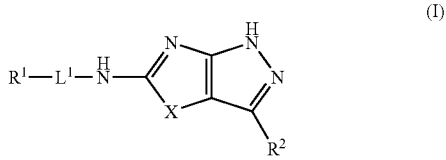

(I)

In Formula (I), X is —S—, —O—, or —N($R^{10}$)—. $R^{10}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$L^1$ is —C(Z)-, or —$SO_2$—. Z is =O, =S, or =$NR^{11}$. $R^{11}$ is hydrogen, —OH, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^1$ is hydrogen, —$CF_3$, amino, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, —$OR^{12}$, or —$NR^{13}R^{14}$. $R^{12}$, $R^{13}$, and $R^{14}$ are independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{13}$ and $R^{14}$ may be joined to from a ring with the nitrogen to which they are attached, wherein the ring is substituted or unsubstituted cycloalkyl, substituted or unsubstituted heterocycloalkyl, substituted or unsubstituted aryl, or substituted or unsubstituted heteroaryl.

$R^2$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In some embodiments, $R^2$ is attached to the remainder of the molecule via a carbon atom to form a carbon-carbon bond.

In other embodiments, if $R^2$ is unsubstituted phenyl, X is S, $L_1$ is —C(Z)-, and Z is =O, then $R^1$ is not unsubstituted phenyl. In another embodiments, if $R^2$ is unsubstituted aryl, X is S, $L_1$ is —C(Z)-, and Z is =O, then $R^1$ is not unsubstituted aryl. In other embodiments, if $R^2$ is substituted or unsubstituted phenyl, X is S, $L_1$ is —C(Z)-, and Z is =O, then $R^1$ is not substituted or unsubstituted phenyl. In another embodiment, $R^2$ and $R^1$ are not simultaneously unsubstituted phenyl. In another embodiment, $R^2$ and $R^1$ are not simultaneously unsubstituted aryl. In another embodiment, $R^2$ and $R^1$ are not simultaneously substituted or unsubstituted phenyl.

In an exemplary embodiment, X is —S—. In a related embodiment, Z is =O.

$R^2$ may be substituted or unsubstituted $C_1$-$C_{20}$ alkyl, substituted or unsubstituted 2 to 20 membered heteroalkyl, substituted or unsubstituted $C_3$-$C_8$ cycloalkyl, substituted or unsubstituted 3 to 8 membered heterocycloalkyl, substituted or unsubstituted aryl, or substituted or unsubstituted heteroaryl. $R^2$ may also be substituted or unsubstituted $C_1$-$C_{10}$ alkyl, substituted or unsubstituted 2 to 10 membered heteroalkyl, substituted or unsubstituted $C_3$-$C_7$ cycloalkyl, substituted or unsubstituted 3 to 7 membered heterocycloalkyl, substituted or unsubstituted aryl, or substituted or unsubstituted heteroaryl.

In some embodiments, $R^2$ is (1) unsubstituted $C_1$-$C_{10}$ alkyl; (2) unsubstituted 2 to 10 membered heteroalkyl; (3) unsubstituted $C_3$-$C_7$ cycloalkyl; (4) unsubstituted 3 to 7 membered heterocycloalkyl; (5) unsubstituted aryl; (6) unsubstituted heteroaryl;(7) substituted $C_1$-$C_{10}$ alkyl; (8) substituted 2 to 10 membered heteroalkyl; (9) substituted $C_3$-$C_7$ cycloalkyl; (10) substituted 3 to 7 membered heterocycloalkyl; (11) substituted aryl; or (12) substituted heteroaryl. In a related embodiment, (7), (8), (9), or (10) (i.e. alkyl, heteroalkyl, cycloalkyl, heterocycloalkyl) is substituted with an oxo, —OH, —$CF_3$, —COOH, halogen, $R^{21}$-substituted or unsubstituted $C_1$-$C_{10}$ alkyl, $R^{21}$-substituted or unsubstituted 2 to 10 membered heteroalkyl, $R^{21}$-substituted or unsubstituted $C_3$-$C_7$ cycloalkyl, $R^{22}$-substituted or unsubstituted 3 to 7 membered heterocycloalkyl, $R^{22}$-substituted or unsubstituted aryl, or $R^{22}$-substituted or unsubstituted heteroaryl, -$L^{22}$-C(O)R , -$L^{22}$-$OR^4$, -$L^{22}$-$NR^4R^5$, $OR^4$, or -$L^{22}$-S(O)$_m R^6$. In another related embodiment where $R^2$ is (11) or (12) (i.e. aryl or heteroaryl), (11) or (12) is substituted with an —OH, —$CF_3$, —COOH, halogen, $R^{21}$-substituted or unsubstituted $C_1$-$C_{10}$ alkyl, $R^{21}$-substituted or unsubstituted 2 to 10 membered heteroalkyl, $R^{21}$-substituted or unsubstituted $C_3$-$C_7$ cycloalkyl, $R^{21}$-substituted or unsubstituted 3 to 7 membered heterocycloalkyl, $R^{22}$-substituted or unsubstituted aryl, $R^{22}$-substituted or unsubstituted heteroaryl, -$L^{22}$-C(O)$R^3$, -$L^{22}$-$OR^4$, -$L^{22}$-$NR^4R^5$, or -$L^{22}$-S(O)$_m R^6$.

In some embodiments, where (11) or (12) is substituted with a $R^{21}$-substituted or unsubstituted 3 to 7 membered heterocycloalkyl, then the heterocycloalkyl is dioxolanyl, dioxanyl, trioxanyl, tetrahydrofuranyl, tetrahydrothiophenyl, tetrahydropyranyl, tetrahydrothiopyranyl, pyrrolidinyl, morpholino, piperidinyl, or piperazinyl. In other embodiments, where (11) or (12) is substituted with a $R^{22}$-substituted or unsubstituted heteroaryl, then the heteroaryl is pyrazolyl, furanyl, imidazolyl, isoxazolyl, oxadiazolyl, oxazolyl, pyrrolyl, pyridyl, pyrazyl, pyrimidyl, pyridazinyl, thiazolyl, isothioazolyl, triazolyl, or thienyl, triazinyl, or thiadiazolyl.

$R^3$ is hydrogen, $R^{21}$-substituted or unsubstituted $C_1$-$C_{10}$ alkyl, $R^{21}$-substituted or unsubstituted 2 to 10 membered heteroalkyl, $R^{21}$-substituted or unsubstituted $C_3$-$C_7$ cycloalkyl, $R^{21}$-substituted or unsubstituted 3 to 7 membered heterocycloalkyl, $R^{22}$-substituted or unsubstituted aryl, $R^{22}$-substituted or unsubstituted heteroaryl, —$OR^{31}$, or —$NR^{32}R^{33}$. $R^{31}$, $R^{32}$, and $R^{33}$ are independently hydrogen, $R^{21}$-substituted or unsubstituted $C_1$-$C_{10}$ alkyl, $R^{21}$-substituted or unsubstituted 2 to 10 membered heteroalkyl, $R^{21}$-substituted or unsubstituted $C_3$-$C_7$ cycloalkyl, $R^{21}$-substituted or unsubstituted 3 to 7 membered heterocycloalkyl, $R^{22}$-substituted or unsubstituted aryl, or $R^{22}$-substituted or unsubstituted heteroaryl.

$R^4$ and $R^5$ are independently hydrogen, —$CF_3$, $R^{21}$-substituted or unsubstituted $C_1$-$C_{10}$ alkyl, $R^{21}$-substituted or unsubstituted 2 to 10 membered heteroalkyl, $R^{21}$-substituted or unsubstituted $C_3$-$C_7$ cycloalkyl, $R^{21}$-substituted or unsubstituted 3 to 7 membered heterocycloalkyl, $R^{22}$-substituted or unsubstituted aryl, $R^{22}$-substituted or unsubstituted heteroaryl, or —C(O)$R^4$. $R^{41}$ is hydrogen, $R^{21}$-substituted or unsubstituted $C_1$-$C_{10}$ alkyl, $R^{21}$-substituted or unsubstituted 2 to 10 membered heteroalkyl, $R^{21}$-substituted or unsubstituted $C_3$-$C_7$ cycloalkyl, $R^{21}$-substituted or unsubstituted 3 to 7 membered heterocycloalkyl, $R^{22}$-substituted or unsubstituted aryl, or $R^{22}$-substituted or unsubstituted heteroaryl, $R^6$ is hydrogen, $R^{21}$-substituted or unsubstituted $C_1$-$C_{10}$ alkyl, $R^{21}$-substituted or unsubstituted 2 to 10 membered heteroalkyl, $R^{21}$-substituted or unsubstituted $C_3$-$C_7$ cycloalkyl, $R^{21}$-substituted or unsubstituted 3 to 7 membered heterocycloalkyl, $R^{22}$-substituted or unsubstituted aryl, or $R^{22}$-substituted or unsubstituted heteroaryl.

$L^{22}$ is a bond, unsubstituted $C_1$-$C_{10}$ alkylene or unsubstituted heteroalkylene. The symbol m represent the integers 0, 1, or 2.

$R^{21}$ is oxo, —OH, —COOH, —$CF_3$, amino, halogen, $R^{23}$-substituted or unsubstituted 2 to 10 membered heteroalkyl, $R^{23}$-substituted or unsubstituted $C_3$-$C_7$ cycloalkyl, $R^{23}$-substituted or unsubstituted 3 to 7 membered heterocycloalkyl, $R^{24}$-substituted or unsubstituted aryl, or $R^{24}$-substituted or unsubstituted heteroaryl. $R^{22}$ is —OH, —COOH, amino, halogen, —$CF_3$, $R^{23}$-substituted or unsubstituted 2 to 10 membered heteroalkyl, $R^{23}$-substituted or unsubstituted $C_3$-$C_7$ cycloalkyl, $R^{23}$-substituted or unsubstituted 3 to 7 membered heterocycloalkyl, $R^{24}$-substituted or unsubstituted aryl, or $R^{24}$-substituted or unsubstituted heteroaryl.

In some embodiments, if $R^{21}$ or $R^{22}$ is substituted or unsubstituted heterocycloalkyl, the the heterocycloalkyl is hydantoinyl, dioxolanyl, dioxanyl, trioxanyl, tetrahydrothienyl, tetrahydrofuranyl, tetrahydrothiophenyl, tetrahydropyranyl, tetrahydrothiopyranyl, pyrrolidinyl, morpholino, piperidinyl, or piperazinyl.

In other embodiments, if $R^{21}$ or $R^{22}$ is substituted or unsubstituted heteroaryl, then the heteroaryl is pyrazolyl, furanyl, imidazolyl, isoxazolyl, oxadiazolyl, oxazolyl, pyrrolyl, pyridyl, pyrazyl, pyrimidyl, pyridazinyl, thiazolyl, isothiozolyl, triazolyl, thienyl, triazinyl, or thiadiazolyl.

$R^{23}$ is oxo, —OH, —COOH, amino, halogen, —$CF_3$, unsubstituted $C_1$-$C_{10}$ alkyl, unsubstituted 2 to 10 membered heteroalkyl, unsubstituted $C_3$-$C_7$ cycloalkyl, unsubstituted 3 to 7 membered heterocycloalkyl, unsubstituted aryl, or unsubstituted heteroaryl. $R^{24}$ is —OH, —COOH, amino, halogen, —$CF_3$, unsubstituted $C_1$-$C_{10}$ alkyl, unsubstituted 2 to 10 membered heteroalkyl, unsubstituted $C_3$-$C_7$ cycloalkyl, unsubstituted 3 to 7 membered heterocycloalkyl, unsubstituted aryl, unsubstituted heteroaryl.

In some embodiments, $R^2$ is substituted or unsubstituted aryl, or substituted or unsubstituted heteroaryl. In other embodiments, $R^2$ is substituted or unsubstituted cycloalkyl, substituted or unsubstituted heterocycloalkyl, substituted or unsubstituted alkyl, or substituted or unsubstituted heteroalkyl.

Where $R^2$ is substituted (e.g. substituted aryl or heteroaryl), the substituent (also referred to herein as the $R^2$ substituent) may be a(n): (1) unsubstituted $C_1$-$C_{10}$ alkyl; (2) unsubstituted 2 to 10 membered heteroalkyl; (3) unsubstituted $C_3$-$C_7$ cycloalkyl; (4) unsubstituted 3 to 7 membered heterocycloalkyl; (5) unsubstituted aryl; (6) unsubstituted heteroaryl; (7) halogen; (8) —OH; (9) amino; (10) —$CF_3$; (11) 3 to 7 membered heterocycloalkyl substituted with unsubstituted $C_1$-$C_{10}$ alkyl; or (12) $C_1$-$C_{10}$ alkyl substituted with an unsubstituted aryl. In some related embodiments, $R^2$ is a substituted aryl or substituted heteroaryl.

In another embodiment, the $R^2$ substituent is a: (1) halogen; (2) -$L^{22}$-C(O)$R^3$; (3) -$L^{22}$-O$R^4$; (4) -$L^{22}$-N$R^4R^5$; or (5) -$L^{22}$-S(O)$_m$$R^6$. $R^3$ may be hydrogen, unsubstituted $C_1$-$C_{10}$ alkyl, —O$R^{31}$, or —N$R^{32}R^{33}$. $R^{31}$, $R^{32}$, and $R^{33}$ may independently be hydrogen, unsubstituted $C_1$-$C_{10}$ alkyl, or unsubstituted $C_3$-$C_7$ cycloalkyl. $L^{22}$ may be unsubstituted $C_1$-$C_{10}$ alkylene. $R^4$ may be hydrogen, —$CF_3$, —$CHF_2$, unsubstituted $C_1$-$C_{10}$ alkyl, unsubstituted $C_3$-$C_7$ cycloalkyl, unsubstituted $C_1$-$C_{10}$ cycloalkylalkyl, or —C(O)$R^{41}$. $R^{41}$ may be hydrogen, or unsubstituted $C_1$-$C_{10}$ alkyl. $R^4$ and $R^5$ may independently be hydrogen, unsubstituted $C_1$-$C_{10}$ alkyl, or —C(O)$R^{41}$. $R^{41}$ may independently be hydrogen, or unsubstituted $C_1$-$C_{10}$ alkyl, or $R^7$ may be hydrogen or unsubstituted $C_1$-$C_{10}$ alkyl.

In some embodiments, where $R^2$ is substituted or unsubstituted aryl, then the aryl is phenyl, benz[cd]indol-2(1H)-one-yl, oxindolyl, indazolinonyl, benzoimidazolyl, indolyl, benzodioxanyl, coumarinyl, chromonyl, benzopyrazyl, naphthyl, quinolyl, or isoquinolyl.

In other embodiments, where $R^2$ is substituted or unsubstituted heteroaryl, then the heteroaryl is pyrazolyl, furanyl, imidazolyl, isoxazolyl, oxadiazolyl, oxazolyl, pyrrolyl, pyridyl, pyrimidyl, pyrazyl, pyridazinyl, hyadantoin, thiazolyl, isothioazolyl, triazolyl, thienyl, triazinyl, thiadiazolyl.

In certain embodiments, where $R^2$ is substituted or unsubstituted heterocycloalkyl, then the heterocycloalkyl is hydantoinyl, dioxolanyl, dioxanyl, trioxanyl, tetrahydrothienyl, tetrahydrofuranyl, tetrahydrothiophenyl, tetrahydropyranyl, tetrahydrothiopyranyl, pyrrolidinyl, morpholino, piperidinyl, or piperazinyl.

$R^1$ may be hydrogen, amino, substituted or unsubstituted $C_1$-$C_{10}$ alkyl, substituted or unsubstituted 2 to 10 membered heteroalkyl, substituted or unsubstituted $C_3$-$C_7$ cycloalkyl, substituted or unsubstituted 3 to 7 membered heterocycloalkyl, substituted or unsubstituted aryl, or substituted or unsubstituted heteroaryl.

In an exemplary embodiment, R' is: (1) —$CF_3$; (2) unsubstituted $C_1$-$C_{10}$ alkyl; (3) unsubstituted 2 to 10 membered heteroalkyl; (4) unsubstituted $C_3$-$C_7$ cycloalkyl; (5) unsubstituted 3 to 7 membered heterocycloalkyl; (6) unsubstituted aryl; (7) unsubstituted heteroaryl; (8) substituted $C_1$-$C_{10}$ alkyl; (9) substituted 2 to 10 membered heteroalkyl; (10) substituted $C_3$-$C_7$ cycloalkyl; (11) substituted 3 to 7 membered heterocycloalkyl; (12) substituted aryl; or (13) substituted heteroaryl. In a related embodiment, (8), (9), (10) or (11) is substituted with an oxo, —OH, —$CF_3$, —COOH, halogen, $R^{15}$-substituted or unsubstituted $C_1$-$C_{10}$ alkyl, $R^5$-substituted or unsubstituted 2 to 10 membered heteroalkyl, $R^{15}$-substituted or unsubstituted $C_3$-$C_7$ cycloalkyl, $R^{15}$-substituted or unsubstituted 3 to 7 membered heterocycloalkyl, $R^{16}$-substituted or unsubstituted aryl, $R^{16}$-substituted or unsubstituted heteroaryl, -$L^{11}$-C(O)$R^{100}$, -$L^{11}$-O$R^{104}$, -$L^{11}$-N$R^{104}R^{105}$, or -$L^{11}$-S(O)$_q$-$R^{107}$. In another related embodiment, (12) or (13) is substituted with an —OH, —$CF_3$, —COOH, halogen, $R^{15}$-substituted or unsubstituted $C_1$-$C_{10}$ alkyl, $R^{15}$-substituted or unsubstituted 2 to 10 membered heteroalkyl, $R^{15}$-substituted or unsubstituted $C_3$-$C_7$ cycloalkyl, $R^{15}$-substituted or unsubstituted 3 to 7 membered heterocycloalkyl, $R^{16}$-substituted or unsubstituted aryl, $R^{16}$- substituted or unsubstituted heteroaryl, -$L^{11}$-C(O)$R^{100}$, -$L^{11}$-O$R^{104}$-$L^{11}$-N$R^{104}$ $R^{105}$, or -$L^{11}$-S(O)$_q$-$R^{107}$.

$R^{100}$ is hydrogen, $R^{15}$-substituted or unsubstituted $C_1$-$C_{10}$ alkyl, $R^{15}$-substituted or unsubstituted 2 to 10 membered heteroalkyl, $R^{15}$-substituted or unsubstituted $C_3$-$C_7$ cycloalkyl, $R^{15}$-substituted or unsubstituted 3 to 7 membered heterocycloalkyl, $R^{16}$-substituted or unsubstituted aryl, $R^{16}$-substituted or unsubstituted heteroaryl, —O$R^{101}$, or —N$R^{102}R^{103}$. $R^{101}$, $R^{102}$, and $R^{103}$ are independently hydrogen, $R^{15}$-substituted or unsubstituted $C_1$-$C_{10}$ alkyl, $R^{15}$-substituted or unsubstituted 2 to 10 membered heteroalkyl, $R^{15}$-substituted or unsubstituted $C_3$-$C_7$ cycloalkyl, $R^{15}$-substituted or unsubstituted 3 to 7 membered heterocycloalkyl, $R^{16}$-substituted or unsubstituted aryl, or $R^{16}$-substituted or unsubstituted heteroaryl.

$R^{104}$ and $R^{105}$ are independently hydrogen, —CF$_3$, $R^{15}$-substituted or unsubstituted $C_1$-$C_{10}$ alkyl, $R^{15}$-substituted or unsubstituted 2 to 10 membered heteroalkyl, $R^{15}$-substituted or unsubstituted $C_3$-$C_7$ cycloalkyl, $R^{15}$-substituted or unsubstituted 3 to 7 membered heterocycloalkyl, $R^{16}$-substituted or unsubstituted aryl, $R^{16}$-substituted or unsubstituted heteroaryl, or —C(O)$R^{106}$. $R^{106}$ is independently hydrogen, $R^{15}$-substituted or unsubstituted $C_1$-$C_{10}$ alkyl, $R^{15}$-substituted or unsubstituted 2 to 10 membered heteroalkyl, $R^{15}$-substituted or unsubstituted $C_3$-$C_7$ cycloalkyl, $R^{15}$-substituted or unsubstituted 3 to 7 membered heterocycloalkyl, $R^{16}$-substituted or unsubstituted aryl, or $R^{16}$-substituted or unsubstituted heteroaryl.

$R^{107}$ is hydrogen, $R^{15}$-substituted or unsubstituted $C_1$-$C_{10}$ alkyl, $R^{15}$-substituted or unsubstituted 2 to 10 membered heteroalkyl, $R^{15}$-substituted or unsubstituted $C_3$-$C_7$ cycloalkyl, $R^{15}$-substituted or unsubstituted 3 to 7 membered heterocycloalkyl, $R^{16}$-substituted or unsubstituted aryl, or $R^{16}$-substituted or unsubstituted heteroaryl.

$L^{11}$ is a bond, unsubstituted $C_1$-$C_{10}$ alkylene or unsubstituted heteroalkylene. The symbol q represents the integers 0, 1, or 2.

$R^{15}$ is oxo, —OH, —COOH, —CF$_3$, halogen, $R^{17}$-substituted or unsubstituted $C_1$-$C_{10}$ alkyl, $R^{17}$-substituted or unsubstituted 2 to 10 membered heteroalkyl, $R^{17}$-substituted or unsubstituted $C_3$-$C_7$ cycloalkyl, $R^{17}$-substituted or unsubstituted 3 to 7 membered heterocycloalkyl, $R^{18}$-substituted or unsubstituted aryl, or $R^{18}$-substituted or unsubstituted heteroaryl. $R^{16}$ is —OH, —COOH, —CF$_3$, halogen, $R^{17}$-substituted or unsubstituted $C_1$-$C_{10}$ alkyl, $R^{17}$-substituted or unsubstituted 2 to 10 membered heteroalkyl, $R^{17}$-substituted or unsubstituted $C_3$-$C_7$ cycloalkyl, $R^{17}$-substituted or unsubstituted 3 to 7 membered heterocycloalkyl, $R^{8}$-substituted or unsubstituted aryl, or $R^{18}$-substituted or unsubstituted heteroaryl.

$R^{17}$ is oxo, —OH, —COOH, —CF$_3$, halogen, unsubstituted $C_1$-$C_{10}$ alkyl, unsubstituted 2 to 10 membered heteroalkyl, unsubstituted $C_3$-$C_7$ cycloalkyl, unsubstituted 3 to 7 membered heterocycloalkyl, unsubstituted aryl, or unsubstituted heteroaryl. $R^{18}$ is —OH, —COOH, —CF$_3$, halogen, unsubstituted $C_1$-$C_{10}$ alkyl, unsubstituted 2 to 10 membered heteroalkyl, unsubstituted $C_3$-$C_7$ cycloalkyl, unsubstituted 3 to 7 membered heterocycloalkyl, unsubstituted aryl, or unsubstituted heteroaryl.

In some embodiments, $R^{15}$ is oxo, —OH, —COOH, —CF$_3$, halogen, unsubstituted $C_1$-$C_{10}$ alkyl, unsubstituted 2 to 10 membered heteroalkyl, unsubstituted $C_3$-$C_7$ cycloalkyl, unsubstituted 3 to 7 membered heterocycloalkyl, unsubstituted aryl, or unsubstituted heteroaryl. In other embodiments, $R^{16}$ is —OH, —COOH, —CF$_3$, halogen, unsubstituted $C_1$-$C_{10}$ alkyl, unsubstituted 2 to 10 membered heteroalkyl, unsubstituted $C_3$-$C_7$ cycloalkyl, unsubstituted 3 to 7 membered heterocycloalkyl, unsubstituted aryl, or unsubstituted heteroaryl.

In certain embodiments, where $R^{15}$ or $R^{16}$ is substituted or unsubstituted heterocycloalkyl, the heterocycloalkyl is hydantoinyl, dioxolanyl, dioxanyl, trioxanyl, tetrahydrothienyl, tetrahydrofuranyl, tetrahydrothiophenyl, tetrahydropyranyl, tetrahydrothiopyranyl, pyrrolidinyl, morpholino, piperidinyl, or piperazinyl.

In other embodiments, where $R^{15}$ or $R^{16}$ is substituted or unsubstituted heteroaryl, the heteroaryl is pyrazolyl, furanyl, imidazolyl, isoxazolyl, oxadiazolyl, oxazolyl, pyrrolyl, pyridyl, pyrazyl, pyrimidyl, pyridazinyl, thiazolyl, isothioazolyl, triazolyl, or thienyl, triazinyl, or thiadiazolyl.

$R^1$ may be: (1) unsubstituted $C_1$-$C_{10}$ alkyl; (2) unsubstituted 2 to 10 membered heteroalkyl; (3) unsubstituted $C_3$-$C_7$ cycloalkyl; (4) unsubstituted 3 to 7 membered heterocycloalkyl; (5) substituted $C_1$-$C_{10}$ alkyl; (6) substituted 2 to 10 membered heteroalkyl; (7) substituted $C_3$-$C_7$ cycloalkyl; (8) substituted 3 to 7 membered heterocycloalkyl; (9) substituted phenyl; or (10) substituted heteroaryl. In some related embodiments, (5), (6), (7), or (8) is substituted with an oxo, —OH, —CF$_3$, —COOH, halogen, $R^{15}$-substituted or unsubstituted $C_1$-$C_{10}$ alkyl, or $R^{15}$-substituted or unsubstituted 2 to 10 membered heteroalkyl. In other related embodiments, (9) or (10) is substituted with an —OH, —CF$_3$, —COOH, halogen, $R^{15}$-substituted or unsubstituted $C_1$-$C_{10}$ alkyl, or $R^{15}$-substituted or unsubstituted 2 to 10 membered heteroalkyl.

$R^{15}$ may be oxo, —OH, —COOH, —CF$_3$, halogen, unsubstituted $C_1$-$C_{10}$ alkyl, or unsubstituted 2 to 10 membered heteroalkyl.

In an exemplary embodiment, $R^1$ is: (1) unsubstituted $C_1$-$C_{10}$ alkyl; (2) unsubstituted 2 to 10 membered heteroalkyl; (3) unsubstituted $C_3$-$C_7$ cycloalkyl; (4) unsubstituted 3 to 7 membered heterocycloalkyl; (5) $C_1$-$C_{10}$ alkyl substituted with an oxo, —OH, —COOH, —CF$_3$, halogen, unsubstituted $C_1$-$C_{10}$ alkyl, unsubstituted 2 to 10 membered heteroalkyl, unsubstituted $C_3$-$C_7$ cycloalkyl, unsubstituted 3 to 7 membered heterocycloalkyl, unsubstituted aryl, or unsubstituted heteroaryl; (6) 2 to 10 membered heteroalkyl substituted with an oxo, —OH, —CF$_3$, —COOH, halogen, unsubstituted $C_1$-$C_{10}$ alkyl, 2 to 10 membered heteroalkyl, unsubstituted $C_3$-$C_7$ cycloalkyl, unsubstituted 3 to 7 membered heterocycloalkyl, unsubstituted aryl, or unsubstituted heteroaryl; (7) $C_3$-$C_7$ cycloalkyl substituted with —OH, —CF$_3$, —COOH, halogen, unsubstituted $C_1$-$C_{10}$ alkyl, or unsubstituted 2 to 10 membered heteroalkyl; (8) 3 to 7 membered heterocycloalkyl substituted with —OH, —CF$_3$, —COOH, halogen, unsubstituted $C_1$-$C_{10}$ alkyl, or unsubstituted 2 to 10 membered heteroalkyl; (9) phenyl substituted with —OH, —CF$_3$, —COOH, halogen, unsubstituted $C_1$-$C_{10}$ alkyl, or unsubstituted 2 to 10 membered heteroalkyl; or (10) heteroaryl substituted with —OH, —CF$_3$, —COOH, halogen, unsubstituted $C_1$-$C_{10}$ alkyl, or unsubstituted 2 to 10 membered heteroalkyl.

In another exemplary embodiment, where $R^1$ is a substituted or unsubstituted heteroaryl, the heteroaryl is pyrazolyl, furanyl, imidazolyl, isoxazolyl, oxadiazolyl, oxazolyl, pyrrolyl, pyridyl, pyrimidyl, pyrazyl, pyridazinyl, thiazolyl, isothioazolyl, triazolyl, thienyl, triazinyl, or thiadiazolyl.

In some embodiments, where $R^1$ is a substituted or unsubstituted heterocycloalkyl, then the heterocycloalkyl is hydantoinyl, dioxolanyl, dioxanyl, trioxanyl, tetrahydrothienyl, tetrahydrofuranyl, tetrahydrothiophenyl, tetrahydropyranyl, tetrahydrothiopyranyl, pyrrolidinyl, morpholino, piperidinyl, or piperazinyl.

In some embodiments, where $R^1$ is substituted, the substituent (also referred to herein as an $R^1$ substituent) is a: (1) halogen; (2) -$L^{11}$-C(O)$R^{100}$; (3) -$L^{11}$-O$R^{104}$; (4) -$L^{11}$-N$R^{104}R^{105}$; or (5) -$L^{11}$-S(O)$_q R^{107}$. In a related embodiment, $R^{15}$ is oxo, —OH, —COOH, —CF$_3$, halogen, unsubstituted $C_1$-$C_{10}$ alkyl, unsubstituted 2 to 10 membered heteroalkyl, unsubstituted $C_3$-$C_7$ cycloalkyl, unsubstituted 3 to 7 membered heterocycloalkyl, unsubstituted aryl, or unsubstituted heteroaryl, and $R^{16}$ is —OH, —COOH, —CF$_3$, halogen, unsubstituted $C_1$-$C_{10}$ alkyl, unsubstituted 2 to 10 membered heteroalkyl, unsubstituted $C_3$-$C_7$ cycloalkyl, unsubstituted 3 to 7 membered heterocycloalkyl, unsubstituted aryl, or unsubstituted heteroaryl.

II. Exemplary Syntheses

The compounds of the invention are synthesized by an appropriate combination of generally well known synthetic methods. Techniques useful in synthesizing the compounds of the invention are both readily apparent and accessible to those of skill in the relevant art, including the techniques disclosed in Elnagdi, et al., *J. Heterocyclic Chem.*, 16: 61-64 (1979), Pawar, et al., *Indian J. Chem.*, 28B: 866-867 (1989), Chande, et al., *Indian J. Chem.*, 35B: 373-376 (1996), and in the following patents DE2429195 (1974), U.S. Pat. No. 6,566,363 (2003), which are incorporated in reference in their entirety for all purposes. The discussion below is offered to illustrate certain of the diverse methods available for use in assembling the compounds of the invention. However, the discussion is not intended to define the scope of reactions or reaction sequences that are useful in preparing the compounds of the present invention. The compounds of this invention may be made by the procedures and techniques disclosed in the Examples section below, as well as by known organic synthesis techniques.

In the exemplary syntheses below, the symbols X, $R^{10}$, $L^1$, $R^1$, $R^2$, $R^{11}$, $R^{13}$, and $R^{14}$ are, unless specified otherwise, defined as above in the section entitled "Bicyclic Pyrazolo Kinase Modulators."

General Scheme I

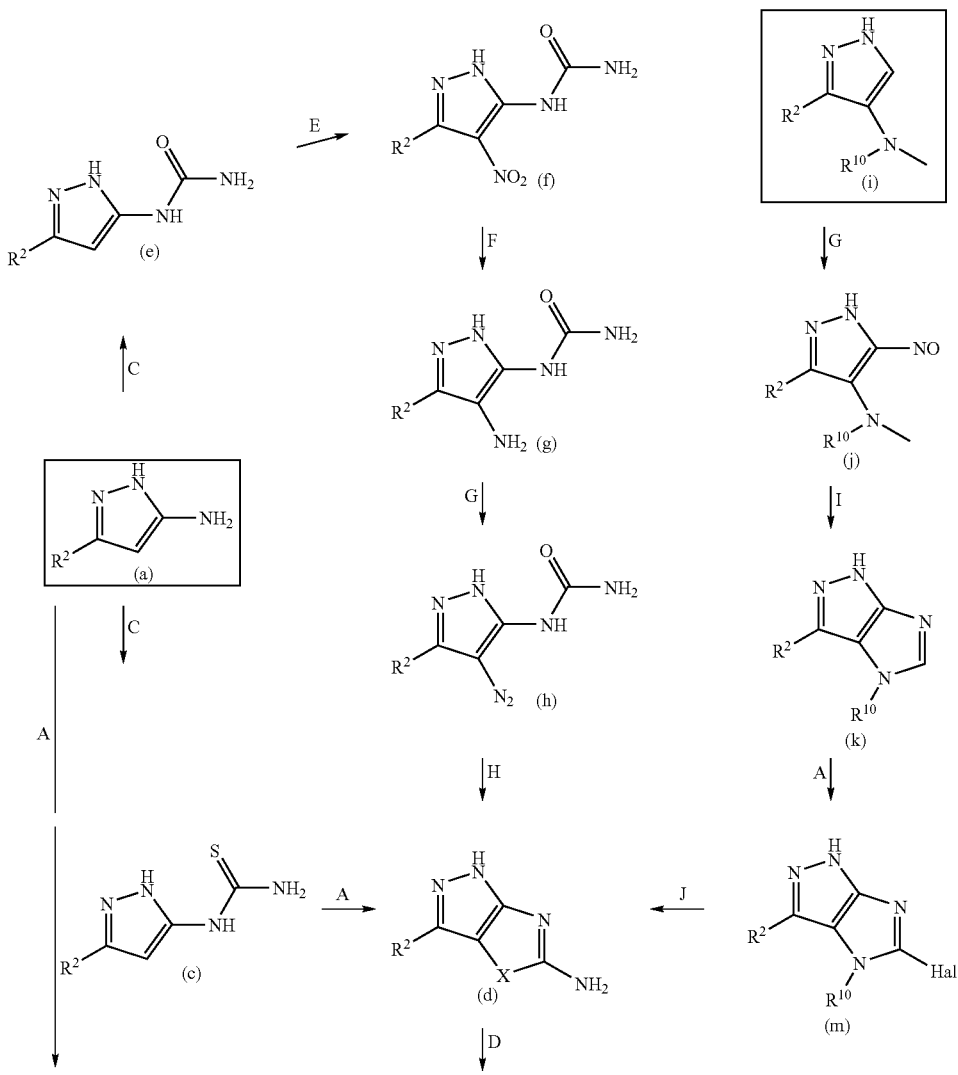

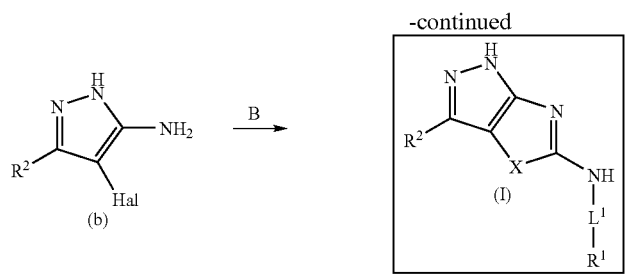

In step A of general scheme I, synthesis of the required halogenated intermediates (b), or cyclized intermediates (d) or (m), is accomplished by reacting a derivative (a), (c) or (k) respectively, with a suitable halogenating reagent, such as chlorine, bromine or iodine or a suitable halogen containing reagent such as ICl, N-chlorosuccinimide, N-bromosuccinimide, N-iodosuccinimide, or a tribromide source such as benzyltrimethylammonium tribromide, in suitable solvents such as acetic acid, DMF, ethereal solvents, or halogenated hydrocarbons, at temperatures ranging from −10° C. to 100° C.

Step B exemplifies cyclization to end products by reacting halogenated species (b) with an acyl isothiocyanate reagent such as benzoyl isothiocyanate or furan-2-carbonyl isothiocyanate, and optionally by further treatment with a source of sulfur nucleophiles such as Lawesson's reagent, in suitable solvents, such as ethereal solvents, DMF, pyridine, or DMSO at temperatures ranging from 20° C. to 180° C.

In step C, synthesis of the required thiourea (c) or urea (e) is performed by reacting a derivative (a) with thiocarbonyl reagents such as thiophosgene or thiocarbonyldiimidazole, or carbonyl reagents such as phosgene, triphosgene or carbonyldiimidazole, followed by treatment with ammonia or an ammonium source such as ammonium hydroxide, in suitable solvents such as halogenated hydrocarbons, ethereal solvents, THF, DMF, and water mixtures thereof, at temperatures ranging from −30° C. to 50° C.

Step D exemplifies the synthesis of end products of general formula (I) by reacting intermediate (d), optionally protected at the NH site, with suitable electrophiles such as acid chlorides, isocyanates, isothiocyanates, sulfonyl chlorides, imidoyl chlorides, imidoate esters or isothioureas, in suitable solvents such as ethereal solvents, DMF, DMSO, at temperatures ranging from 20° C. to 200° C., followed by basic hydrolysis with bases such as sodium hydroxide or triethylamine in suitable solvents such as alcohols, ethereal solvents, DMF, and water mixtures thereof, at temperatures ranging from 0° C. to 100° C.

In step E, synthesis of the required nitrated intermediate (f) is accomplished by reacting derivative (e) with a suitable nitrating reagent such as nitric acid, nitronium salts, ethyl nitrate or nitrogen dioxide, in the presence or absence of sulfuric acid or Lewis-acid catalyst, in suitable solvents such as water, acetic acid, or halogenated hydrocarbons, at temperatures ranging from −78° C. to 50° C.

Step F shows the exemplary synthesis of the required intermediate (g) by reacting derivative (f) with a suitable reducing agent such as hydrogen gas, zinc, iron, tin chloride, or sodium sulfide, in the presence or absence of a catalyst, such as palladium, or HCl, in suitable solvents such as water, alcohols, DMF, or ethereal solvents, at temperatures ranging from 20° C. to 200° C.

In step G, synthesis of the required diazonium intermediate (h), or nitroso intermediate (j), is accomplished by reacting derivative (g), or (i) respectively, with a suitable "nitrite" reagent in acidic media, such as sodium nitrite or isoamyl nitrite, in a suitable solvent such as water or mixture thereof with an organic solvent such as alcohols, ethereal solvents, or DMF, at temperatures ranging from −78° C. to 50° C.

Step H exemplifies synthesis of the required cyclized intermediate (d) by irradiating derivative (h) with a suitable light source such as a 250 W mercury lamp, in a suitable solvent such as alcohols, ethereal solvents, halogenated hydrocarbons, or DMF, at temperatures ranging from 20° C. to 100° C.

Step I shows the synthesis of the required cyclized intermediate (k) by heating derivative (j) in a suitable solvent such as pyridine, at temperatures ranging from 50° C. to 180° C.

In step J, synthesis of the required intermediate (d) is performed by reacting derivative (m) with ammonia or an ammonium source such as ammonium hydroxide, in suitable solvents such as halogenated hydrocarbons, alcohols, ethereal solvents, or DMF, at temperatures ranging from 20° C. to 180° C.

In addition to general scheme I above, the following exemplary schemes are presented to further illustrate methods of synthesizing the bicyclic pyrazolo kinase modulators of the present invention.

Scheme 1

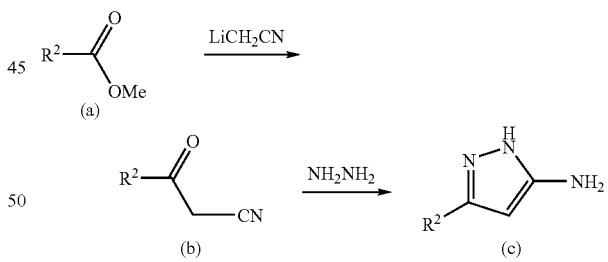

In Scheme 1, methyl ester (a) is reacted with lithiated acetonitrile at low temperature to give propionitrile (b). Compound (b) is then treated with hydrazine to provide aminopyrazole (c).

Scheme 2

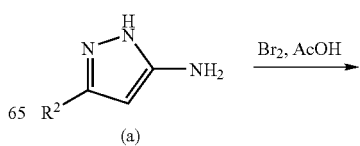

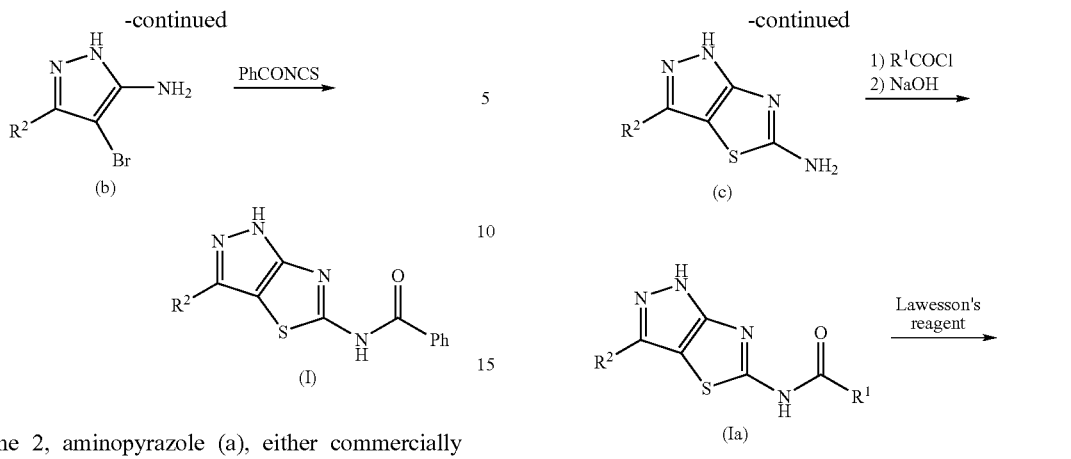

In Scheme 2, aminopyrazole (a), either commercially available or prepared synthetically as described in Scheme 1, is brominated with a solution of bromine in acetic acid. Brominated pyrazole (b) is then treated with an acyl isothiocyanate, such as benzoyl isothiocyanate or furan-2-carbonyl isothiocyanate, to give (1). The cyclization reaction is achieved in either dioxane under thermal conditions, or pyridine under microwave conditions.

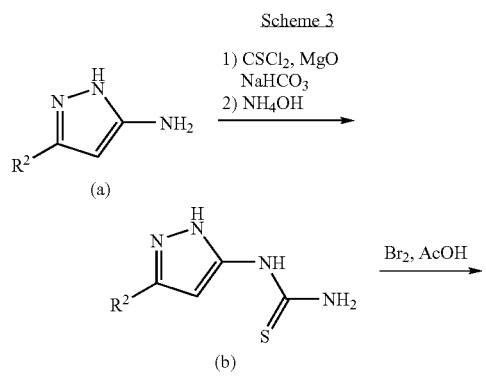

In an alternative method, as shown in Scheme 3, aminopyrazole (a) is treated with thiophosgene in the presence of magnesium oxide and sodium bicarbonate in dioxane/water mixture, followed by ammonium hydroxide to provide monosubstituted thiourea (b). Subsequent treatment of (b) with bromine in acetic acid affords cyclized product (c). Compound (c) is reacted with an excess of acyl chloride at reflux temperature, followed by treatment with sodium hydroxide (or other basic hydrolysis conditions, such as $Et_3N$ in $THF/H_2O$), to afford (Ia), or (Ib) after treatment with Lawesson's reagent.

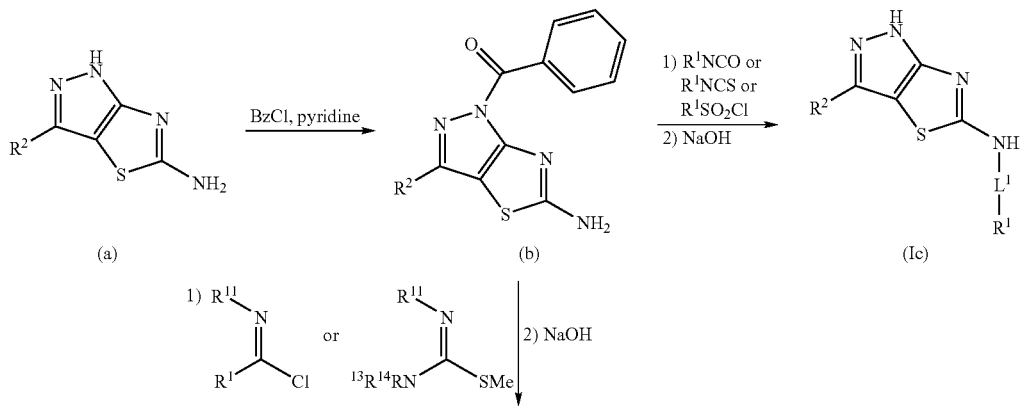

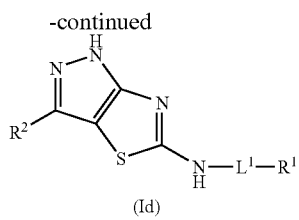

(Id)

In Scheme 4, pyrazolothiazolamine (a) is protected as a benzamide with benzoyl chloride to give (b). Subsequent treatment with isocyanate, isothiocyanate, or sulfonyl chloride reagents, followed by basic hydrolysis with sodium hydroxide, afford (Ic). Similarly, protected pyrazolothiazolamine (b) is reacted with reagents such as imidoyl chlorides (or imidoate ester equivalent) or methylisothioureas to give (Id).

The compounds of the present invention may be synthesized using one or more protecting groups generally known in the art of chemical synthesis. The term "protecting group" refers to chemical moieties that block some or all reactive moieties of a compound and prevent such moieties from participating in chemical reactions until the protective group is removed, for example, those moieties listed and described in Greene, et al., Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and t-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, without limitation, methyl, ethyl, and acetyl in the presence of amines blocked with acid labile groups such as t-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base- protecting groups since the former are stable and can be subsequently removed by metal or pi-acid catalysts. For example, an allyl-blocked carboxylic acid can be deprotected with a palladium(0)-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking or protecting groups include, for example:

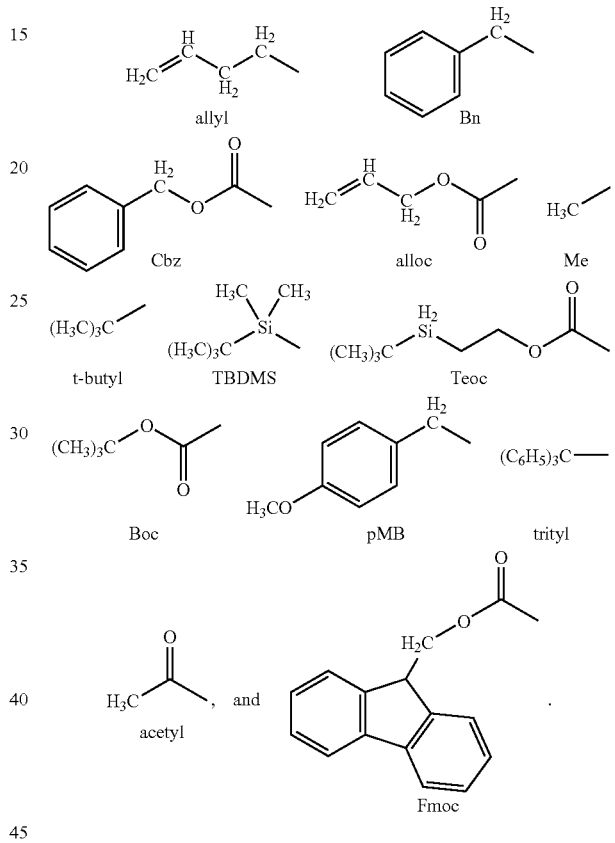

III. Methods of Inhibiting Kinases

In another aspect, the present invention provides methods of modulating protein kinase activity using the bicyclic pyrazolo kinase modulators of the present invention. The term "modulating kinase activity," as used herein, means that the activity of the protein kinase is increased or decreased when contacted with a bicyclic pyrazolo kinase modulator of the present invention relative to the activity in the absence of the bicyclic pyrazolo kinase modulator. Therefore, the present invention provides a method of modulating protein kinase activity by contacting the protein kinase with a bicyclic pyrazolo kinase modulator of the present invention.

In an exemplary embodiment, the bicyclic pyrazolo kinase modulator inhibits kinase activity. The term "inhibit," as used herein in reference to kinase activity, means that the kinase activity is decreased when contacted with a bicyclic pyrazolo kinase modulator relative to the activity in the absence of the bicyclic pyrazolo kinase modulator. Therefore, the present invention further provides a method of inhibiting protein kinase activity by contacting the protein kinase with a bicyclic pyrazolo kinase modulator of the present invention.

In certain embodiments, the protein kinase is a protein tyrosine kinase. A protein tyrosine kinase, as used herein, refers to an enzyme that catalyzes the phosphorylation of tyrosine residues in proteins with a phosphate donors (e.g. a nucleotide phosphate donor such as ATP). Protein tyrosine kinases include, for example, Abelson tyrosine kinases ("Abl") (e.g. c-Abl and v-Abl), Ron receptor tyrosine kinases ("RON"), Met receptor tyrosine kinases ("MET"), Fms-like tyrosine kinases ("FLT") (e.g. FLT3), src-family tyrosine kinases (e.g. lyn, CSK), and p21-activated kinase-4 ("PAK"), FLT3, aurora-A kinases, B-lymphoid tyrosine kinases ("Blk"), cyclin-dependent kinases ("CDK") (e.g. CDK1 and CDK5), src-family related protein tyrosine kinases (e.g. Fyn kinase), glycogen synthase kinases ("GSK") (e.g. GSK3α and GSK3β), lymphocyte protein tyrosine kinases ("Lck"), ribosomal S6 kinases (e.g. Rsk1, Rsk2, and Rsk3), sperm tyrosine kinases (e.g. Yes), and subtypes and homologs thereof exhibiting tyrosine kinase activity. In certain embodiments, the protein tyrosine kinase is Abl, RON, MET, PAK, or FLT3. In other embodiments, the protein tyrosine kinase is a FLT3 or Abl family member.

In another embodiment, the kinase is a mutant kinase, such as a mutant Abl kinase or FLT3 kinase. Useful mutant Abl kinases include, for example, Bcr-Abl and Abl kinases having one of more of the following mutations: Glu255Lys, Thr315Ile, Tyr293Phe, or Met351Thr. In some embodiments, the mutant Abl kinase has a Y393F mutation or a T315I mutation. In another exemplary embodiment, the mutant Abl kinase has a Thr315Ile mutation.

In some embodiments, the kinase is homologous to a known kinase (also referred to herein as a "homologous kinase"). Compounds and compositions useful for inhibiting the biological activity of homologous kinases may be initially screened, for example, in binding assays. Homologous enzymes comprise an amino acid sequence of the same length that is at least 50%, at least 60%, at least 70%, at least 80%, or at least 90% identical to the amino acid sequence of full length known kinase, or 70%, 80%, or 90% homology to the known kinase active domains. Homology may be determined using, for example, a PSI BLAST search, such as, but not limited to that described in Altschul, et al., *Nuc. Acids Rec.* 25:3389-3402 (1997). In certain embodiments, at least 50%, or at least 70% of the sequence is aligned in this analysis. Other tools for performing the alignment include, for example, DbClustal and ESPript, which may be used to generate the PostScript version of the alignment. See Thompson et al., *Nucleic Acids Research*, 28:2919-26, 2000; Gouet, et al., *Bioinformatics*, 15:305-08 (1999). Homologs may, for example, have a BLAST E-value of 1×10$^{-6}$ over at least 100 amino acids (Altschul et al., *Nucleic Acids Res.*, 25:3389-402 (1997) with FLT3, Abl, or another known kinase, or any functional domain of FLT3, Abl, or another known kinase.

Homology may also be determined by comparing the active site binding pocket of the enzyme with the active site binding pockets of a known kinase. For example, in homologous enzymes, at least 50%, 60%, 70%, 80%, or 90% of the amino acids of the molecule or homolog have amino acid structural coordinates of a domain comparable in size to the kinase domain that have a root mean square deviation of the alpha carbon atoms of up to about 1.5 Å, about 1.25 Å, about 1 Å, about 0.75 Å, about 0.5 Å, and or about 0.25 Å.

The compounds and compositions of the present invention are useful for inhibiting kinase activity and also for inhibiting other enzymes that bind ATP. They are thus useful for the treatment of diseases and disorders that may be alleviated by inhibiting such ATP-binding enzyme activity. Methods of determining such ATP binding enzymes include those known to those of skill in the art, those discussed herein relating to selecting homologous enzymes, and by the use of the database PROSITE, where enzymes containing signatures, sequence patterns, motifs, or profiles of protein families or domains may be identified.

The compounds of the present invention, and their derivatives, may also be used as kinase-binding agents. As binding agents, such compounds and derivatives may be bound to a stable resin as a tethered substrate for affinity chromatography applications. The compounds of this invention, and their derivatives, may also be modified (e.g., radiolabelled or affinity labelled, etc.) in order to utilize them in the investigation of enzyme or polypeptide characterization, structure, and/or function.

In an exemplary embodiment, the bicyclic pyrazolo kinase modulator of the present invention is a kinase inhibitor. In some embodiments, the kinase inhibitor has an IC$_{50}$ of inhibition constant (K$_i$) of less than 1 micromolar. In another embodiment, the kinase inhibitor has an IC$_{50}$ or inhibition constant (K$_i$) of less than 500 micromolar. In another embodiment, the kinase inhibitor has an IC$_{50}$ or of less than 10 micromolar. In another embodiment, the kinase inhibitor has an IC$_{50}$ or K$_i$ of less than 1 micromolar. In another embodiment, the kinase inhibitor has an IC$_{50}$ or K$_i$ of less than 500 nanomolar. In another embodiment, the kinase inhibitor has an IC$_{50}$ or K$_i$ of less than 10 nanomolar. In another embodiment, the kinase inhibitor has an IC$_{50}$ or K$_i$ of less than 1 nanomolar.

IV. Methods of Treatment

In another aspect, the present invention provides methods of treating a disease mediated by kinase activity (kinase-mediated disease or disorder) in an organism (e.g. mammals, such as humans). By "kinase-mediated" or "kinase-associated" diseases is meant diseases in which the disease or symptom can be alleviated by inhibiting kinase activity (e.g. where the kinase is involved in signaling, mediation, modulation, or regulation of the disease process). By "diseases" is meant diseases, or disease symptoms.

Examples of kinase associated diseases include cancer (e.g. leukemia, tumors, and metastases), allergy, asthma, inflammation (e.g. inflammatory airways disease), obstructive airways disease, autoimmune diseases, metabolic diseases, infection (e.g. bacterial, viral, yeast, fungal), CNS diseases, brain tumors, degenerative neural diseases, cardiovascular diseases, and diseases associated with angiogenesis, neovascularization, and vasculogenesis. In an exemplary embodiment, the compounds are useful for treating cancer, including leukemia, and other diseases or disorders involving abnormal cell proliferation, myeloproliferative disorders, hematological disorders, asthma, inflammatory diseases or obesity.

More specific examples of cancers treated with the compounds of the present invention include breast cancer, lung cancer, melanoma, colorectal cancer, bladder cancer, ovarian cancer, prostate cancer, renal cancer, squamous cell cancer, glioblastoma, pancreatic cancer, Kaposi's sarcoma, multiple myeloma, and leukemia (e.g. myeloid, chronic myeloid, acute lymphoblastic, chronic lymphoblastic, Hodgkins, and other leukemias and hematological cancers).

Other specific examples of diseases or disorders for which treatment by the compounds or compositions of the invention are useful for treatment or prevention include, but are not limited to transplant rejection (for example, kidney, liver, heart, lung, islet cells, pancreas, bone marrow, cornea, small bowel, skin allografts or xenografts and other transplants), graft vs. host disease, osteoarthritis, rheumatoid arthritis, multiple sclerosis, diabetes, diabetic retinopathy, inflammatory bowel disease (for example, Crohn's disease, ulcerative colitis, and other bowel diseases), renal disease, cachexia, septic shock, lupus, myasthenia gravis, psoriasis, dermatitis, eczema, seborrhea, Alzheimer's disease, Parkinson's disease, stem cell protection during chemotherapy, ex vivo selection or ex vivo purging for autologous or allogeneic bone marrow transplantation, ocular disease, retinopathies (for example, macular degeneration, diabetic retinopathy, and other retinopathies), corneal disease, glaucoma, infections (for example bacterial, viral, or fungal), heart disease, including, but not limited to, restenosis.

V. Assays

The compounds of the present invention may be easily assayed to determine their ability to modulate protein kinases, bind protein kinases, and/or prevent cell growth or proliferation. Some examples of useful assays are presented below.

A. Kinase Inhibition and Binding Assays

Inhibition of various kinases is measured by methods known to those of ordinary skill in the art, such as the various methods presented herein, and those discussed in the Upstate KinaseProfiler Assay Protocols June 2003 publication.

For example, where in vitro assays are performed, the kinase is typically diluted to the appropriate concentration to form a kinase solution. A kinase substrate and phosphate donor, such as ATP, is added to the kinase solution. The kinase is allowed to transfer a phosphate to the kinase substrate to form a phosphorylated substrate. The formation of a phosphorylated substrate may be detected directly by any appropriate means, such as radioactivity (e.g. [$\gamma\gamma$-$^{32}$P-ATP]), or the use of detectable secondary antibodies (e.g. ELISA). Alternatively, the formation of a phosphorylated substrate may be detected using any appropriate technique, such as the detection of ATP concentration (e.g. Kinase-Glo® assay system (Promega)). Kinase inhibitors are identified by detecting the formation of a phosphorylated substrate in the presence and absence of a test compound (see Examples section below).

The ability of the compound to inhibit a kinase in a cell may also be assayed using methods well known in the art. For example, cells containing a kinase may be contacted with an activating agent (such as a growth factor) that activates the kinase. The amount of intracellular phosphorylated substrate formed in the absence and the presence of the test compound may be determined by lysing the cells and detecting the presence phosphorylated substrate by any appropriate method (e.g. ELISA). Where the amount of phosphorylated substrate produced in the presence of the test compound is decreased relative to the amount produced in the absence of the test compound, kinase inhibition is indicated. More detailed cellular kinase assays are discussed in the Examples section below.

To measure the binding of a compound to a kinase, any method known to those of ordinary skill in the art may be used. For example, a test kit manufactured by Discoverx (Fremont, Calif.), ED—Staurosporine NSIP™ Enzyme Binding Assay Kit (see U.S. Pat. No. 5,643,734) may be used. Kinase activity may also be assayed as in U.S. Pat. No. 6,589,950, issued Jul. 8, 2003.

Suitable kinase inhibitors may be selected from the compounds of the invention through protein crystallographic screening, as disclosed in, for example Antonysamy, et al., PCT Publication No. WO03087816A1, which is incorporate herein by reference in its entirety for all purposes.

The compounds of the present invention may be computationally screened to assay and visualize their ability to bind to and/or inhibit various kinases. The structure may be computationally screened with a plurality of compounds of the present invention to determine their ability to bind to a kinase at various sites. Such compounds can be used as targets or leads in medicinal chemistry efforts to identify, for example, inhibitors of potential therapeutic importance (Travis, *Science*, 262:1374, 1993). The three dimensional structures of such compounds may be superimposed on a three dimensional representation of kinases or an active site or binding pocket thereof to assess whether the compound fits spatially into the representation and hence the protein. In this screening, the quality of fit of such entities or compounds to the binding pocket may be judged either by shape complementarity or by estimated interaction energy (Meng, et al., *J. Comp. Chem.* 13:505-24, 1992).

The screening of compounds of the present invention that bind to and/or modulate kinases (e.g. inhibit or activate kinases) according to this invention generally involves consideration of two factors. First, the compound must be capable of physically and structurally associating, either covalently or non-covalently with kinases. For example, covalent interactions may be important for designing irreversible or suicide inhibitors of a protein. Non-covalent molecular interactions important in the association of kinases with the compound include hydrogen bonding, ionic interactions, van der Waals, and hydrophobic interactions. Second, the compound must be able to assume a conformation and orientation in relation to the binding pocket, that allows it to associate with kinases. Although certain portions of the compound will not directly participate in this association with kinases, those portions may still influence the overall conformation of the molecule and may have a significant impact on potency. Conformational requirements include the overall three-dimensional structure and orientation of the chemical group or compound in relation to all or a portion of the binding pocket, or the spacing between functional groups of a compound comprising several chemical groups that directly interact with kinases.

Docking programs described herein, such as, for example, DOCK, or GOLD, are used to identify compounds that bind to the active site and/or binding pocket. Compounds may be screened against more than one binding pocket of the protein structure, or more than one set of coordinates for the same protein, taking into account different molecular dynamic conformations of the protein. Consensus scoring may then be used to identify the compounds that are the best fit for the protein (Charifson, P. S. et al., *J. Med. Chem.* 42: 5100-9 (1999)). Data obtained from more than one protein molecule structure may also be scored according to the methods described in Klingler et al., U.S. Utility Application, filed May 3, 2002, entitled "Computer Systems and Methods for Virtual Screening of Compounds." Compounds having the best fit are then obtained from the producer of the chemical library, or synthesized, and used in binding assays and bioassays.

Computer modeling techniques may be used to assess the potential modulating or binding effect of a chemical compound on kinases. If computer modeling indicates a strong interaction, the molecule may then be synthesized and tested for its ability to bind to kinases and affect (by inhibiting or activating) its activity.

Modulating or other binding compounds of kinases may be computationally evaluated by means of a series of steps in which chemical groups or fragments are screened and selected for their ability to associate with the individual binding pockets or other areas of kinases. This process may begin by visual inspection of, for example, the active site on the computer screen based on the kinases coordinates. Selected fragments or chemical groups may then be positioned in a variety of orientations, or docked, within an individual binding pocket of kinases (Blaney, J. M. and Dixon, J. S., *Perspectives in Drug Discovery and Design,* 1:301, 1993). Manual docking may be accomplished using software such as Insight II (Accelrys, San Diego, Calif.) MOE (Chemical Computing Group, Inc., Montreal, Quebec, Canada); and SYBYL (Tripos, Inc., St. Louis, Mo., 1992), followed by energy minimization and/or molecular dynamics with standard molecular mechanics force fields, such as CHARMM (Brooks, et al., *J. Comp. Chem.* 4:187-217, 1983), AMBER (Weiner, et al., *J. Am. Chem. Soc.* 106: 765-84, 1984) and $C^2$ MMFF (Merck Molecular Force Field; Accelrys, San Diego, Calif.). More automated docking may be accomplished by using programs such as DOCK (Kuntz et al., *J. Mol. Biol.,* 161:269-88, 1982; DOCK is available from University of California, San Francisco, Calif.); AUTODOCK (Goodsell & Olsen, Proteins: Structure, Function, and Genetics 8:195-202, 1990; AUTODOCK is available from Scripps Research Institute, La Jolla, Calif.); GOLD (Cambridge Crystallographic Data Centre (CCDC); Jones et al., *J. Mol. Biol.* 245: 43-53, 1995); and FLEXX (Tripos, St. Louis, Mo.; Rarey, M., et al., *J. Mol. Biol.* 261:470-89, 1996). Other appropriate programs are described in, for example, Halperin, et al.

During selection of compounds by the above methods, the efficiency with which that compound may bind to kinases may be tested and optimized by computational evaluation. For example, a compound that has been designed or selected to function as a kinases inhibitor may occupy a volume not overlapping the volume occupied by the active site residues when the native substrate is bound, however, those of ordinary skill in the art will recognize that there is some flexibility, allowing for rearrangement of the main chains and the side chains. In addition, one of ordinary skill may design compounds that could exploit protein rearrangement upon binding, such as, for example, resulting in an induced fit. An effective kinase inhibitor may demonstrate a relatively small difference in energy between its bound and free states (i.e., it must have a small deformation energy of binding and/or low conformational strain upon binding). Thus, the most efficient kinase inhibitors should, for example, be designed with a deformation energy of binding of not greater than 10 kcal/mol, not greater than 7 kcal/mol, not greater than 5 kcal/mol, or not greater than 2 kcal/mol. Kinase inhibitors may interact with the protein in more than one conformation that is similar in overall binding energy. In those cases, the deformation energy of binding is taken to be the difference between the energy of the free compound and the average energy of the conformations observed when the inhibitor binds to the enzyme.

Specific computer software is available in the art to evaluate compound deformation energy and electrostatic interaction. Examples of programs designed for such uses include: Gaussian 94, revision C (Frisch, Gaussian, Inc., Pittsburgh, Pa. ©1995); AMBER, version 7. (Kollman, University of California at San Francisco, ©2002); QUANTA/CHARMM (Accelrys, Inc., San Diego, Calif., ©1995); Insight II/Discover (Accelrys, Inc., San Diego, Calif., ©1995); DelPhi (Accelrys, Inc., San Diego, Calif., ©1995); and AMSOL (University of Minnesota) (Quantum Chemistry Program Exchange, Indiana University). These programs may be implemented, for instance, using a computer workstation, as are well known in the art, for example, a LINUX, SGI or Sun workstation. Other hardware systems and software packages will be known to those skilled in the art.

Those of ordinary skill in the art may express kinase protein using methods known in the art, and the methods disclosed herein. The native and mutated kinase polypeptides described herein may be chemically synthesized in whole or part using techniques that are well known in the art (see, e.g., Creighton, Proteins: Structures and Molecular Principles, W.H. Freeman & Co., NY, 1983).

Gene expression systems may be used for the synthesis of native and mutated polypeptides. Expression vectors containing the native or mutated polypeptide coding sequence and appropriate transcriptional/translational control signals, that are known to those skilled in the art may be constructed. These methods include in vitro recombinant DNA techniques, synthetic techniques and in vivo recombination/genetic recombination. See, for example, the techniques described in Sambrook et al., Molecular Cloning: A Laboratory Manual, Cold Spring Harbor Laboratory, NY, 2001, and Ausubel et al., Current Protocols in Molecular Biology, Greene Publishing Associates and Wiley Interscience, NY, 1989.

Host-expression vector systems may be used to express kinase. These include, but are not limited to, microorganisms such as bacteria transformed with recombinant bacteriophage DNA, plasmid DNA or cosmid DNA expression vectors containing the coding sequence; yeast transformed with recombinant yeast expression vectors containing the coding sequence; insect cell systems infected with recombinant virus expression vectors (e.g., baculovirus) containing the coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the coding sequence; or animal cell systems. The protein may also be expressed in human gene therapy systems, including, for example, expressing the protein to augment the amount of the protein in an individual, or to express an engineered therapeutic protein. The expression elements of these systems vary in their strength and specificities.

Specifically designed vectors allow the shuttling of DNA between hosts such as bacteria-yeast or bacteria-animal cells. An appropriately constructed expression vector may contain: an origin of replication for autonomous replication in host cells, one or more selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one that causes mRNAs to be initiated at high frequency.

The expression vector may also comprise various elements that affect transcription and translation, including, for example, constitutive and inducible promoters. These elements are often host and/or vector dependent. For example, when cloning in bacterial systems, inducible promoters such as the T7 promoter, pL of bacteriophage λ, plac, ptrp, ptac (ptrp-lac hybrid promoter) and the like may be used; when cloning in insect cell systems, promoters such as the baculovirus polyhedrin promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, mammalian promoters (e.g., metallothionein promoter) or mammalian viral promoters, (e.g., adenovirus late promoter; vaccinia virus 7.5K promoter; SV40 promoter; bovine papilloma virus promoter; and Epstein-Barr virus promoter) may be used.

Various methods may be used to introduce the vector into host cells, for example, transformation, transfection, infection, protoplast fusion, and electroporation. The expression vector-containing cells are clonally propagated and individually analyzed to determine whether they produce the appropriate polypeptides. Various selection methods, including, for example, antibiotic resistance, may be used to identify host cells that have been transformed. Identification of polypeptide expressing host cell clones may be done by several means, including but not limited to immunological reactivity with anti- kinase antibodies, and the presence of host cell-associated activity.

Expression of cDNA may also be performed using in vitro produced synthetic mRNA. Synthetic MRNA can be efficiently translated in various cell-free systems, including but not limited to wheat germ extracts and reticulocyte extracts, as well as efficiently translated in cell-based systems, including, but not limited, to microinjection into frog oocytes.

To determine the cDNA sequence(s) that yields optimal levels of activity and/or protein, modified cDNA molecules are constructed. A non-limiting example of a modified cDNA is where the codon usage in the cDNA has been optimized for the host cell in which the cDNA will be expressed. Host cells are transformed with the cDNA molecules and the levels of kinase RNA and/or protein are measured.

Levels of kinase protein in host cells are quantitated by a variety of methods such as immunoaffinity and/or ligand affinity techniques, kinase-specific affinity beads or specific antibodies are used to isolate 35S-methionine labeled or unlabeled protein. Labeled or unlabeled protein is analyzed by SDS-PAGE. Unlabeled protein is detected by Western blotting, ELISA or RIA employing specific antibodies.

Following expression of kinase in a recombinant host cell, polypeptides may be recovered to provide the protein in active form. Several purification procedures are available and suitable for use. Recombinant kinase kinase may be purified from cell lysates or from conditioned culture media, by various combinations of, or individual application of, fractionation, or chromatography steps that are known in the art.

In addition, recombinant kinase can be separated from other cellular proteins by use of an immuno-affinity column made with monoclonal or polyclonal antibodies specific for full length nascent protein or polypeptide fragments thereof. Other affinity based purification techniques known in the art may also be used.

Alternatively, the polypeptides may be recovered from a host cell in an unfolded, inactive form, e.g., from inclusion bodies of bacteria. Proteins recovered in this form may be solubilized using a denaturant, e.g., guanidinium hydrochloride, and then refolded into an active form using methods known to those skilled in the art, such as dialysis.

B. Cell Growth Assays

A variety of cell growth assays are known in the art and are useful in identifying bicyclic pyrazolo compounds (i.e. "test compounds") capable of inhibiting (e.g. reducing) cell growth and/or proliferation.

For example, a variety of cells are known to require specific kinases for growth and/or proliferation. The ability of such a cell to grow in the presence of a test compound may be assessed and compared to the growth in the absence of the test compound thereby identifying the anti-proliferative properties of the test compound. One common method of this type is to measure the degree of incorporation of label, such as tritiated thymidine, into the DNA of dividing cells. Alternatively, inhibition of cell proliferation may be assayed by determining the total metabolic activity of cells with a surrogate marker that correlates with cell number. Cells may be treated with a metabolic indicator in the presence and absence of the test compound. Viable cells metabolize the metabolic indicator thereby forming a detectable metabolic product. Where detectable metabolic product levels are decreased in the presence of the test compound relative to the absence of the test compound, inhibition of cell growth and/or proliferation is indicated. Exemplary metabolic indicators include, for example tetrazolium salts and AlamorBlue® (see Examples section below).

An assay for kinases that stimulate cell migration is the scratch assay. This assay is used to evaluate inhibitors of kinases by mimicking events such as wound healing. In one variant of this assay used to test MET inhibitors, a confluent monolayer of cells is allowed to form on a cell plate. After formation of the monolayer, a linear wound on the monolayer is generated by mechanically scraping the monolayer thereby forming a cell-free channel. A growth factor required by the kinase for cell growth is added in the presence or absence of the test compound. The closure of the channel in the presence of the test compound indicates a failure of the test compound to inhibit the kinase thereby allowing cell migration and growth to close the channel. Conversely, the presence of the channel after adding the test compound indicates that test compound inhibited the kinase thereby preventing cell growth. The selection of the appropriate cells, growth conditions, and growth factors are well within the abilities of one skilled in the art (see Examples section below).

VI. Pharmaceutical Compositions and Administration

In another aspect, the present invention provides a pharmaceutical composition including a bicyclic pyrazolo kinase modulator in admixture with a pharmaceutically acceptable excipient. One of skill in the art will recognize that the pharmaceutical compositions include the pharmaceutically acceptable salts of the bicyclic pyrazolo kinase modulators described above.

In therapeutic and/or diagnostic applications, the compounds of the invention can be formulated for a variety of modes of administration, including systemic and topical or localized administration. Techniques and formulations generally may be found in Remington: The Science and Practice of Pharmacy ($20^{th}$ ed.) Lippincott, Williams & Wilkins (2000).

The compounds according to the invention are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A most preferable dosage is 10 to 30 mg per day. The exact dosage will depend upon the route of administration, the form in which the compound is administered, the subject to be treated, the body weight of the subject to be treated, and the preference and experience of the attending physician.

Pharmaceutically acceptable salts are generally well known to those of ordinary skill in the art, and may include, by way of example but not limitation, acetate, benzenesulfonate, besylate, benzoate, bicarbonate, bitartrate, bromide, calcium edetate, camsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy ($20^{th}$ ed.) Lippincott, Williams & Wilkins (2000). Preferred pharmaceutically acceptable salts include, for example, acetate, benzoate, bromide, carbonate, citrate, gluconate, hydrobromide, hydrochloride, maleate, mesylate, napsylate, pamoate (embonate), phosphate, salicylate, succinate, sulfate, or tartrate.

Depending on the specific conditions being treated, such agents may be formulated into liquid or solid dosage forms and administered systemically or locally. The agents may be delivered, for example, in a timed- or sustained- low release form as is known to those skilled in the art. Techniques for formulation and administration may be found in Remington: The Science and Practice of Pharmacy (20$^{th}$ ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intra -sternal, intrasynovial, intra-hepatic, intralesional, intracranial, intraperitoneal, intranasal, or intraocular injections or other modes of delivery.

For injection, the agents of the invention may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

For nasal or inhalation delivery, the agents of the invention may also be formulated by methods known to those of skill in the art, and may include, for example, but not limited to, examples of solubilizing, diluting, or dispersing substances such as, saline, preservatives, such as benzyl alcohol, absorption promoters, and fluorocarbons.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross- linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Depending upon the particular condition, or disease state, to be treated or prevented, additional therapeutic agents, which are normally administered to treat or prevent that condition, may be administered together with the inhibitors of this invention. For example, chemotherapeutic agents or other anti-proliferative agents may be combined with the inhibitors of this invention to treat proliferative diseases and cancer. Examples of known chemotherapeutic agents include, but are not limited to, adriamycin, dexamethasone, vincristine, cyclophosphamide, fluorouracil, topotecan, taxol, interferons, and platinum derivatives.

Other examples of agents the inhibitors of this invention may also be combined with include, without limitation, anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and antiviral agents; agents for treating blood disorders such as corticosteroids, anti-leukemic agents, and growth factors; agents for treating diabetes such as insulin, insulin analogues, alpha glucosidase inhibitors, biguanides, and insulin sensitizers; and agents for treating immunodeficiency disorders such as gamma globulin.

These additional agents may be administered separately, as part of a multiple dosage regimen, from the inhibitor-containing composition. Alternatively, these agents may be part of a single dosage form, mixed together with the inhibitor in a single composition.

The present invention is not to be limited in scope by the exemplified embodiments, which are intended as illustrations of single aspects of the invention. Indeed, various modifications of the invention in addition to those described herein will become apparent to those having skill in the art from the foregoing description. Such modifications are intended to fall within the scope of the invention. Moreover, any one or more features of any embodiment of the invention may be combined with any one or more other features of any other embodiment of the invention, without departing from the scope of the invention. For example, the bicyclic pyrazolo kinase modulators described in the Bicyclic Pyrazolo Kinase Modulators section are equally applicable to the methods of treatment and methods of inhibiting kinases described herein. References cited throughout this application are examples of the level of skill in the art and are hereby incorporated by reference herein in their entirety for all purposes, whether previously specifically incorporated or not.

EXAMPLES

The following examples are offered to illustrate, but not to limit the claimed invention. The preparation of embodiments of the present invention is described in the following examples. Those of ordinary skill in the art will understand that the chemical reactions and synthesis methods provided may be modified to prepare many of the other compounds of the present invention. Where compounds of the present invention have not been exemplified, those of ordinary skill in the art will recognize that these compounds may be prepared by modifying synthesis methods presented herein, and by using synthesis methods known in the art.

Example 1

Synthesis of Compounds

Synthesis of 3-phenyl-1H-pyrazolo[3,4-d]thiazol-5-ylamine

To a stirring solution of 5-amino-3-phenylpyrazole (5 g, 31.4 mmol) in dioxane (100 mL) was added MgO (1.27 g, 31.4 mmol) and a saturated aqueous solution of sodium bicarbonate (100 mL). The heterogeneous mixture was stirred for 30 min, then thiophosgene (2.65 mL, 34.6 mmol) was added dropwise, and the reaction mixture was further stirred vigorously for 15 min until completion. Ammonium hydroxide (25 mL) was then added dropwise, and the reaction mixture was stirred for another 20 min. A 10% aqueous solution of citric acid was added to lower the pH to 6, and the mixture was extracted with ethyl acetate (3×). The organic layer was dried over sodium sulfate, filtered, and adsorbed on silica gel. Purification on silica gel with 10-80% ethyl acetate in hexane as eluent provided 6.22 g (91%) of (5-Phenyl-2H-pyrazol-3-yl)-thiourea as a yellow foam.

The yellow foam (6.2 g, 28.4 mmol) was dissolved in AcOH (125 mL) and a 1.5M solution of bromine in AcOH (20.8 mL, 31.2 mmol) was added dropwise over 30 min under vigorous stirring. The resulting heterogeneous mixture was stirred at 80° C. for 2.5 h, then cooled to room temperature, and concentrated in vacuo. The residue was suspended in water and 4N aqueous NaOH was added until pH 7. After extraction with ethyl acetate, the organic layer was adsorbed on silica gel. Purification on silica gel with 0-10% MeOH in $CH_2Cl_2$ as eluent provided 3.26 g of a yellow solid that was further recrystallized from isopropyl alcohol to yield 2.81 g (45%) of pure 3-phenyl-1H-pyrazolo[3,4-d]thiazol-5-ylamine as off-white crystals. $^1$H-NMR ($d_6$-DMSO) δ: 12.8 and 12.9 (2 broad s, 1H, NH+tautomer), 7.60 (broad s, 2H), 7.55 (broad s, 2H, $NH_2$), 7.48 (broad s; 2H), 7.33 (t, 1H); HPLC/MS m/z: 217 [MH]$^+$.

Synthesis of N-(3-thiophen-2-yl-1H-pyrazolo[3,4-d]thiazol-5-yl)-benzamide

To a stirring solution of 5-amino-3-(2-thienyl)pyrazole (500 mg, 3.03 mmol) in THF (10 mL) was added N-bromo-succinimide (592 mg, 3.33 mmol) in one portion. The reaction mixture was stirred at room temperature for 3 h, then the solvent was evaporated and the residue was taken up in ethyl acetate. The organic layer was washed successively with 1M aqueous sodium thiosulfate, twice with a saturated aqueous solution of sodium bicarbonate, and brine, then it was dried over sodium sulfate, filtered, and adsorbed on silica gel. Purification on silica gel with 0-10% MeOH in $CH_2Cl_2$ as eluent provided 686 mg (93%) of 4-bromo-5-thiophen-2-yl-2H-pyrazol-3-ylamine as a dark foam. $^1$H-NMR ($d_6$-DMSO) δ: 11.9 and 12.4 (2 broad s, 1H, NH+tautomer), 7.4-7.65 (m, 2H), 7.05-7.2 (m, 1H), 4.8 and 5.3 (2 broad s, 2H, $NH_2$+ tautomer).

To a stirring solution of 4-bromo-5-thiophen-2-yl-2H-pyrazol-3-ylamine (50 mg, 0.205 mmol) in dioxane (1 mL) was added benzoylisothiocyanate (30 μL, 0.225 mmol) dropwise. The reaction mixture was stirred at 90° C. for 17 h. It was then cooled to room temperature and partitioned between ethyl acetate and a saturated aqueous solution of sodium bicarbonate. The organic layer was washed twice with a saturated aqueous solution of sodium bicarbonate, then with brine, and adsorbed on silica gel. Purification on silica gel with 0-80% ethyl acetate in hexane as eluent provided 54 mg (80%) of N-(3-thiophen-2-yl-1H-pyrazolo[3,4-d]thiazol-5-yl)-benzamide as a beige solid. $^1$H-NMR ($d_6$-DMSO) δ: 13.5 and 13.6 (2 broad s, 1H, NH+tautomer), 12.9 (broad s, 1H, NH), 8.1 (d, 2H), 7.68 and 7.85 (2 dd, 1H, tautomers), 7.66 (t, 1H), 7.58 (t, 2H), 7.34 and 7.53 (2 d, 1H, tautomers), 7.17 and 7.22 (2 t, 1H, tautomers); HPLC/MS m/z: 327 [MH]$^+$.

Synthesis of N-[3-(3-chloro-phenyl)-1H-pyrazolo[3,4-d]thiazol-5-yl]-benzamide

To a stirring solution of 3-(3-chlorophenyl)-3-oxo-propionitrile (2 g, 11.1 mmol) in absolute ethanol (20 mL) was added hydrazine hydrate (3.24 mL, 67 mmol). The reaction mixture was stirred at 80° C. for 15 h, cooled to room temperature, concentrated in vacuo, and absorbed on silica gel. Purification on silica gel with 0-10% MeOH in $CH_2Cl_2$ as eluent provided 1.53 g (70%) of 5-(3-chloro-phenyl)-2H-pyrazol-3-ylamine as a green solid. $^1$H NMR ($d_6$-DMSO) δ: 11.6 and 11.9 (2 broad s, 1H, NH+tautomer), 7.69 (s, 1H), 7.60 (d, 1H), 7.38 (t, 1H), 7.29 (d, 1H), 5.77 (broad s, 1H), 4.98 (broad s, 2H, $NH_2$).

To a stirring solution of 5-(3-chloro-phenyl)-2H-pyrazol-3-ylamine (1.53 g, 7.9 mmol) in THF (32 mL) was added N-bromosuccinimide (1.55 g, 8.7 mmol). The reaction mixture was stirred for 5 h at room temperature, then absorbed on silica gel. Purification on silica gel with 0-10% MeOH in $CH_2Cl_2$ as eluent provided 1.73 g (80%) of 4-bromo-5-(3-chloro-phenyl)-2H-pyrazol-3-ylamine as a brown solid. $^1$H NMR ($d_6$-DMSO) δ: 12.2 and 12.4 (2 broad s, 1H, NH+tautomer), 7.77 (s, 1H), 7.73 (broad s, 1H), 7.48 (broad s, 1H), 7.43 (broad s, 1H), 5.30 (broad s, 1H, NH), 4.82 (broad s, 1H, NH); HPLC/MS m/z: 272 [MH]$^+$.

To a stirring solution of 4-bromo-5-(3-chloro-phenyl)-2H-pyrazol-3-ylamine (50 mg, 0.183 mmol) in dioxane (1 mL) was added benzoyl isothiocyanate (27 μL, 0.202 mmol). The reaction mixture was stirred overnight at 90° C., cooled at room temperature, and partitioned between ethyl acetate and sodium bicarbonate. The organic layer was isolated and absorbed on silica gel. Purification on silica gel with 0-10% MeOH in $CH_2Cl_2$ as eluent provided 10.8 mg (17%) of N-[3-(3-chloro-phenyl)-1H-pyrazolo[3,4-d]thiazol-5-yl]-benzamide as a white solid. $^1$H NMR (d$_6$-DMSO) δ: 13.70 and 13.72 (2 broad s, 1H, NH+tautomer), 12.9 (broad s, 1H, NH), 8.12 (d, 2H), 7.81 and 7.85 (2 broad s, 1H, tautomers), 7.65-7.74 (m, 2H), 7.54-7.62 (m, 3H), 7.45 (m, 1H); HPLC/MS m/z: 355 [MH]$^+$.

Synthesis of N-(3-pyridin-2-yl-1H-pyrazolo[3,4-d]thiazol-5-yl)-benzamide

Acetonitrile (0.87 mL) was added dropwise to a mixture of n-butyl lithium (2.5 M in hexanes, 6.64 mL) and THF (15 mL) at −78° C. The mixture was left to stir for 1 h. A solution of ethyl picolinate (2.7 g, 15.1 mmol) in THF (15 mL) was added dropwise, maintaining the temperature at −78° C. Stirring was continued at −78° C. for an additional 2 h. The mixture was allowed to warm up to room temperature and stirring was continued for an additional 90 min. The reaction was quenched by addition of water (20 mL). The pH of the solution was adjusted to 4 with a 1 N aqueous solution of HCl and the aqueous solution extracted with EtOAc. The combined organic extracts were dried over MgSO$_4$, filtered, and the solvent removed under reduced pressure. The crude product was dissolved in AcOH (8 mL) and Br$_2$ (0.22 mL, 4.6 mmol) was added dropwise. The mixture was stirred over the course of one hour. Filtration followed by washing with Et$_2$O afforded 500 mg (10%) of 4-bromo-5-pyridin-2-yl-2H-pyrazol-3-ylamine hydrobromide salt as a dark solid. $^1$H NMR (d$_6$-DMSO) δ: 9.12 (s, 1H), 8.82 (m, 1H), 8.76 (m, 1H), 8.04 (m, 1H); HPLC/MS m/z: 239 [MH]$^+$.

A mixture of 4-bromo-5-pyridin-2-yl-2H-pyrazol-3-ylamine hydrobromide salt (300 mg, 0.94 mmol), benzoyl isothiocyanate (0.15 mL, 1.12 mmol), pyridine (0.24 mL, 2.97 mmol), 1,4-dioxane (2 mL), and DMSO (2 mL) was heated at 95° C. overnight. The mixture was added to an excess of water, and the resulting precipitate was filtered, and recrystallized from EtOH to afford 190 mg (63%) of N-(3-pyridin-2-yl-1H-pyrazolo[3,4-d]thiazol-5-yl)-benzamide as an off-white solid. $^1$H NMR (d$_6$-DMSO) δ: 8.85 (s, 1H), 8.02 (m, 4H), 7.51 (m, 3H), 7.21 (m, 1H); HPLC/MS m/z: 322 [MH]$^+$.

Synthesis of N-(3-phenyl-1H-pyrazolo[3,4-d]thiazol-5-yl)-isonicotinamide

To a stirring solution of 3-phenyl-1H-pyrazolo[3,4-d]thiazol-5-ylamine (20 mg, 0.092 mmol) and pyridine (52 μL, 0.65 mmol) in THF (0.5 mL) was added isonicotinoyl chloride hydrochloride (82 mg, 0.46 mmol). The reaction mixture was stirred at 70° C. for 22 h, then cooled to room temperature and treated with MeOH (1 mL) and a 4N aqueous solution of NaOH (0.25 mL). The reaction mixture was further stirred at room temperature for 4 h, then a 1N aqueous solution of HCl was added to adjust the pH to 7, and the mixture was extracted with 10% MeOH in CH$_2$Cl$_2$ (3×). Purification on silica gel with 0-10% MeOH in CH$_2$Cl$_2$ as eluent provided 12.5 mg (42%) of N-(3-phenyl-1H-pyrazolo[3,4-d]thiazol-5-yl)-isonicotinamide as a beige solid. $^1$H-NMR (d$_6$-DMSO) δ: 13.5 and 13.7 (2 broad s, 1H, NH+tautomer), 13.2 (broad s, 1H, NH), 8.83 (d, 2H), 7.99 (d, 2H), 7.80 (m, 2H, tautomers), 7.55 (m, 2H, tautomers), 7.40 (m, 1H, tautomers; HPLC/MS m/z: 322 [MH]$^+$.

Synthesis of furan-2-carboxylic acid (3-tert-butyl-1H-pyrazolo[3,4-d]thiazol-5-yl)-amide To a stirring solution of 3-tert-Butyl-1H-pyrazolo[3,4-d]thiazol-5-ylamine (30 mg, 0.153 mmol) and pyridine (74 μL, 0.92 mmol), or alternatively PS-DMAP (Argonaut resin, 6 equiv.), in THF (0.75 mL) was added furan-carbonyl chloride (75 μL, 0.76 mmol). The reaction mixture was stirred at 70° C. for 23 h, then cooled to room temperature and treated with THF (1 mL) and PS-trisamine (Argonaut resin, 20 equiv.) for 2 h. The resin was filtered, washed with DMF and the solvent was evaporated. The residue was treated with MeOH (1 mL) and a 4N aqueous solution of NaOH (0.25 mL) and the solution was stirred at room temperature for 2 h. The reaction mixture was neutralized to pH 7 with a 1N aqueous solution of HCl and extracted with ethyl acetate (3×). Purification on silica gel with 0-10% MeOH in CH$_2$Cl$_2$ as eluent provided 36 mg (82%) of furan-2-carboxylic acid (3-tert-butyl-1H-pyrazolo[3,4-d]thiazol-5-yl)-amide as an off-white solid. $^1$H-NMR (d$_6$-DMSO) δ: 12.8 (broad s, 1H, NH), 12.7 (broad s, 1H, NH), 8.03 (d, 1H), 7.69 (broad s, 1H), 6.74 (dd, 1H), 1.36 (s, 9H); HPLC/MS m/z: 291 [MH]$^+$.

Synthesis of 2-(2-methoxy-ethoxy)-N-(3-phenyl-1H-pyrazolo[3,4-d]thiazol-5-yl)-acetamide To a vial charged with 3-phenyl-1H-pyrazolo[3,4-d]thiazol-5-ylamine (30 mg, 0.139 mmol), PS-DMAP (Argonaut resin, 6 equiv.), and a stirring bar was added THF (2 mL) and 2-(2-methoxyethoxy)acetyl chloride (106 μL, ca. 5 equiv.). The reaction mixture was stirred at 70° C. for 24 h, then cooled to room temperature and treated with PS-trisamine (Argonaut resin, 20 equiv.) for 1.5 h. The resin was filtered, washed with THF and the solvent was evaporated. The residue was treated with a (5:1:1) mixture of THF/H$_2$O/Et$_3$N (2 mL) at 50° C. for 24 h, then the solution was directly adsorbed on silica gel. Purification on silica gel with 0-10% MeOH in CH$_2$Cl$_2$ as eluent provided 30 mg (65%) of 2-(2-methoxy-ethoxy)-N-(3-phenyl-1H-pyrazolo[3,4-d]thiazol-5-yl)-acetamide as a white solid. $^1$H-NMR (d$_6$-DMSO) δ: 13.5 and 13.6 (2 broad s, 1H, NH+tautomer), 12.2 (broad s, 1H, NH), 7.74 (m, 2H, tautomers), 7.54 (m, 2H, tautomers), 7.38 (m, 1H, tautomers), 4.28 (s, 2H), 3.68 (t, 2H), 3.51 (t, 2H), 3.29 (s, 3H); HPLC/MS m/z: 333 [MH]$^+$.

Synthesis of furan-2-carboxylic acid (3-pyridin-2-yl-1H-pyrazolo[3,4-d]thiazol-5-yl)-amide A mixture of 4-bromo-5-pyridin-2-yl-2H-pyrazol-3-ylamine hydrobromide salt (193 mg, 0.60 mmol), furan-2-carbonyl isothiocyanate (0.07 mL), pyridine (0.1 mL), and DMSO (2 mL) was placed in a Smith process vial. The reaction was run in a Personal Chemistry SmithCreator microwave at 160° C. for five minutes. The reaction mixture was then added to an excess of water and the resulting precipitate was filtered. Purification by preparative HPLC afforded 10 mg of furan-2-carboxylic acid (3-pyridin-2-yl-1H-pyrazolo[3,4-d]thiazol-5-yl)-amide as a white solid. $^1$H-NMR (d$_6$-DMSO) δ: 8.60 (dd, 1H), 7.92 (m, 2H), 7.80 (d, 1H), 7.46 (d, 1H), 7.26 (m, 2H), 6.60 (dd, 1H); HPLC/MS m/z: 312 [MH]$^+$.

Synthesis of 2-chloro-4-methyl-thiazole-5-carboxylic acid (3-phenyl-1H-pyrazolo[3,4-d]thiazol-5-yl)-amide To a vial equipped with a teflon cap was added 2-bromo-4-methyl-thiazole-5-carboxylic acid (350 mg, 1.576 mmol), thionyl chloride (3 mL), and DMF (0.02 mL). The reaction mixture was stirred at 85° C. for 3 hours, then the excess of thionyl chloride was evaporated in vacuo, dry toluene was added, and the solvent was evaporated in vacuo. Dry toluene (3 mL) was added to generate a solution of 2-chloro-4-methyl-thiazole-5-carbonyl chloride (ca. 0.52 M) that was used as such in the next step.

To a vial charged with 3-phenyl-1H-pyrazolo[3,4-d]thiazol-5-ylamine (30 mg, 0.139 mmol), PS-DMAP (Argonaut resin, 558 mg, 6 equiv.), and a stirring bar was added THF (2 mL) and 2-chloro-4-methyl-thiazole-5-carbonyl chloride solution in toluene (0.52 M, 1.3 mL, ca. 5 equiv.). The reaction mixture was stirred at 70° C. for 18 hours, then cooled to room temperature and treated with PS-trisamine (Argonaut resin, 674 mg, 20 equiv.) for 2 hours. The resin was filtered, washed with THF and the solvent was evaporated. The resulting crude mixture was treated with MeOH (1 mL) and a 4 N aqueous solution of NaOH (0.25 mL). The reaction mixture was further stirred at room temperature for 2 hours, then a 1 N aqueous solution of HCl was added to adjust the pH to 7, and the mixture was extracted with EtOAc (3×). Purification on silica gel with 0-10% MeOH in $CH_2Cl_2$ as eluent provided 11 mg (21% yield) of 2-chloro-4-methyl-thiazole-5-carboxylic acid (3-phenyl-1H-pyrazolo[3,4-d]thiazol-5-yl)-amide as an off-white solid. $^1$H-NMR (d$_6$-DMSO) δ: 7.75 (d, 2H), 7.54 (t, 2H), 7.39 (t, 1H), 2.65 (s, 3H); HPLC/MS m/z: 376.0 [MH]$^+$.

Synthesis of N-[3-(4-methoxy-phenyl)-1H-pyrazolo [3,4-d] thiazol-5-yl]-acetamide To a solution of 3-(4-methoxyphenyl)-3-oxo-propionitrile (2.0 g, 11.4 mmol) in absolute ethanol (21 mL) was added hydrazine hydrate (3.32 mL, 68.3 mmol). The reaction mixture was stirred at 80° C. for 15 hours, then it was concentrated in vacuo and purified on silica gel with 0-10% MeOH in $CH_2Cl_2$ as eluent to give 2.02 g (97% yield) of 5-amino-3-(4-methoxyphenyl)pyrazole as a white solid. $^1$H NMR (d$_6$-DMSO) δ: 11.69 (s, 1H), 7.55 (d, 2H), 6.92 (d, 2H), 5.66 (s, 1H), 4.62 (broad s, 2H), 3.75 (s, 3H); HPLC/MS m/z: 190.1 [MH]$^+$.

To a solution of 5-amino-3-(4-methoxyphenyl)pyrazole (2.5 g, 13.2 mmol) in THF (50 mL) was added dropwise benzoyl isothiocyanate (1.96 mL, 14.5 mmol). The reaction mixture was stirred at room temperature for 45 minutes, then 4 N aqueous solution of NaOH (10 mL) was added, and the reaction mixture was further stirred at 55° C. for 1 hour. The reaction mixture was cooled to room temperature, neutralized to pH 8 with 1N aqueous HCl, and extracted with EtOAc (3×). The combined organic layers were washed with brine, dried over sodium sulfate, filtered, evaporated, and dried in vacuo to provide 4.28 g of an orange-yellow solid. The solid was dissolved in glacial AcOH (300 mL) and a 1.5 M solution of bromine in AcOH (8.8 mL, 13.2 mmol) was added dropwise under vigorous stirring. The resulting heterogeneous mixture was stirred at room temperature for 1 hour then at 80° C. for 1 hour. The reaction was cooled to room temperature and $Et_2O$ (500 mL) was added. The resulting precipitate was filtered, washed with $Et_2O$, and dried in vacuo to afford 2.93 g (68% yield) of 3-(4-methoxyphenyl)-1H-pyrazolo[3,4-d]thiazol-5-ylamine as a light yellow solid. $^1$H-NMR (d$_6$-DMSO) δ: 7.57 (d, 2H), 7.09 (d, 2H), 3.80 (s, 3H); HPLC/MS m/z: 247.1 [MH]$^+$.

To a vial charged with 3-(4-methoxyphenyl)-1H-pyrazolo [3,4-d]thiazol-5-ylamine (100 mg, 0.306 mmol), PS-DMAP (Argonaut resin, 1.2 g, 6 equiv.), and a stirring bar was added THF (3 mL) and acetyl chloride (110 μL, 1.53 mmol). The reaction mixture was stirred at 70° C. for 1 hour, then cooled to room temperature and treated with PS-trisamine (Argonaut resin, 1.1 g, 20 equiv.) for 1 hour. The resin was filtered, washed with THF and the solvent was evaporated. The resulting crude was suspended in MeOH and treated with hydrazine monohydrate (0.06 mL) for 30 minutes. The precipitate was filtered, and the filtrate was directly purified on silica gel with 0-10% MeOH in $CH_2Cl_2$ as eluent to provide 12.5 mg (14% yield) of N-[3-(4-methoxy-phenyl)-1H-pyrazolo[3,4-d]thiazol-5-yl]-acetamide as an off-white solid. $^1$H-NMR (d$_6$-DMSO) δ: 13.4 (broad s, 1H), 12.3 (broad s, 1H), 7.66 (broad s, 2H), 7.09 (broad s, 2H), 3.80 (s, 3H), 2.18 (s, 3H); HPLC/MS m/z: 289.0 [MH]$^+$.

Synthesis of 2-methoxy-N-(3-phenyl-1H-pyrazolo[3,4-d] thiazol-5-yl)-acetamide

To a vial charged with 3-phenyl-1H-pyrazolo[3,4-d]thiazol-5-ylamine (30 mg, 0.139 mmol), PS-DMAP (Argonaut resin, 0.56 g, 6 equiv.), and a stirring bar was added THF (2 mL) and 2-methoxyacetyl chloride (63 μL, 0.694 mmol). The reaction mixture was stirred at 70° C. for 3.5 hours, then cooled to room temperature and treated with PS-trisamine (Argonaut resin, 0.51 g, 15 equiv.) at 50° C. for 3 hours. The resin was filtered, washed with THF and the solvent was evaporated. Purification on silica gel with 0-10% MeOH in $CH_2Cl_2$ as eluent provided 15 mg (37% yield) of 2-methoxy-N-(3-phenyl-1H-pyrazolo[3,4-d]thiazol-5-yl)-acetamide as a white solid. $^1$H-NMR (d$_6$-DMSO) δ: 13.6 (broad s, 1H), 12.3 (broad s, 1H), 7.73 (broad s, 2H), 7.53 (broad s, 2H), 7.37 (broad s, 1H), 4.20 (s, 2H), 3.37 (s, 3H), 2.18 (s, 3H); HPLC/MS m/z: 289.1 [MH]$^+$.

Synthesis of 5-morpholin-4-ylmethyl-furan-2-carboxylic acid [3-(2-bromo-phenyl)-1H-pyrazolo[3,4-d]thiazol-5-yl]-amide To a solution of ethyl 5-(chloromethyl)-2-furan-carboxylate (0.5 mL, 3.25 mmol) and $Et_3N$ (0.9 mL, 6.5 mmol) in dichloromethane under nitrogen was added morpholine (284 μL, 3.25 mmol) dropwise and a catalytic amount of KI. The reaction mixture was stirred at 45° C. for 24 hours, then it was concentrated in vacuo. The residue was dissolved in EtOAc and the organic layer was washed with water (2×) then brine, dried over sodium sulfate, filtered, concentrated, and dried in vacuo to give 520 mg (67% yield) of 5-morpholin-4-ylmethyl-furan-2-carboxylic acid ethyl ester as a light brown oil. $^1$H-NMR (d$_6$-DMSO) δ: 7.22 (d, 1H), 6.51 (d, 1H), 4.25 (q, 2H), 3.54 (m, 6H), 2.37 (broad s, 4H), 1.27 (t, 3H).

To a solution of 5-morpholin-4-ylmethyl-furan-2-carboxylic acid ethyl ester (510 mg, 2.13 mmol) in MeOH (20 mL) was added Amberlyst A26(OH) (10 g, 21.3 mmol), and the reaction mixture was shaken for 24 hours. The resin was filtered, washed with MeOH, then taken into 1.25 M HCl in MeOH (50 ml). The resin was filtered, washed with MeOH, and the solution was evaporated to dryness to give 421 mg (80% yield) of 5-morpholin-4-ylmethyl-furan-2-carboxylic acid hydrochloride as a foam. $^1$H-NMR (d$_6$-DMSO) δ: 11.54 (broad s, 1H), 7.26 (d, 1H), 6.92 (d, 1H), 4.49 (broad s, 2H), 3.93 (broad s, 2H), 3.74 (broad s, 2H), 3.27 (broad s, 2H), 3.09 (broad s, 2H).

A suspension of 5-morpholin-4-ylmethyl-furan-2-carboxylic acid hydrochloride in thionyl chloride with 2 drops of DMF was refluxed under $N_2$ for 3 hours, then cooled to room temperature. Dry $CH_2Cl_2$ was added and solvents were evaporated in vacuo. The residue was triturated with dry $CH_2Cl_2$, and the resulting solid was filtered, washed with dry $CH_2Cl_2$ and dried in vacuo to give 373 mg (83% yield) of 5-morpholin-4-ylmethyl-furan-2-carbonyl chloride hydrochloride as a white solid. $^1$H-NMR (d$_6$-DMSO) δ: 11.54 (broad s, 1H), 7.26 (d, 1H), 6.92 (d, 1H), 4.49 (s, 2H), 3.94 (m, 2H), 3.74 (m, 2H), 3.28 (m, 2H), 3.09 (broad s, 2H).

To a suspension of NaH (60% dispersion, 1.14 g, 28.4 mmol) in dry THF (50 mL) under $N_2$ was added $CH_3CN$ followed by 2-bromo-benzoic acid methyl ester (2 mL, 14.2 mmol). The reaction mixture was refluxed for 1.5 hour, then cooled to 0° C., quenched with water (1 mL), and concentrated in vacuo. The residue was diluted with water and the aqueous layer was extracted with hexane (2×), then acidified to pH 3-4 with 1N aqueous HCl. The milky aqueous layer was extracted with $CHCl_3$ (3×), the combined organic layers were dried over sodium sulfate, filtered, and concentrated. Purification on silica gel with 0-35% EtOAc in hexane as eluent provided 1.89 g (59 % yield) of 3-(2-bromo-phenyl)-3-oxo-propionitrile as a yellow oil. $^1$H-NMR (d$_6$-DMSO) δ: 11.8 (broad m, 1H, tautomers), 7.73 (broad s, 1H), 7.42 (m, 3H), 4.99 (s, 0.3H, tautomer), 4.64 (s, 0.6H, tautomer); HPLC/MS m/z: 223.9, 225.9 [MH]$^+$.

To a solution of 3-(2-bromo-phenyl)-3-oxo-propionitrile (1.8 g, 8.03 mmol) in absolute EtOH (25 mL) was added hydrazine hydrate (2.3 mL, 48.2 mmol). The reaction mixture was refluxed for 23 hours, then cooled and purified directly on silica gel with 0-10% MeOH in CH$_2$Cl$_2$ as eluent to provide 1.33 g (70% yield) of 5-amino-3-(2-bromophenyl)pyrazole as a sticky oil. $^1$H-NMR (d$_6$-DMSO) δ: 11.7 (broad m, 1H, tautomers), 7.20-7.70 (broad m, 4H), 5.76 (broad m, 1H), 5.03 (broad s, 1H), 4.60 (broad s, 1H); HPLC/MS m/z: 238.0, 240.0 [MH]$^+$.

To a solution of 5-amino-3-(2-bromophenyl)pyrazole (1.3 g, 5.46 mmol) in THF (20 mL) was added dropwise benzoyl isothiocyanate (0.81 mL, 6.0 mmol). The reaction mixture was stirred at room temperature for 3 hours, then 4 N aqueous solution of NaOH (4 mL) was added, and the reaction mixture was further stirred at 50° C. for 2 hours. The reaction mixture was cooled to room temperature, neutralized to pH 7 with a saturated solution of NH$_4$Cl, and extracted with EtOAc (3×). The combined organic layers were directly purified on silica gel with 0-10% MeOH in CH$_2$Cl$_2$ as eluent to provide 1.62 g (quant.) of [5-(2-bromo-phenyl)-2H-pyrazol-3-yl]-thiourea as a yellowish foam. $^1$H-NMR (d$_6$-DMSO) δ: 12.8 (broad s, 1H), 10.4 (broad s, 1H), 8.99 (broad s, 1H), 8.52 (broad s, 1H), 7.76 (d, 1H), 7.50 (m, 2H), 7.36 (t, 1H), 6.24 (broad s, 1H).

To a solution of [5-(2-bromo-phenyl)-2H-pyrazol-3-yl]-thiourea (1.6 g, 5.38 mmol) in glacial AcOH (200 mL) was added a 1.5 M solution of bromine in AcOH (3.59 mL, 5.38 mmol) dropwise under vigorous stirring. The resulting heterogeneous mixture was stirred at room temperature for 2 hours then at 80° C. for 1 hour. The reaction was cooled to room temperature and concentrated to dryness. Water was added followed by 1 N aqueous NaOH to neutralize to pH 7. The resulting precipitate was filtered, washed with water and dried in vacuo. The solid was then refluxed in MeOH for 2 hours, filtered and washed with MeOH to give 588 mg of pure 3-(2-bromo-phenyl)-1H-pyrazolo[3,4-d]thiazol-5-ylamine as an off-white solid. The filtrate was further purified on silica gel with 0-10% MeOH in CH$_2$Cl$_2$ as eluent to provide another 460 mg of 3-(2-bromo-phenyl)-1H-pyrazolo[3,4-d]thiazol-5-ylamine for a total of 1.408 g (88% yield). $^1$H-NMR (d$_6$-DMSO) δ: 13.1 and 12.6 (2 broad s, 1H, NH+tautomer), 7.73 (d, 1H), 7.61 (broad m, 1H), 7.48 (m, 3H), 7.34 (t, 1H); HPLC/MS m/z: 294.9, 296.9 [MH]$^+$.

To a vial charged with 3-(2-bromo-phenyl)-1H-pyrazolo[3,4-d]thiazol-5-ylamine (30 mg, 0.135 mmol), PS-DMAP (Argonaut resin, 0.54 g, 6 equiv.), and a stirring bar was added THF (1.5 mL) and 5-morpholin-4-ylmethyl-furan-2-carbonyl chloride hydrochloride (180 mg, 0.675 mmol). The reaction mixture was stirred at 70° C. for 17 hours, then cooled to room temperature and treated with PS-trisamine (Argonaut resin, 0.76 g, 20 equiv.) at 50° C. for 8 hours. The resin was filtered, washed with DMF and the solvent was evaporated. Purification on silica gel with 0-8% MeOH in CH$_2$Cl$_2$ as eluent provided 18 mg (27% yield) of 5-morpholin-4-ylmethyl-furan-2-carboxylic acid [3-(2-bromo-phenyl)-1H-pyrazolo[3,4-d]thiazol-5-yl]-amide as a white solid. $^1$H-NMR (d$_6$-DMSO) δ: 13.7 and 13.5 (2 broad s, 1H, NH+tautomer), 12.8 (broad s, 1H, NH), 7.65-7.82 (m, 3H), 7.49 and 7.55 (2 t, 1H, tautomers), 7.36 and 7.41 ( 2 t, 1H, tautomers), 6.58 (d, 1H), 3.59 (s, 2H), 3.56 (t, 4H), 2.41 (broad s, 4H); HPLC/MS m/z: 488.0, 490.0 [MH]$^+$.

Synthesis of cyclopropanecarboxylic acid [3-(4-hydroxy-phenyl)-1H-pyrazolo[3,4-d]thiazol-5-yl]-amide To a stirring suspension of 3-(4-methoxyphenyl)-1H-pyrazolo[3,4-d]thiazol-5-ylamine (100 mg, 0.41 mmol) in CH$_2$Cl$_2$ (2 mL) at −78° C. was added a 1 M solution of BBr$_3$ in CH$_2$Cl$_2$ (2.1 mL, 2.1 mmol) dropwise. The reaction mixture was slowly warmed up to room temperature overnight, then it was quenched with water, and the reaction mixture was neutralized to pH 6 with 1 N aqueous NaOH. The resulting precipitate was filtered, washed with water, and dried in vacuo to afford 70 mg (74% yield) of 3-(4-hydroxyphenyl)-1H-pyrazolo[3,4-d]thiazol-5-ylamine as an off-white solid. $^1$H-NMR (d$_6$-DMSO) δ: 9.8 (broad s, 1H), 7.57 (broad s, 2H), 7.42 (d, 2H), 6.85 (d, 2H); HPLC/MS m/z: 233.0 [MH]$^+$.

To a vial charged with 3-(4-hydroxyphenyl)-1H-pyrazolo[3,4-d]thiazol-5-ylamine (60 mg, 0.259 mmol), PS-DMAP (Argonaut resin, 1.05 g, 6 equiv.), and a stirring bar were added THF (2.5 mL) and cyclopropane-carbonyl chloride (118 μL, 1.29 mmol). The reaction mixture was stirred at 70° C. for 15 hours, then cooled to room temperature and treated with PS-trisamine (Argonaut resin, 1.26 g, 20 equiv.) at 50° C. for 48 hours. The resin was filtered, washed with DMF and the solvent was evaporated. Purification on silica gel with 0-8% MeOH in CH$_2$Cl$_2$ as eluent provided 32 mg (41% yield) of cyclopropanecarboxylic acid [3-(4-hydroxy-phenyl)-1H-pyrazolo[3,4-d]thiazol-5-yl]-amide as a white solid. $^1$H-NMR (d$_6$-DMSO) δ: 13.3 (broad s, 1H), 12.6 (broad s, 1H), 9.80 (broad s, 1H), 7.52 (d, 2H), 6.88 (d, 1H), 1.98 (m, 1H), 0.93 (m, 4H); HPLC/MS m/z: 301.0 [MH]$^+$.

Synthesis of (S)-acetic acid 1-[3-(2-chloro-phenyl)-1H-pyrazolo[3,4-d]thiazol-5-ylcarbamoyl]-ethyl ester To a solution of 3-(chlorophenyl)-3-oxo-propionitrile (4.0 g, 22.2 mmol) in absolute ethanol (21 mL) was added hydrazine hydrate (6.5 mL, 134 mmol). The reaction mixture was stirred at 80° C. for 15 hours, then it was concentrated in vacuo and purified on silica gel with 0-10% MeOH in CH$_2$Cl$_2$ as eluent to give 3.8 g (87% yield) of 5-amino-3-(2-chlorophenyl)pyrazole as a yellow solid. $^1$H NMR (d$_6$-DMSO) δ: 11.7 (broad s, 1H), 7.66 (d, 1H), 7.48 (d, 1H), 7.35 (t, 1H), 7.30 (t, 1H), 5.83 (s, 1H), 4.84 (broad s, 2H); HPLC/MS m/z: 194.1 [MH]$^+$.

To a solution of 5-amino-3-(2-chlorophenyl)pyrazole (3.8 g, 19.6 mmol) in THF (150 mL) was added dropwise benzoyl isothiocyanate (2.9 mL, 21.56 mmol). The reaction mixture was stirred at room temperature for 4 hours, then 4 N aqueous solution of NaOH (8 mL) was added, and the reaction mixture was further stirred at room temperature for 17 hours. The reaction mixture was neutralized to pH 7 with 1 N aqueous HCl, and extracted with EtOAc (3×). The combined organic layers were directly purified on silica gel with 0-10% MeOH in CH$_2$Cl$_2$ as eluent to provide 3.47 g (72 % yield) of [5-(2-chloro-phenyl)-2H-pyrazol-3-yl]-thiourea as a tan solid.

To a solution of [5-(2-chloro-phenyl)-2H-pyrazol-3-yl]-thiourea (2.25 g, 8.9 mmol) in glacial AcOH (900 mL) was added a 1.5 M solution of bromine in AcOH (20 mL) dropwise under vigorous stirring. The resulting heterogeneous mixture was stirred at room temperature for 2 hours then it was concentrated to dryness. Water was added followed by a saturated solution of aqueous sodium bicarbonate to neutralize to pH 7. The resulting precipitate was filtered, washed with water and dried in vacuo. Recrystallization from isopropyl alcohol afforded 1.48 g (66% yield) of 3-(2-chloro-phenyl)-1H-pyrazolo[3,4-d]thiazol-5-ylamine as a tan solid. $^1$H-NMR (d$_4$-MeOH) δ: 7.64 (broad s, 1H), 7.53 (d, 1H), 7.42 (m, 2H); HPLC/MS m/z: 251 [MH]$^+$.

To a vial charged with 3-(2-chloro-phenyl)-1H-pyrazolo[3,4-d]thiazol-5-ylamine (30 mg, 0.12 mmol) and PS-DMAP (Argonaut resin, 450 mg, 5 equiv.) were added THF (0.8 mL) and (S)-(−)-2-acetoxypropionyl chloride (126 mg, 0.84 mmol). The reaction mixture was shaken at 70° C. overnight, then cooled to room temperature and treated with PS-trisamine (Argonaut resin, 1.03 g, 30 equiv.) at 50° C. for 4 hours. The resin was filtered, washed with DMF and the solvent was evaporated. Purification by reverse-phase preparative HPLC provided 21 mg (48% yield) of the title compound. $^1$H-NMR (d$_6$-DMSO) δ: 7.78 (broad m, 1H), 7.61 (broad m, 1H), 7.47 (broad m, 2H), 5.13 (q, 1H), 2.09 (s, 3H), 1.44 (d, 3H); HPLC/MS m/z: 365.0 [MH]$^+$.

Other Examples of Bicyclic Pyrazolo Kinase Modulators

Further examples of bicyclic pyrazolo kinase modulators produced by the methods provided herein are set forth in Tables 1, and 5-10.

TABLE 1

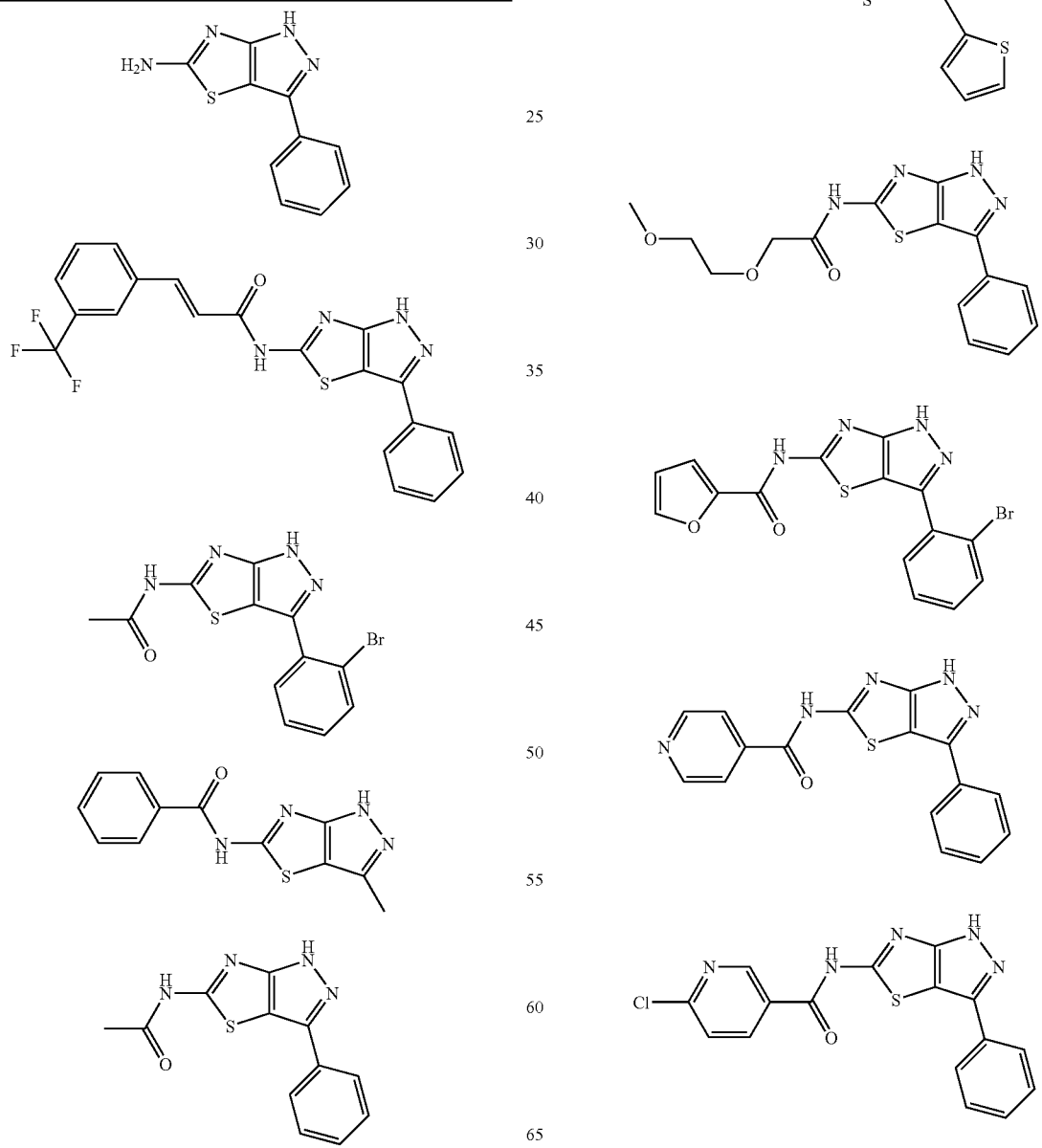

TABLE 1-continued

TABLE 1-continued
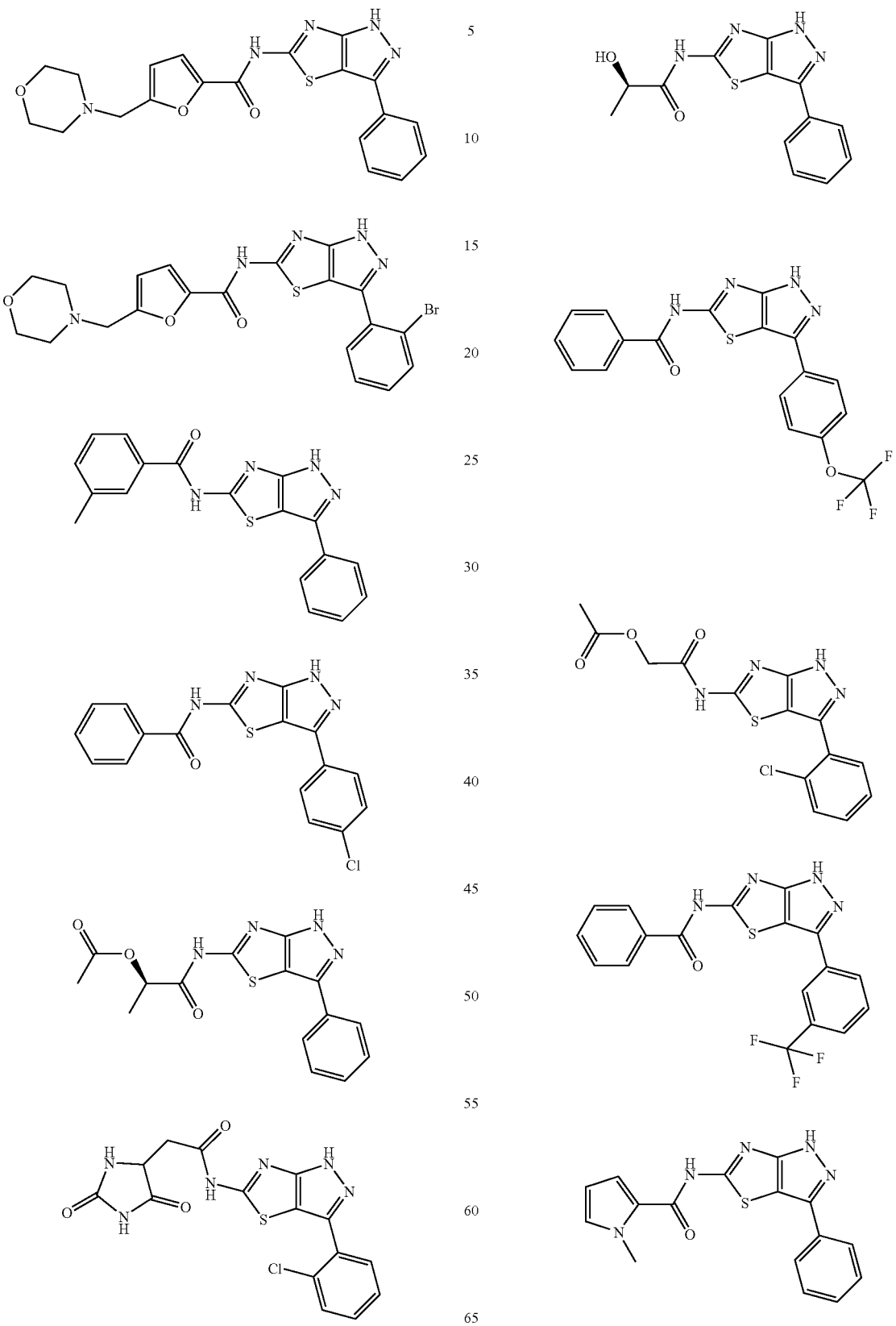

TABLE 1-continued
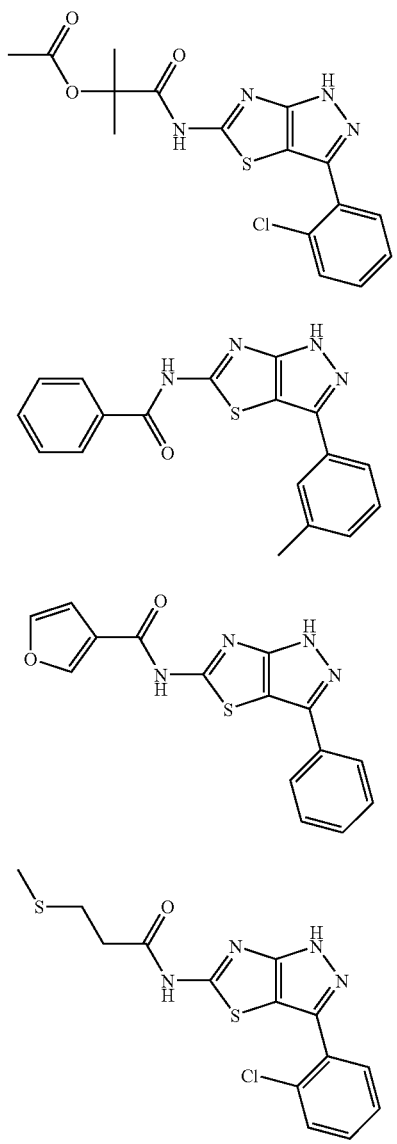
TABLE 1-continued
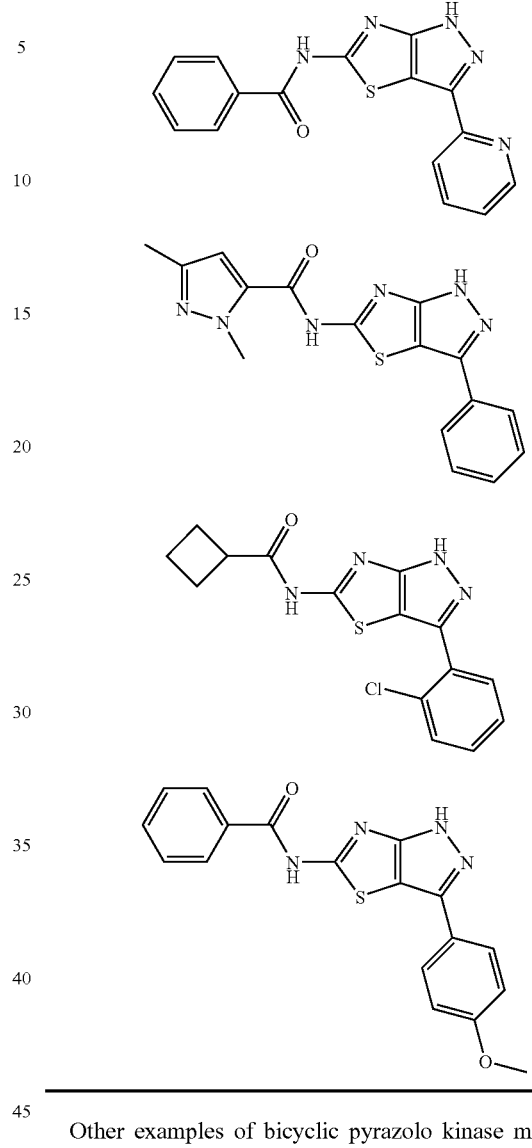
Other examples of bicyclic pyrazolo kinase modulators encompassed by the present invention are set forth in Tables 2 and 3 below.
TABLE 2
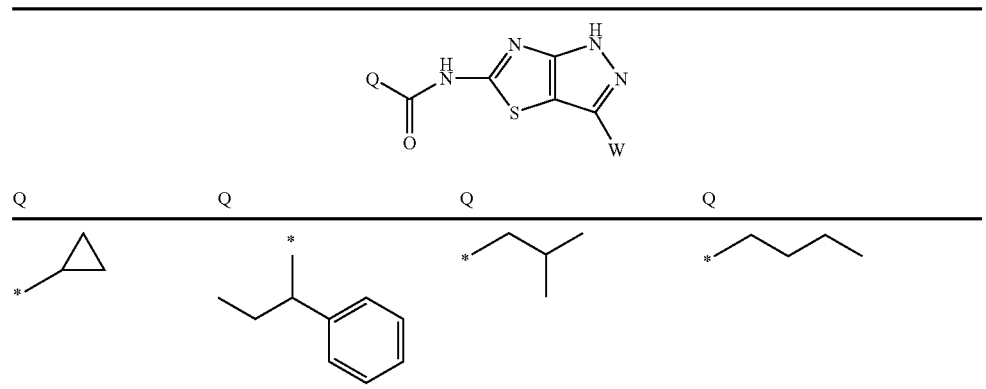

TABLE 2-continued
| Q | Q | Q | Q |
|---|---|---|---|
| 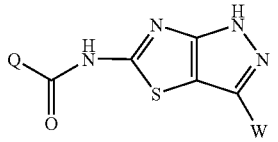 | 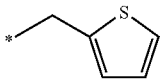 | 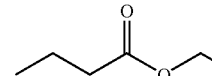 | 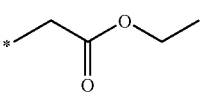 |
| 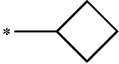 | 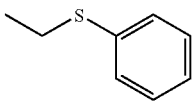 | 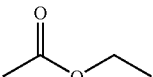 | 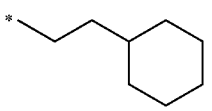 |
| 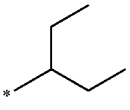 | 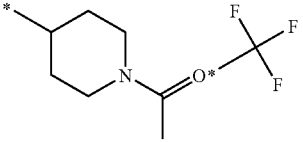 |  | 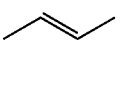 |
| 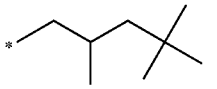 | 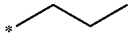 |  | 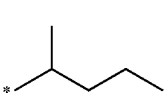 |
| 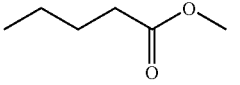 |  | 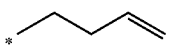 | 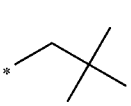 |
| 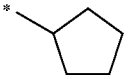 | 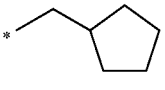 |  | 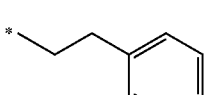 |
| 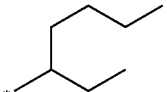 | 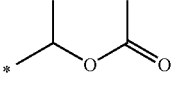 |  | 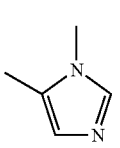 |
| 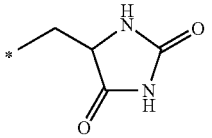 | 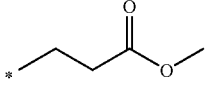 | 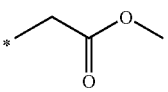 | 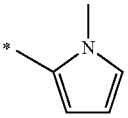 |
| 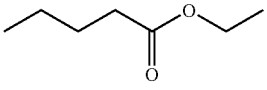 | 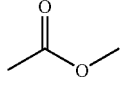 | 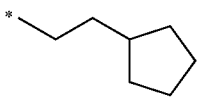 |  |
| 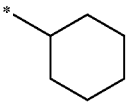 |  | 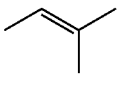 | 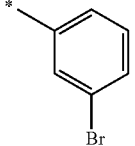 |
| 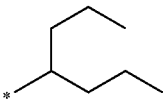 | 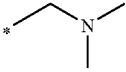 | 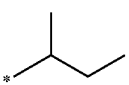 | 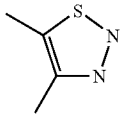 |

TABLE 2-continued
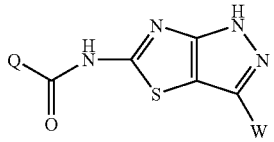
| Q | Q | Q | Q |
|---|---|---|---|
| 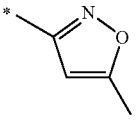 | 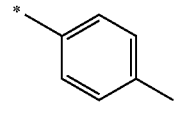 | 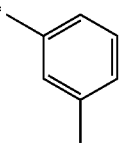 | 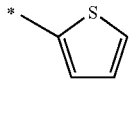 |
| 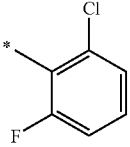 | 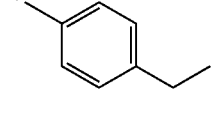 | 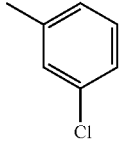 | 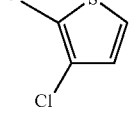 |
| 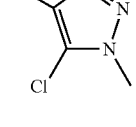 | 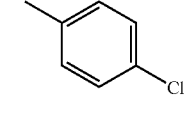 |  | |
| 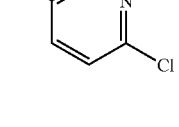 | 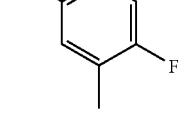 | 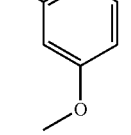 | |
| 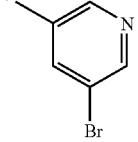 | 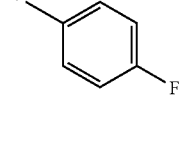 | 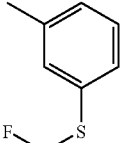 | |
| 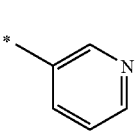 | 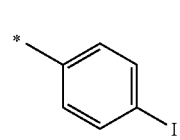 | 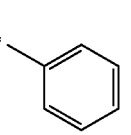 | |
| 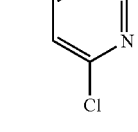 | 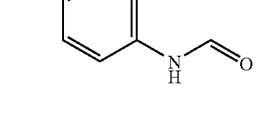 | 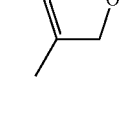 | |
| 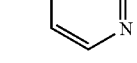 | 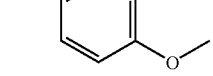 | 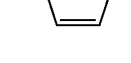 | |

TABLE 2-continued
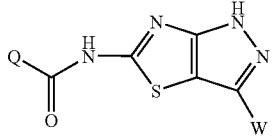
| Q | Q | Q | Q |
|---|---|---|---|
| 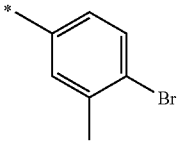 | 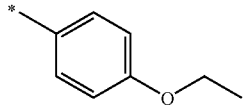 | 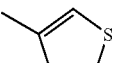 | |
| 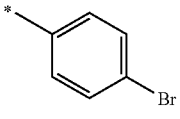 | 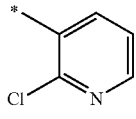 | 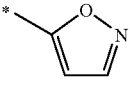 | |
TABLE 3
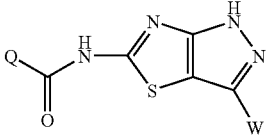
| W | W | W | W |
|---|---|---|---|
| 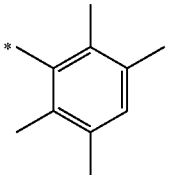 | 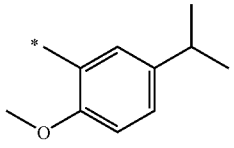 | 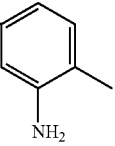 | 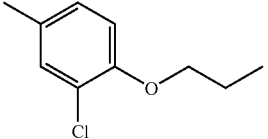 |
| 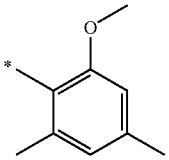 | 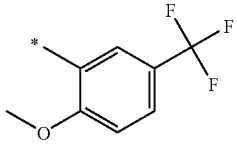 | 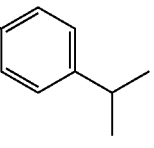 | 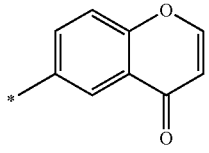 |
| 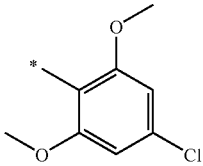 | 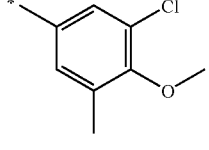 | 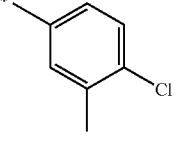 | 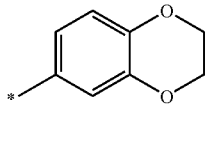 |
| 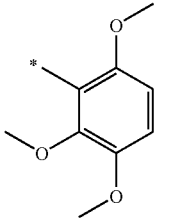 | 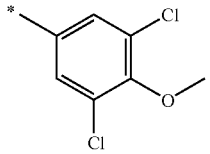 | 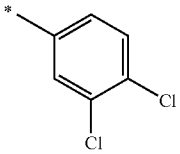 | 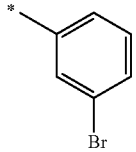 |

TABLE 3-continued
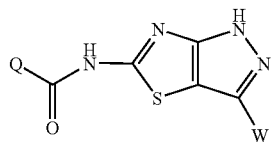
| W | W | W | W |
|---|---|---|---|
| 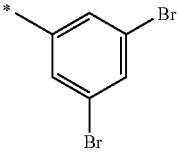 | 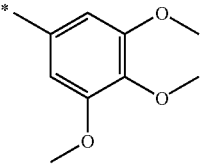 | 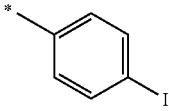 | 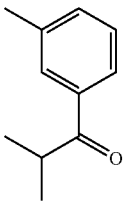 |
| 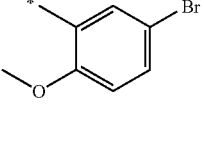 | 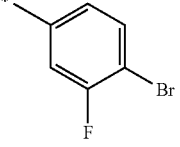 | 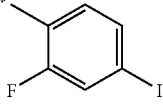 | 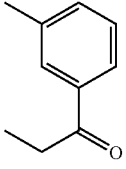 |
| 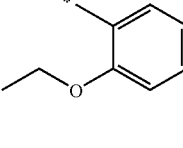 | 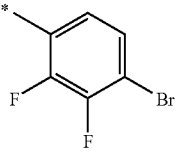 | 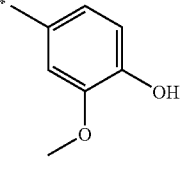 | 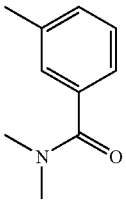 |
| 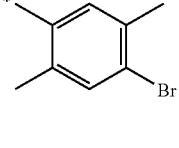 | 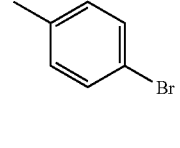 | 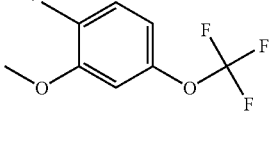 | 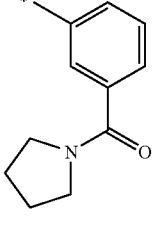 |
| 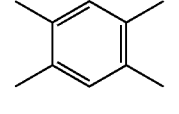 | 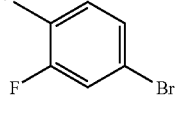 | 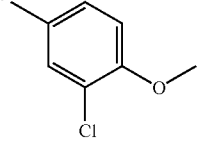 | 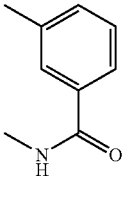 |
| 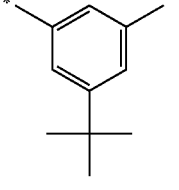 | 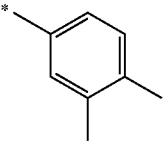 | 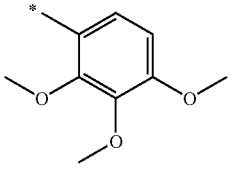 | 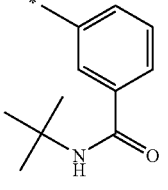 |

TABLE 3-continued
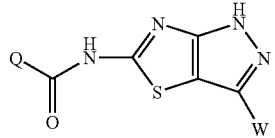

TABLE 3-continued
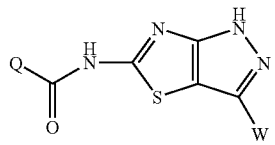
| W | W | W | W |
|---|---|---|---|
| 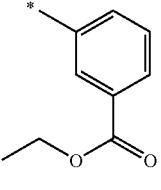 | 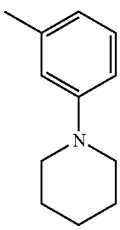 |  | 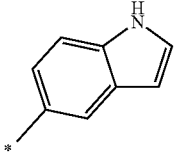 |
| 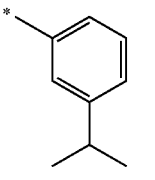 | 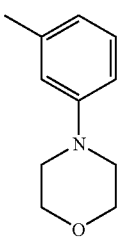 | 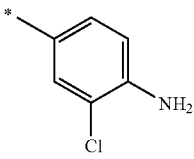 | 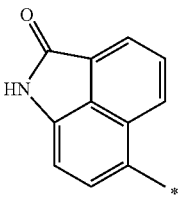 |
| 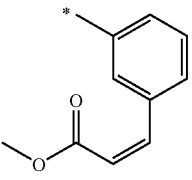 | 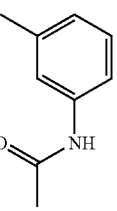 | 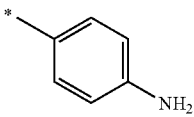 | 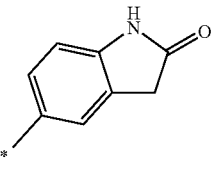 |
| 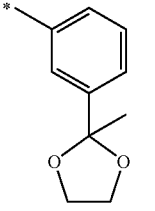 | 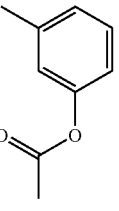 | 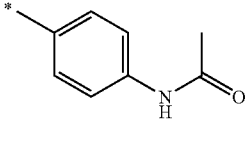 | 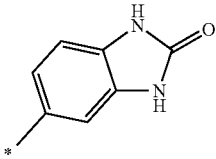 |
| 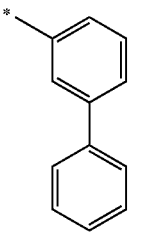 | 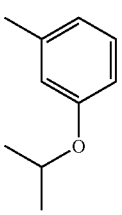 | 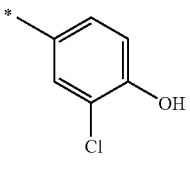 | 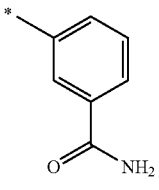 |
| 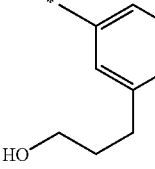 | 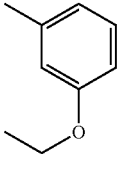 | 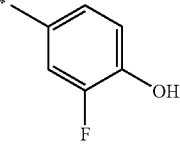 | 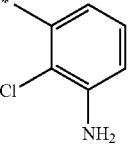 |

TABLE 3-continued
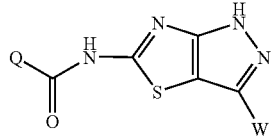
| W | W | W | W |
|---|---|---|---|
| 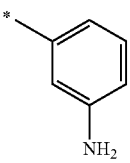 | 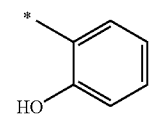 | 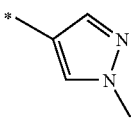 | 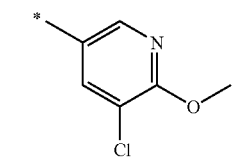 |
| 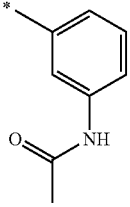 | 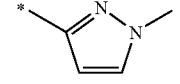 | 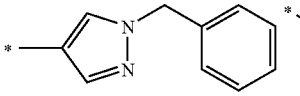 | 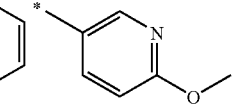 |
| 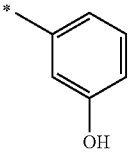 | 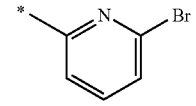 | 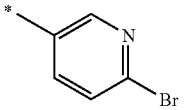 | 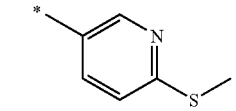 |
| 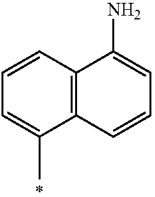 | 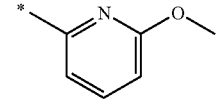 | 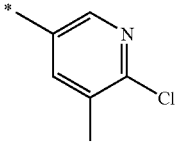 | 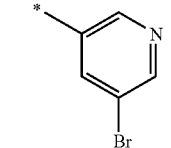 |
| 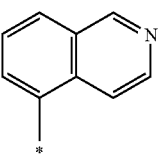 | 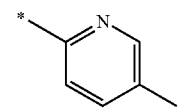 | 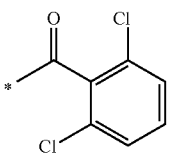 | 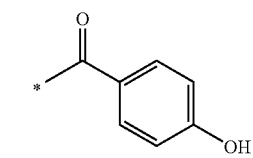 |
| 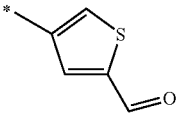 | 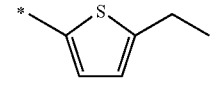 | 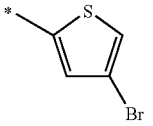 | 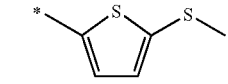 |
| 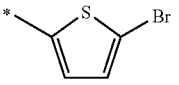 | 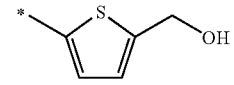 | 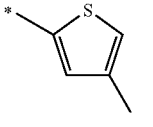 | 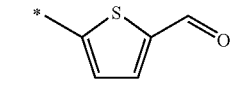 |
| 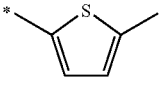 | 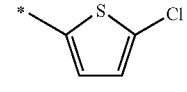 | 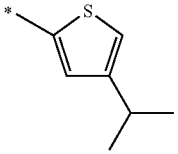 | 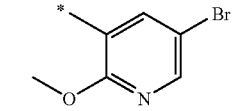 |

TABLE 3-continued

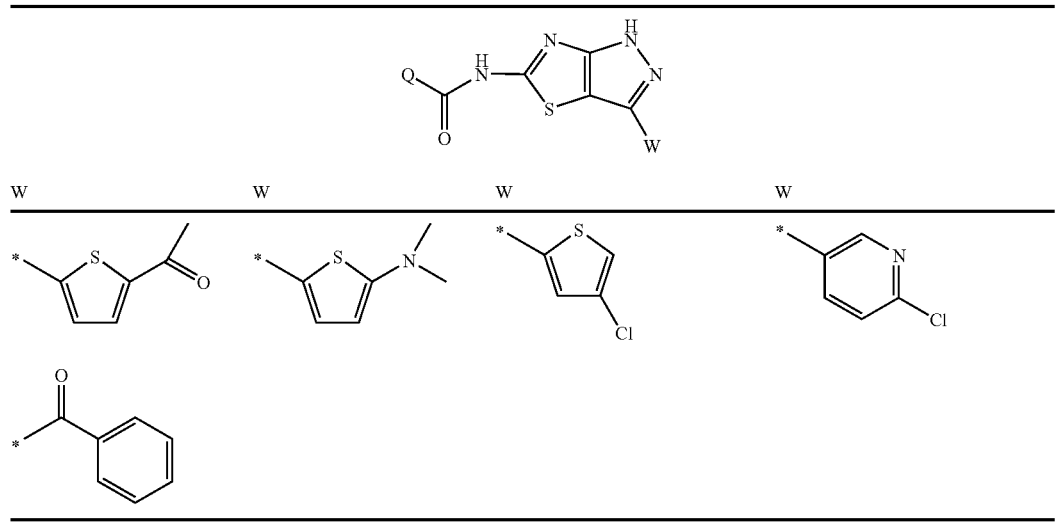

Example 2

Bioassays

Kinase assays known to those of skill in the art may be used to assay the inhibitory activities of the compounds and compositions of the present invention. Kinase assays include, but are not limited to, the following examples.

For the purposes of these assays, the kinases are pre-diluted to a 10× working concentration in the following buffers. For Blk, CSK, and Lyn, the buffer composition is 50 mM Tris pH 7.5, 0.1 mM EGTA, 0.1 mM $Na_3VO_4$, 0.1% β-mercaptoethanol, and 1 mg/ml BSA. For Abl, CDK1, CDK5, Aurora-A, cSRC, Flt3, Fyn, GSK3α, GSK3β, Lck, Rsk1, Rsk2, Rsk3, and Yes, the buffer composition is 20 mM MOPS, pH 7.0, 1 mM EDTA, 0.1% β-mercaptoethanol, 0.01% Brij-35, 5% glycerol, and 1 mg/ml BSA.

Kinases are assayed in final reaction volumes of 25 μl, comprising 5-10 mU of kinase, the reaction is initiated by the addition of a MgATP mix of (final concentration) 10 mM MgAcetate and [γ-$^{32}$P-ATP], having a specific activity of approximately 500 cpm/pmol, concentration as required. The reaction is incubated for 40 minutes at room temperature, then stopped by adding 5 μl of a 3% phosphoric acid solution. 10 μl of the reaction mix is then spotted onto a Filtermat A filter and is then washed three times in 75 mM phosphoric acid for five minutes and once in methanol. The filters are then dried and scintillation counted. Reactions further comprise reaction solutions and peptides, as presented in Table 4 below.

TABLE 4

| Kinase | Reaction Solution | Peptide |
|---|---|---|
| Abl | 8 mM MOPS, pH 7.0, 0.2 mM EDTA | 50 μM EAIYAAPFAKKK |
| Aurora-A | 8 mM MOPS, pH 7.0, 0.2 mM EDTA | 200 μM LRRASLG (Kemptide) |
| Blk | 50 mM Tris pH 7.5, 0.1 mM EGTA, 0.1 mM $Na_3VO_4$, 0.1% β-mercaptoethanol | 0.1 mg/ml poly (Glu, Tyr) 4:1 |
| CDK1 | 8 mM MOPS, pH 7.0, 0.2 mM EDTA | 0.1 mg/ml histone H1 |
| CDK5 | 8 mM MOPS, pH 7.0, 0.2 mM EDTA | 0.1 mg/ml histone H1 |
| CSK | 50 mM Tris pH 7.5, 0.1 mM EGTA, 0.1 mM $Na_3VO_4$, 0.1% β-mercaptoethanol | 0.1 mg/ml poly (Glu, Tyr) 4:1 |
| cSRC | 8 mM MOPS, pH 7.0, 0.2 mM EDTA | 250 μM KVEKIGEGTYGVVYK (Cdc 2 peptide) |
| Flt3 | 8 mM MOPS, pH 7.0, 0.2 mM EDTA | 50 μM EAIYAAPFAKKK |
| Fyn | 50 mM Tris pH 7.5, 0.1 mM EGTA, 0.1 mM $Na_3VO_4$ | 250 μM KVEKIGEGTYGVVYK (Cdc2 peptide) |
| GSK3α | 8 mM MOPS, pH 7.0, 0.2 mM EDTA | 20 μM YRRAAVPPSPSLSRHSSPHQS(p)EDEEE (phospho GS2 peptide) |

TABLE 4-continued

| Kinase | Reaction Solution | Peptide |
|---|---|---|
| GSK3β | 8 mM MOPS, pH 7.0, 0.2 mM EDTA | 20 µM YRRAAVPPSPSLSRHSSPHQS(p)EDEEE (phospho GS2 peptide) |
| Lck | 50 mM Tris pH 7.5, 0.1 mM EGTA, 0.1 mM Na$_3$VO$_4$ | 250 µM KVEKIGEGTYGVVYK (Cdc-2 peptide) |
| Lyn | 50 mM Tris pH 7.5, 0.1 mM EGTA, 0.1 mM Na$_3$VO$_4$, 0.1% β-mercaptoethanol | 0.1 mg/ml poly (Glu, Tyr) 4:1 |
| Rsk1 | 8 mM MOPS, pH 7.0, 0.2 mM EDTA | 30 µM KKKNRTLSVA |
| Rsk2 | 8 mM MOPS, pH 7.0, 0.2 mM EDTA | 30 µM KKKNRTLSVA |
| Rsk3 | 8 mM MOPS, pH 7.0, 0.2 mM EDTA | 30 µM KKKNRTLSVA |
| Yes | 8 mM MOPS, pH 7.0, 0.2 mM EDTA | 0.1 mg/ml poly (Glu, Tyr) 4:1 |

FLT3 Assay

Although this example presents the use of the FLT3 kinase domain, the kinase assays may use various forms of FLT3, including, for example, the entire molecule, the kinase domain, or a portion thereof.

Materials: Substrate peptide=Poly (Glu, Tyr) 4:1=poly EY (Sigma P-0275); βNADH (Sigma CAT#N-8129, FW=709.4); 2M MgCl$_2$; 1M HEPES buffer, pH 7.5; Phosphoenolpyruvate=PEP (Sigma CAT#P-7002, FW=234); Lactate dehydrogenase=LDH (Worthington Biochemical CAT#2756); Pyruvate Kinase=PK (Sigma CAT#P-9136); ATP (Sigma CAT#A-3377, FW=551); Greiner 384-well UV star plate; and purified and autophosphorylated FLT3 kinase domain (FLT3KD).

Stock Solutions: 10 mM NADH (7.09 mg/mL in miliQH$_2$O) make fresh daily; 1 mg/mL Poly EY (in miliQH$_2$O) store at −20° C.; 200mM HEPES buffer, pH 7.5 (10 ml 1M stock+40 ml miliQH$_2$O) supplemented with 1 mM DTT; 100 mM MgCl2 (5 mL+95 ml dH$_2$)); 100 mM PEP (23.4 mg/mL in dH$_2$O) store at −20° C.; 10 mM ATP (5.51 mg/mL in dH$_2$O) store at −20° C. (dilute 1 mL into total of 10 mL miliQH$_2$O daily=1 mM ATP working stock); 1000 U/mL PK (U/mg varies with lot) flash-freeze under liquid N2 and store at −80° C.; 1000 U/mL LDH (U/mg varies with lot) flash-freeze under liquid N2 and store at −80° C.

Standard Assay Setup for 384-well format (50 µl reaction): 300 µM NADH; 10 mM MgCl$_2$; 2 mM PEP; 45 U/mL PK; 60 U/mL LDH; 1 mg/mL Poly EY; 2.5 µL test compound (in DMSO); 10 µg/mL autophosphorylated FLT3 kinase domain; 250 µM ATP*; 100 mM HEPES buffer; QS with miliQ dH2O to 50 µL. Positive controls contained DMSO with no test compound. Negative controls contained 5 µl of 0.5M EDTA (50 mM in the assay). The kinase reaction was initiated at time t=0 by the addition of ATP.

The unphosphorylated FLT3KD that was produced required pre-incubation with MgATP to allow for autophosphorylation and full kinase activity. The autophosphorylation reaction was run in 100 mM HEPES buffer, 1 mM DTT, and 1 mg/mL FLT3KD by the addition of ATP and MgCl$_2$ to a final concentration of 2 mM and 10 mM respectively. The reaction was allowed to proceed at room temperature for 90 minutes, and then was quenched by the addition of EDTA to 50 mM. The autophosphorylated protein was then aliquotted and flash frozen in liquid N$_2$ for use.

The activity was measured by following the time-dependent loss of NADH by absorbance spectroscopy at 340 nm. The linear portion of the resulting progress curve was then be analyzed by linear regression to get the activity in absorbance units/time, reported as the slope of that best fit line (moles/unit time can be calculated from using molar extinction coeffecient for NADH at 340 nm, 6250M$^{-1}$cm$^{-1}$).

Data was analyzed using the equation: $Z'=1-[3*(\sigma_+ +\sigma_-)/|\mu_+ -\mu_-|]$, where µ denotes the mean and σ the standard deviation. The subscript designates positive or negative controls. The Z' score for a robust screening assay should be ≧0.50. The typical threshold=$\mu_+ -3*\sigma_+$. Any value that falls below the threshold was designated a "hit."

The dose response was measured using the equation: $y=\min+\{(\max-\min)/1+10^{[compound]-logIC50)}\}$, where y is the observed initial slope, max is the slope in the absence of inhibitor, min is the slope at infinite inhibitor, and the IC$_{50}$ is the [compound] that corresponds to ½ the total observed amplitude (Amplitude=max−min). The IC$_{50}$ is related to the K$_i$ by the following equation: IC$_{50}$=K$_i$(1+[ATP]/Km).

To measure modulation, activation, or inhibition of FLT3KD, a test compound was added to the assay at a range of concentrations. Inhibitors may inhibit FLT3KD activity at an IC$_{50}$ in the micromolar range, the nanomolar range, and, for example, in the subnanomolar range.

To measure the binding of a compound to FLT3 or FLT3KD, a test kit manufactured by Discoverx (Fremont, Calif.), ED-Staurosporine NSIP™ Enzyme Binding Assay Kit (see U.S. Pat. No. 5,643,734) was used. Results are shown in Tables 5 and 6 below.

TABLE 5

| Structure | Flt3 IC50 |
|---|---|
| 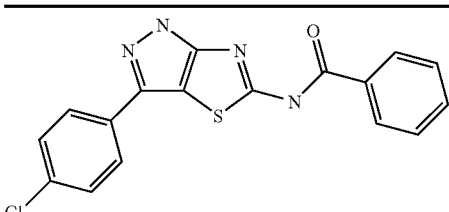 | A |

TABLE 5-continued

| Structure | Flt3 IC50 |
|---|---|
| 3-(trifluoromethyl)phenyl pyrazolothiazole benzamide | B |
| 3-phenyl pyrazolothiazole isonicotinamide | A |
| 3-phenyl pyrazolothiazole 3-bromobenzamide | B |
| 3-phenyl pyrazolothiazole 2-(2-methoxyethoxy)acetamide | B |
| 3-phenyl pyrazolothiazole 1-acetylpiperidine-4-carboxamide | B |

In Table 5, A is <1 µM, B is 1-10 µM, and C is 11-100 µM.

TABLE 6

| Structure | FLT3 IC50 |
|---|---|
| isoxazole-5-carboxamide phenyl pyrazolothiazole | A |
| cyclopropanecarboxamide 4-hydroxyphenyl pyrazolothiazole | A |
| benzamide tert-butyl pyrazolothiazole | B |
| benzamide furan-2-yl pyrazolothiazole | B |
| furan-2-carboxamide pyridin-2-yl pyrazolothiazole | B |

TABLE 6-continued

| Structure | FLT3 IC50 |
|---|---|
| benzamide pyridin-4-yl pyrazolothiazole | A |

TABLE 6-continued

| Structure | FLT3 IC50 |
|---|---|
| (pyridine-4-carboxamide linked to tert-butyl pyrazolo-thiazole) | C |
| (3-bromobenzamide linked to phenyl pyrazolo-thiazole) | C |

In Table 6, A is IC50<0.1 μM; B is 0.1 μM<IC50<1 μM; and C is IC50>1 μM.

Abl Assay

Although this example presents the use of the kinase domain of a mutant form of Abl T315I 0-P, the kinase assays may use various forms of mutant and wild type Abl, including, for example, the entire molecule, the kinase domain, or a portion thereof. The kinases used in the assays may also be of varying phophorylation states. In the present example, a mutant kinase at a zero phosphorylation state was used.

Materials: Abl substrate peptide=EAIYAAPFAKKK-OH (Biopeptide, SD CA); βNADH (Sigma CAT#N-8129, FW=709.4); 2M $MgCl_2$; 1M HEPES buffer, pH 7.5; Phosphoenolpyruvate=PEP (Sigma CAT#P-7002, FW=234); Lactate dehydrogenase=LDH (Worthington Biochemical CAT#2756); Pyruvate Kinase=PK (Sigma CAT#P-9136); ATP (Sigma CAT#A-3377, FW=551); Greiner 384-well UV star plate; and Purified and unphosphorylated T315I Abl kinase domain (clone 5582d42PPt6p6).

Stock Solutions: 10 mM NADH (7.09 mg/mL in $miliQH_2O$) make fresh daily; 10 mM Abl substrate peptide (13.4 mg/mL in $miliQH_2O$) store at −20° C.; 100 mM HEPES buffer, pH 7.5 (5 mL 1M stock+45 mL $miliQH_2O$); 100 mM $MgCl_2$ (5 mL 2M $MgCl_2$+95 ml $dH_2O$); 100 mM PEP (23.4 mg/mL in $dH_2O$) store at −20° C.; 10 mM ATP (5.51 mg/mL in $dH_2O$) store at −20° C. (dilute 50 μL into total of 10 mL $miliQH_2O$ daily=50 μM ATP working stock); 1000 U/mL PK (U/mg varies with lot) flash-freeze under liquid N2 and store at −80° C.; and 1000 U/mL LDH (U/mg varies with lot) flash-freeze under liquid N2 and store at −80° C.

Standard Assay Setup for 384-well format (50 μl reaction): 300 μM NADH; 10 mM $MgCl_2$; 2 mM PEP; 45 U/mL PK; 60 U/mL LDH; 200 μM Abl substrate peptide; 2.5 μL test compound (in DMSO); 2 μg/mL Abl kinase domain; 10 μM ATP; 100 mM HEPES buffer; QS with miliQ $dH2O$ to 50 μL; Positive controls contained DMSO with no test compound. Negative controls contained 5 μl of 0.5M EDTA (50 mM in the assay). The dephosphorylated form of the c-Abl T315I mutant were used in the biochemical screening assays. The kinase reaction was initiated at time t=0 by the addition of ATP.

The activity was measured by following the time-dependent loss of NADH by absorbance spectroscopy at 340 nm. The linear portion of the resulting progress curve was then be analyzed by linear regression to get the activity in absorbance units/time, reported as the slope of that best fit line (moles/unit time can be calculated from using molar extinction coefficient for NADH at 340 nm, $6250 M^{-1}cm^{-1}$).

Data was analyzed using the equation: $Z'=1-[3*(\sigma_++\sigma_-)/|\mu_+-\mu_-|]$, where μ denotes the mean and σ the standard deviation. The subscript designates positive or negative controls. The Z' score for a robust screening assay should be ≧0.50. The typical threshold=$\mu_+-3*\sigma_+$. Any value that falls below the threshold was designated a "hit".

Dose response was analyzed using the equation: y=min+{(max−min)/(1+10^{[compound]-logIC50})}, where y is the observed initial slope, max=the slope in the absence of inhibitor, min=the slope at infinite inhibitor, and the $IC_{50}$ is the [compound] that corresponds to ½ the total observed amplitude (Amplitude=max−min).

To measure modulation, activation, or inhibition of AblKD, a test compound was added to the assay at a range of concentrations. Inhibitors may inhibit AblKD activity at an $IC_{50}$ in the micromolar range, the nanomolar range, and, for example, in the subnanomolar range.

To measure the binding of a compound to Abl or AblKD, a test kit manufactured by Discoverx (Fremont, Calif.), ED—Staurosporine NSIP™ Enzyme Binding Assay Kit (see U.S. Pat. No. 5,643,734) was used. Results are presented in Tables 7 and 8 below.

TABLE 7

| Structure | cAbl IC50 (uM) |
|---|---|
| (phenyl pyrazolo-thiazole amine) | C |
| (3-chlorophenyl pyrazolo-thiazole benzamide) | B |
| (pyridyl pyrazolo-thiazole benzamide) | C |
| (4-methoxyphenyl pyrazolo-thiazole benzamide) | C |

TABLE 7-continued
| Structure | cAbl IC50 (uM) |
|---|---|
| 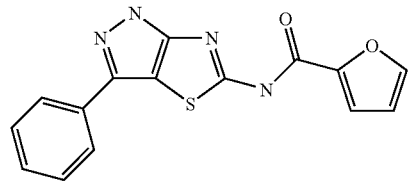 | A |
| 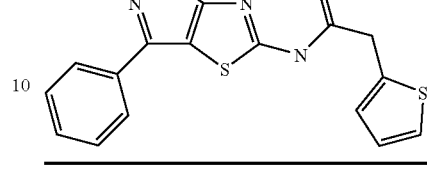 | A |
In Table 7, A is <1 μM, B is from 1-10 μM, and C is from 11-100 μM.
TABLE 8
| Compound | Abl T315I IC50 | Abl Y393F IC50 |
|---|---|---|
| 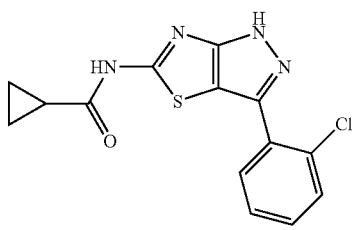 | A | A |
| 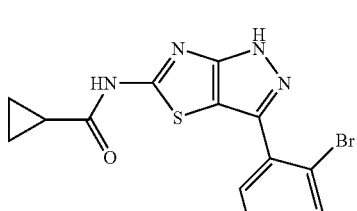 | A | A |
| 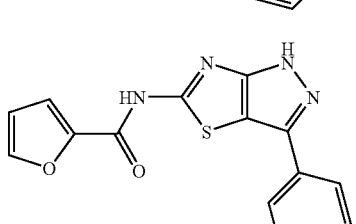 | A | A |
| 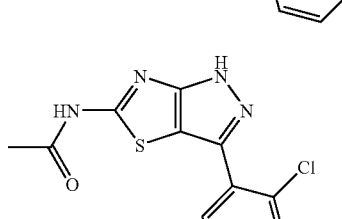 | C | C |
| 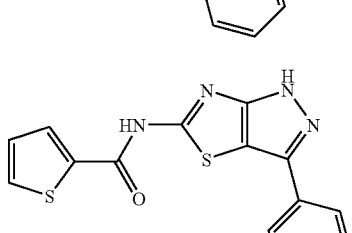 | B | B |

TABLE 8-continued

| Compound | Abl T315I IC50 | Abl Y393F IC50 |
|---|---|---|
| (cyclopropanecarboxamide-thiazolopyrazole with 4-methoxyphenyl) | B | C |
| (benzamide-thiazolopyrazole with 3-bromophenyl) | C | C |
| (methoxyacetamide-thiazolopyrazole with phenyl) | C | C |

In Table 8, A is IC50<0.5 μM; B is 0.5 μM<IC50<1 μM; C is IC50>1 μM.

MET and RON Assays

Although this example presents the use of wild type MET and RON M1243T, the the kinase assays may use various forms of mutant and wild type RON or MET, including, for example, the entire intracellular domain, the kinase domain, or a portion thereof. The kinases used in the assays may also be of varying phophorylation states. In the case of RON, a mutant kinase at a zero phosphorylation state was used.

For the MET and RON assays, the Kinase-Glo® assay system (Promega) was used, which employs firefly luciferase to detect the amount of ATP following a kinase reaction. This assay system has two steps. First, the kinase reaction is run for a designated period of time. Next, an equivalent volume of Kinase-Glo reagent is added to quench the kinase reaction and detect the ATP remaining in the sample. The total light output is read by a plate-reading luminometer and the resulting signal is stable for 4 hours. Inhibition of kinase activity translates into lower ATP consumption and thus higher light output during the detection step.

Materials: Poly EY 4:1 (Sigma); MgCl$_2$ (2M stock available from Lab Support); HEPES buffer, pH 7.5; Bovine serum albumin (Roche 92423420); ATP (Sigma CAT#A-3377, FW=551); White Costar 384-well flat-bottom plate (VWR 29444-088); and SGX RON kinase clone (M1254T activation loop mutant) or SGX MET kinase clone.

MET enzyme mix: 100 mM HEPES pH 7.5, 10 mM MgCl2, 0.3 mg/mL poly EY, 0.1% BSA, and 0.4 μg/mL MET kinase.

RON enzyme mix: 100 mM HEPES pH 7.5, 10 mM MgCl2, 1 mg/mL poly EY, 0.1% BSA, and 3-5 μg/mL RON kinase (depending on enzyme prep).

To each well of a multiwell plate was added 15 μL of the enzyme mix, 1 μL of compound at 20-times the desired final assay concentration (or DMSO for positive controls or 200 μM staurosporine for negative controls), and 4 μL of 50 μM ATP to start the reaction. The kinase was reaction to allowed to proceed for 60 minutes at RT for the MET assay. For the RON assay, the reaction proceeded at RT for 60 minutes to 120 minutes (depending on enzyme prep). 20 μL Kinase-Glo reagent was then added to each well. The reagent was incubated for at least 10 minutes before plate reading.

Data anlaysis was performed using methods similar to those described above in the Abl assay (Firepower®, Exegetix).

Results of the assay are presented in Table 9 below.

TABLE 9

| Compound | Met IC50 | Ron IC50 |
|---|---|---|
| (cyclopropanecarboxamide-thiazolopyrazole with 4-hydroxyphenyl) | A | B |

TABLE 9-continued

| Compound | Met IC50 | Ron IC50 |
|---|---|---|
| (isobutyramide-pyrazolothiazole-2-Cl-phenyl) | A | B |
| (cyclopropanecarboxamide-pyrazolothiazole-2-Cl-phenyl) | A | B |
| (2,6-dimethoxybenzamide-pyrazolothiazole-2-Cl-phenyl) | B | B |
| (cyclopropanecarboxamide-pyrazolothiazole-2-Br-phenyl) | B | C |
| (acetoxy-propanamide-pyrazolothiazole-2-Cl-phenyl) | C | C |
| (cyclopropanecarboxamide-pyrazolothiazole-4-OMe-phenyl) | C | C |

In Table 9, A is IC50<5 uM, B is 5 uM<IC50<20 uM, and C is IC50>20 uM.

Example 3

Preparation and Expression of Selected Kinases

Preparation of Human FLT3

FLT3 kinase domain for bioassays were prepared, for example, as follows. Human liver cDNA was synthesized using a standard cDNA synthesis kit following the manufacturers' instructions. The template for the cDNA synthesis was mRNA isolated from Hep G2 cells [ATCC HB-8065] using a standard RNA isolation kit. An open-reading frame for the FLT3 kinase domain (FLT3KD) was amplified from the human liver cDNA by the polymerase chain reaction (PCR) using the following primers:

```
                                        (SEQ ID NO:1)
Forward primer:    CACAAGTACAAAAAGCAATTTAGGTATG (SEQ ID NO:2)
Reverse primer:    CCGAATCTTCGACCTGAG
```

The PCR product (840 base pairs expected) was electrophoresed on a 1.2% E-gel (Cat. #G5018-01, Invitrogen Corporation) and the appropriate size band was excised from the gel and eluted using a standard gel extraction kit. The eluted DNA was TOPO ligated into a GATEWAY™ (Invitrogen Corporation) adapted pcDNA6 AttB HisC vector which is custom TOPO adapted by Invitrogen Corporation. The resulting sequence of the gene after being TOPO ligated into the vector, from the start sequence through the stop site is as follows: ATG GCC CTT 3'[FLT3KD]5'AA GGG CAT CAT CAC CAT CAC CAC TGA (SEQ ID NO:3). The FLT3KD expressed using this vector had an N-terminal methionine, the kinase domain of FLT3KD, and a C terminal 6 X His-tag.

Plasmids containing TOPO ligated inserts were transformed into chemically competent TOP 10 cells (Invitrogen Corporation, Cat.#C4040-10). Colonies were then screened for inserts in the correct orientation and small DNA amounts were purified using a "miniprep" procedure from 2 ml cultures, using a standard kit, following the manufacturer's instructions. For standard molecular biology protocols followed here, see also, for example, the techniques described in Sambrook et al., Molecular Cloning: A Laboratory Manual, Cold Spring Harbor Laboratory, NY, 2001, and Ausubel et al., Current Protocols in Molecular Biology, Greene Publishing Associates and Wiley Interscience, NY, 1989. The DNA that was in the "correct" orientation was then sequence verified.

A standard GATEWAY™ BP recombination was performed into pDONR201 (Invitrogen Corporation, Cat.#11798014. Gateway technology Cat.#11821014) and the recombination reaction was transformed into chemically competent TOP 10 cells (Invitrogen Corporation, Cat.#C4040-10), and plated on selective media. One colony was picked into a miniprep and DNA was obtained (the "entry vector").

The "entry vector" DNA was used in a standard GATEWAY™ LR recombination with pDEST8™ (Invitrogen Corporation, Cat.#11804010) and transformed into chemically competent TOP 10 cells (Invitrogen Corporation, Cat.#C4040-10), and plated on selective media. One colony was picked into a miniprep and DNA was obtained (the "destination vector").

The "destination vector" was then transformed into DH10 BAC chemically competent cells (Invitrogen Corporation, Cat#10361012) which used site specific transposition to insert a foreign gene into a bacmid propogated in *E.coli*. The transformation was then plated on selective media. 1-2 colonies were picked into minipreps. The Nautilus Genomic miniprep kit (Active Motif, Cat.#50050) was used to purify the bacmid DNA. The bacmid was then verified by PCR.

The plasmid was transfected and expressed in SF9 cells using the following standard Bac to Bac protocol (Invitrogen Corporation, Cat.#10359-016).

Day 0: Seeded 9X10E5 cells per 35 mm well (of a 6 well plate) in 2 ml Sf-900II SFM (Invitrogen Corporation, Cat. #10902-104) containing 1% Penicillin/Streptomycin (Invitrogen Corporation, Cat. # 15140122). Allowed cells to attach at 27° C. for 1 hour. In a Falcon 2059 polypropylene 12X75 mm tube prepared the following solutions. Diluted 5 μl of FLT3KD miniprep bacmid DNA (Active Motif, Nautilus Genomic DNA Mini Kit Cat. # 50050) into 100 μl Sf-900II SFM without pen/strep. Diluted 6 μl of CellFECT1N reagent (Invitrogen Corporation, Cat. #10362-010) into 100 μl Sf-900II SFM without pen/strep. Combined the 2 solutions together and incubated 30 minutes at room temperature. Washed the cells once by aspirating old media and adding Sf-900II SFM without pen/strep. Removed media and added 0.8 ml Sf-900II SFM without pen/strep to each well. Added lipid/DNA to well. Incubated 5 hours in 27° C. incubator. Removed media and replaced with 2 ml Sf-900II SFM containing Penicillin/Streptomycin. Placed in 27° C. incubator.

Day 3, P1 to P2: In a T75 Tissue Culture Flask seeded 6X10E6 SF9 cells in a total volume of 14 ml Sf-900II SFM containing Penicillin/Streptomycin. Allowed to attach for 1 hour. Using a 5 ml pipette, removed supernatant containing infectious P1 FLT3KD Baculovirus particles from the transfected well of the 6 well and transfered directly into T75 Flask. Placed in 27° C. incubator.

Day 10, P2 to P3: On Day 10 Harvested FLT3KD Baculovirus supernatant and cells by vigorously pipetting the media to remove the cells from the flask wall. Pipetted the media and cells into a 15ml sterile conical tube and centrifuged the tube at @2000 rpm at room temperature for 5 minutes. Saved supernatant (P2). Cells were analyzed for protein expression by western blot.

P3 infection: Seeded SF21 cells in a 500 ml suspension flask at 2X10E6 cells per ml. in a total volume of 100 ml. Added infectious FLT3KD supernatant (14 ml) from P2 expression to suspension flask. Incubated at 27 C, shaking at 120-130 rpm. Expressed protein for 72 hours.

Harvested 1 ml cells and western blotted to determine expression: Harvested P3 supernatant by centrifugation 3000 rpm for 15 minutes at room temperature. Sterile filtered viral supernatant.

FLT3KD Scale up: Seeded 6 liters of SF21 cells at 2X10E6 cells per ml in 1 liter of cells in 2-liter suspension flasks. Infected cells with 15 ml of P3 FLT3KD baculovirus per liter. Incubated at 27 C, shaking at 120-130 rpm. Expressed protein for 48 hours. Harvested 1 ml cells from each liter and western blotted to determine expression. Remaining cells were collected by centrifugation, and the pellets stored at −80° C. After thawing at room temperature, cells were lysed in cracking buffer (50 mM Tris-HCl, pH 8.0; 200 mM arginine; 150 mM NaCl; 10% glycerol; 0.1% Igepal 630), and centrifuged to remove cell debris. The soluble fraction was purified over an IMAC column charged with nickel (Pharmacia, Uppsala, Sweden), and eluted under native conditions with a step gradient of 400 mM imidazole in 50 mM Tris pH7.8, 10 mM methionine, 10% glycerol. The FLT3KD protein was then purified by gel filtration using a Superdex 200 preparative grade column equilibrated in GF4 buffer (10 mM HEPES, pH 7.5, 10 mM methionine, 500 mM NaCl, 5 mM DTT, and 10% glycerol). Fractions containing the purified FLT3 kinase domain were pooled and concentrated to 1-5 mg/ml.

Flt3, or a portion thereof, such as, for example, the kinase domain, may also be purified according to methods known to those of ordinary skill in the art. Examples of methods used to obtain Flt3 for assays, include, but are not limited to, those presented in Weisberg, Ellen, et al., Cancer Cell 1:433-43, (2002).

Although the above protein kinase expression methods are exemplified by describing the expression of FLT3, other protein kinases (e.g. MET, and RON) were expressed using similar methodologies or methodologies generally know in the art.

Preparation of Human Abl

A lambda phosphatase co-expression plasmid was constructed as follows.

An open-reading frame for Aurora kinase was amplified from a *Homo sapiens* (human) HepG2 cDNA library (ATCC HB-8065) by the polymerase chain reaction (PCR) using the following primers:

```
                                           (SEQ ID NO:4)
Forward primer:     TCAAAAAAGAGGCAGTGGGCTTTG (SEQ ID NO:5)
Reverse primer:     CTGAATTTGCTGTGATCCAGG
```

The PCR product (795 base pairs expected) was gel purified as follows. The PCR product was electrophoresed on a 1% agarose gel in TAE buffer and the appropriate size band was excised from the gel and eluted using a standard gel extraction kit. The eluted DNA WAS ligated for 5 minutes at room temperature with topoisomerase into pSB2-TOPO. The vector pSB2-TOPO is a topoisomerase-activated, modified version of pET26b (Novagen, Madison, Wis.) wherein the following sequence has been inserted into the NdeI site: CATAATGGGCCATCATCATCATCATCACGGT GGTCATATGTCCCTT (SEQ ID NO:6) and the following sequence inserted into the BamHI site: AAGGGGGATCCTAAACTGC AGAGATCC (SEQ ID NO:7). The sequence of the resulting plasmid, from the Shine-Dalgarno sequence through the "original" NdeI site, the stop site and the "original" BamHI site is as follows:

AAGGAGGAGATATACATA
ATGGGCCATCATCATCATCATCACGGTGGTCATATGTCC CTT (SEQ ID NO:8) [ORF] AAGGGGGATCC TAAACTGCAGAGATCC (SEQ ID NO:1). The Aurora kinase expressed using this vector has 14 amino acids added to the N-terminal end (MetGlyHisHisHisHisHisHisGlyGlyHisMetSerLeu (SEQ ID NO:10)) and four amino acids added to the C-terminal end (GluGlyGlySer (SEQ ID NO:11).

The phosphatase co-expression plasmid was then created by inserting the phosphatase gene from lambda bacteriophage into the above plasmid (Matsui T, et al., Biochem. Biophys. Res. Commun., 2001, 284:798-807). The phosphatase gene was amplified using PCR from template lambda bacteriophage DNA (HinDIII digest, New England Biolabs) using the following oligonucleotide primers:

```
                                          (SEQ ID NO:12)
Forward primer (PPfor):
GCAGAGATCCGAATTCGAGCTC
CGTCGACGGATGGAGTGAAAGAGATGCGC
```

-continued

Reverse primer (PPrev): (SEQ ID NO:13)
GGTGGTGGTGCTCGAGTGCGGCCGCAA
GCTTTCATCATGCGCCTTCTCCCTGTAC The PCR product (744 base pairs expected) was gel purified. The purified DNA and non-co-expression plasmid DNA were then digested with SacI and XhoI restriction enzymes. Both the digested plasmid and PCR product were then gel purified and ligated together for 8 hrs at 16° C. with T4 DNA ligase and transformed into Top 10 cells using standard procedures. The presence of the phosphatase gene in the co-expression plasmid was confirmed by sequencing. For standard molecular biology protocols followed here, see also, for example, the techniques described in Sambrook et al., Molecular Cloning: A Laboratory Manual, Cold Spring Harbor Laboratory, NY, 2001, and Ausubel et al., Current Protocols in Molecular Biology, Greene Publishing Associates and Wiley Interscience, NY, 1989.

The co-expression plasmid contains both the Aurora kinase and lambda phosphatase genes under control of the lac promoter, each with its own ribosome binding site. By cloning the phosphatase into the middle of the multiple cloning site, downstream of the target gene, convenient restriction sites are available for subcloning the phosphatase into other plasmids. These sites include SacI, SalI and EcoRI between the kinase and phosphatase and HinDIII, NotI and XhoI downstream of the phosphatase.

Protein Kinase Expression

An open-reading frame for c-Abl was amplified from a *Mus musculus* (mouse) cDNA library prepared from freshly harvested mouse liver using a commercially available kit (Invitrogen) by PCR using the following primers:

Forward primer: GACAAGTGGGAAATGGAGC (SEQ ID NO:14)

Reverse primer: CGCCTCGTTTCCCCAGCTC (SEQ ID NO:15)

The PCR product (846 base pairs expected) was purified from the PCR reaction mixture using a PCR cleanup kit (Qiagen). The purified DNA was ligated for 5 minutes at room temperature with topoisomerase into pSGX3-TOPO. The vector pSGX3-TOPO is a topoisomerase-activated, modified version of pET26b (Novagen, Madison, Wis.) wherein the following sequence has been inserted into the NdeI site: CATATGTCCCTT (SEQ ID NO:16) and the following sequence inserted into the BamHI site: AAGGGCATCATCACCATCACCACTGATCC (SEQ ID NO:17). The sequence of the resulting plasmid, from the Shine-Dalgarno sequence through the stop site and the BamHI, site is as follows: AAGGAGGA GATATACATATGTC CCTT (SEQ ID NO:18) [ORF]AAGGGC ATCAT CACCATCACCAC TGATCC (SEQ ID NO:19). The c-Abl expressed using this vector had three amino acids added to its N-terminal end (Met Ser Leu) and 8 amino acids added to its C-terminal end (GluGlyHisHisHisHisHisHis (SEQ ID NO:20).

A c-Abl/phosphatase co expression plasmid was then created by subcloning the phosphatase from the Aurora co-expression plasmid of Example 1 into the above plasmid. Both the Aurora co-expression plasmid and the Abl non-co-expression plasmid were digested 3 hrs with restriction enzymes EcoRI and NotI. The DNA fragments were gel purified and the phosphatase gene from the Aurora plasmid was ligated with the digested c-Abl plasmid for 8 hrs at 16° C. and transformed into Top 10 cells. The presence of the phosphatase gene in the resulting construct was confirmed by restriction digestion analysis.

This plasmid codes for c-Abl and lambda phosphatase co expression. It has the additional advantage of two unique restriction sites, XbaI and NdeI, upstream of the target gene that can be used for subcloning of other target proteins into this phosphatase co-expressing plasmid.

The plasmid for Abl T315I was prepared by modifying the Abl plasmid using the Quick Change mutagenesis kit (Stratagene) with the manufacturer's suggested procedure and the following oligonucleotides:

Mm05582dS4 (SEQ ID NO:21)
5'-CCACCATTCTACATAATCATTGAGTTCATGACCTATGGG-3'

Mm05582dA4 (SEQ ID NO:22)
5'-CCCATAGGTCATGAACTCAATGATTATGTAGAATGGTGG-3'

Protein from the phosphatase co-expression plasmids was purified as follows. The non-co-expression plasmid was transformed into chemically competent BL21(DE3)Codon+ RIL (Stratagene) cells and the co-expression plasmid was transformed into BL21(DE3) pSA0145 (a strain that expresses the lytic genes of lambda phage and lyses upon freezing and thawing (Crabtree S, Cronan J E Jr. J Bacteriol 1984 Apr;158(1):354-6)) and plated onto petri dishes containing LB agar with kanamycin. Isolated, single colonies were grown to mid-log phase and stored at −80° C. in LB containing 15% glycerol. This glycerol stock was streaked on LB agar plates with kanamycin and a single colony was used to inoculate 10 ml cultures of LB with kanamycin and chloramphenicol, which was incubated at 30° C. overnight with shaking. This culture was used to inoculate a 2L flask containing 500 mls of LB with kanamycin and chloramphenicol, which was grown to mid-log phase at 37° C. and induced by the addition of IPTG to 0.5 mM final concentration. After induction flasks were incubated at 21° C. for 18 hrs with shaking.

The c-Abl T315I KD was purified as follows. Cells were collected by centrifugation, lysed in diluted cracking buffer (50 mM Tris HCl, pH 7.5, 500 mM KCk, 0.1% Tween 20, 20 mM Imidazole, with sonication, and centrifuged to remove cell debris. The soluble fraction was purified over an IMAC column charged with nickel (Pharmacia, Uppsala, Sweden), and eluted under native conditions with a gradient of 20 mM to 500 mM imidazole in 50 mM Tris, pH7.8, 500 mM NaCl, 10 mM methionine, 10% glycerol. The protein was then further purified by gel filtration using a Superdex 75 preparative grade column equilibrated in GF5 buffer (10 mM HEPES, pH7.5, 10 mM methionine, 500 mM NaCl, 5 mM DTT, and 10% glycerol). Fractions containing the purified c-Abl T315I KD kinase domain were pooled. The protein obtained was 98% pure as judged by electrophoresis on SDS polyacrylamide gels. Mass spectroscopic analysis of the purified protein showed that it was predominantly singly phosphorylated. The protein was then dephosphorylated with Shrimp Alkaline Phosphotosase (MBI Fermentas, Burlington, Canada) under the following conditions: 100 U Shrimp Alkaline Phosphatase/mg of c-Abl T315I KD, 100 mM $MgCl_2$, and 250 mM additional NaCl. The reaction was run overnight at 23° C. The protein was determined to be unphosphorylated by Mass spectroscopic analysis. Any precipitate was spun out and the soluble fraction was separated from reactants by gel filtration using a Superdex 75 preparative grade column equilibrated in GF4 buffer (10 mM HEPES, pH7.5, 10 mM methionine, 150 mM NaCl, 5 mM DTT, and 10% glycerol).

Example 4

Cell Assays

Flt3 cell line selection was performed according to the following two known methodologies: Kelly, et al, *Cancer Cell* 1:421-32 (2002); and Ye, et al, *Blood* 100: 2941-2949 (2002). MV4-11 and THP cells are maintained in Iscove's Modified Dulbecco's Medium supplemented with 10% fetal bovine serum (FBS) and penicillin/streptomycin, Ba/F3 cells are maintained in RPMI 1640 supplemented with 10% FBS, penicillin/streptomycin and 5ng/ml recombinant mouse IL-3.

Cell Survival Assays

Compounds were tested in both of the following assays in triplicates.

96-well XTT assay: Cells are grown in their growth media containing various concentrations of compounds (triplicates) on a 96-well plate for 72 hours at 37° C. The starting cell number is 8000 cells per well and volume is 120 µl. At the end of the 72-hour incubation, 40µl of XTT labeling mixture (50:1 solution of sodium 3'-[1 -(pheylamino-carbonyl)-3,4-tetrazolium]-bis (4-methoxy-6-nitro)benzene sulfonic acid hydrate and Electron-coupling reagent: PMS (N-methyl dibenzopyrazine methyl sulfate) is added to each well of the plate. After additional 2 hours of incubation at 37° C., the absorbance reading at 405 nm with background correction at 650 nm is done using a spectrophotometer.

384-well AlamarBlue assay: 90 µl of cell suspension is plated onto each well of a 384-well plate preprinted with 0.5 µl of compound in DMSO or DMSO only. The starting cell number is 4000 cells per well. After 72-hour incubation, 10 µl of AlamarBlue solution (440 µM resazurin in PBS) is then added to each well of the plate. After additional 2-hour incubation at 37° C., fluorescence is measured using a TECAN plate reading with excitation at 535 nm and emission 591 nm.

Results are shown in Table 10 below.

TABLE 10

| Structure | MV4-11 (THP) IC$_{50}$ |
|---|---|
| (structure) | B (C) |
| (structure) | B (C) |

TABLE 10-continued

| Structure | MV4-11 (THP) IC$_{50}$ |
|---|---|
| (structure) | B (C) |
| (structure) | B (C) |

In Table 10, A is <1 µM, B is 1-10 µM, and C is 11-100 µM.

Cellular Scratch Assay

Table 11 show the reagents that were used in the present cellular scratch assay.

TABLE 11

| DESCRIPTION | VENDOR | CATALOG # | UNIT SIZE | UNIT PRICE |
|---|---|---|---|---|
| Assay Media | | | | |
| Opti-MEM | Invitrogen | 11058-021 | 500 ml | $24.20 |
| NEAA, | Invitrogen | 11140-050 | 100 ml | $12.20 |
| 1% Pen-Strep | Invitrogen | 15140-122 | 100 ml | $14.85 |
| Sodium pyruvate | Invitrogen | 11360-070 | 100 ml | $6.60 |
| Crystal Violet | Sigma | C3886 | 25 g | $18.30 |
| Accustain Formalin solution, 10% | Sigma | | | |
| PBS | | | | |
| HGF 30 ng/ul in H$_2$O | Chemicon | GF116 | | $195 |

MDCK, A549, A431, T24, H441 and SW579 cell lines were plated onto six-well trays in triplicate for, +/− HGF and +/− compound, at densities that would give confluent monolayers after 24 hours. Confluent monolayers were incubated a further 48 hours to allow intercellular junctions to mature before being serum-starved for 24 hours. A linear wound was generated on the monolayers by scraping with the tip of at 200 µl pipette tip.

Unattached cells were washed off with PBS and assay media (Opti-MEM with 1% Sodium Pyruvate, 1% Pen/Strep, 1% NEAA, +/− hepatocyte growth factor ("HGF") at 90 ng/ml and +/− compound). After 24 hours, HGF was added to cells in the presence or absence of test compound. Cells were washed 1× with PBS then cells were fixed and stained with 10% formalin and 0.2% crystal violet in PBS for 10 minutes at room temperature. The wells are then washed 5× with PBS adding 1 ml of PBS to each well, and photographed. Photographs were inspected to determine whether the test compound successfully reduced cell growth within the linear wound area.

The following compounds were shown to exhibit inhibitory poperties in the Cellular Scratch assay:

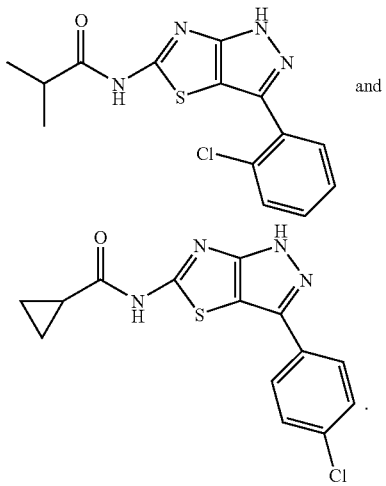

c-Met Phospho-ELISA Assay

Table 12 shows the reagents that were used in the present c-Met phosphor-ELISA assay.

Cells were plated at 3×10⁵ cell/ml in a total volume of 10 ml (3×10⁶ total) and plated in a 100 mm dish in duplicate and incubated overnight at 37° C. with 5% $CO_2$. The day before the assay, the cells were washed 1× with PBS and 10 mls of assay media (Opti-MEM I, reduced serum media with 1% NEAA, 1% Sodium Pyruvate, 1% Pen/Strep) was added to each plate of cells.

To appropriate wells of the plate was added 90 ng/ml of HGF followed by a 10 minute incubation at 37° C. under 5% $CO_2$. At the end of the 10 minute incubation, lysis buffer was added to each well on the plate to give a final cell density of 2×10e4 per µl on ice. Cells were scraped with cell scraper, pipetted into an eppendorf tube, and incubated on ice for 15 minutes. Cells were centrifuged at 14,000 g for 5 minutes. 150 µl of lysate was pipetted into the wells on plate for serial dilution across the rows of the plate. To make the ELISA plate, commercially available rabbit Anti-Met antibodies were prepared at a concentration of 0.125 µg/ml α-c-Met Ab in coating buffer (0.1M Na-carbonate, pH 9.5), and plated at 10 ml per plate (12.5 µl 100 µg/ml Ab/10 ml). In a high binding multi-well plate, 100 l Ab in coating buffer was added in each well, and each plate was covered with plate sealer and incubated overnight at 4° C.

Excess antibody was removed and the ELISA plate was washed 4× with 200 µl of wash buffer (0.05% Tween in PBS,

TABLE 12

| DESCRIPTION | VENDOR | CATALOG # | UNIT SIZE |
|---|---|---|---|
| Assay Media | | | |
| Opti-MEM | Invitrogen | | 500 ml |
| NEAA, | Invitrogen | 11140-050 | 100 ml |
| 1% Pen-Strep | Invitrogen | 15140-122 | 100 ml |
| Sodium pyruvate | Invitrogen | 11360-070 | 100 ml |
| α-c-Met antibody | Assay Design | 905-076 | 100 µg |
| 96w High binding | Matrix Technologies | 4927 | 1 case |
| Plate seals | | | |
| lysis buffer components | | | |
| Tris-Cl pH7.4 (1 M) | | | |
| NP-40 (10%) | | | |
| EDTA (500 mM) | | | |
| NaPP (100 mM) | | | |
| NaF (500 mM) | | | |
| NaCl (5 M) | | | |
| Protease inhibitor, compete | Sigma | | |
| PMSF (100 mM in isopropanol) | | | |
| NaVO₄ (100 mM)* | | | |
| PBS, ice cold | | | |
| HGF 30 ng/ul in H₂O | Chemicon | GF116 | |
| α-phosphotyrosine (4G10) mention quote#2912 in the notes to get special pricing | Upstate cell signaling solutions | 05-321 | 200 µg |
| Goat α-Rabbit HRP | Jackson Immunoresearch | 115-035-003 | |
| BD OptEIA Reagent Set B | BD Biosciences | 550534 | 1 |
| coating buffer (0.1 M Na-carbonate, pH 9.5) | | | 250 ml |
| Assay Diluent | | | 1000 ml |
| Wash buffer (.05% Tween/PBS) | | | 1000 ml (20×) |
| SuperSignal ELISA Pico Chemiluminescent Substrate | Pierce | 37070 | | pH 7.4). 150 µl of lysate was added per well and serially diluted across the rows of the plate. Plates were sealed and incubated 2 hours at room temperature. The detection antibody (α-p-Y 4G10, Upstate) was prepared in assay diluent. The antibody was diluted 1:1000 (stock=2 µg/µl, 200 µg in 100 µl; f.c.=2 µg/ml) in assay diluent and 10 ml of diluted antibody per plate was added. The lysate was removed from the ELISA plates, and wells washed with 200 µl per well wash buffer 4×. 100 µl of detection antibody was added to each well, covered, and incubated 1 hr at room temperature. Excess detection antibody was removed from the ELISA plates, and the wells washed with 200 µl per well with wash buffer 4×.

Secondary antibody, goat anti-rabbit HRP, was diluted 1:3000 in assay diluent (3.33 µl per 10 mls diluent) and added at 10 ml of diluted antibody per plate. Excess secondary antibody was removed from the ELISA plate, the plate was washed with 200 µl per well of wash buffer 4×.

Substrate Reagent A and Substrate Reagent B (Cat#37070 SuperSignal ELISA Pico Chemiluminescent Substrate from Pierce) were added immediately before use (10 ml resultant solution per plate). 100 µl substrate per well was added, mixed for 1 minute and visualized with a luminometer.

What is claimed is:

1. A compound having the formula:

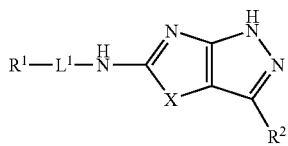

wherein

X is —S—, $L^1$ is —C(Z)-, or —SO$_2$—, wherein Z is =O, =S, or =NR$^{11}$, wherein R$^{11}$ is hydrogen, —OH, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^1$ is hydrogen, —$CF_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, —$OR^{12}$, or —$NR^{13}R^{14}$, wherein $R^{12}$ is selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, $R^{13}$ and $R^{14}$ are independently selected from substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^{13}$ and $R^{14}$ are optionally joined to from a ring with the nitrogen to which they are attached, wherein said ring is substituted or unsubstituted cycloalkyl, substituted or unsubstituted heterocycloalkyl, substituted or unsubstituted aryl, or substituted or unsubstituted heteroaryl;

$R^2$ is substituted or unsubstituted alky substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^2$ is attached to the remainder of the molecule via a carbon atom to form a carbon-carbon bond, and wherein if $R^2$ is unsubstituted phenyl, X is S, $L^1$ is —C(Z)-, and Z is =O, then $R^1$ is not unsubstituted phenyl, or a pharmaceutically acceptable salt thereof.

2. The compound of claim 1, wherein
X is —S—; and
$L^1$ is —C(Z)-, wherein Z is =O.

3. The compound of claim 1, wherein
$R^2$ is substituted or unsubstituted $C_1$-$C_{20}$ alkyl, substituted or unsubstituted 2 to 20 membered heteroalkyl, substituted or unsubstituted $C_3$-$C_8$ cycloalkyl, substituted or unsubstituted 3 to 8 membered heterocycloalkyl, substituted or unsubstituted aryl, or substituted or unsubstituted heteroaryl.

4. The compound of claim 1, wherein
$R^2$ is substituted or unsubstituted $C_1$-$C_{10}$ alkyl, substituted or unsubstituted 2 to 10 membered heteroalkyl, substituted or unsubstituted $C_3$-$C_7$ cycloalkyl, or unsubstituted 3 to 7 membered heterocycloalkyl, substituted or unsubstituted aryl, or substituted or unsubstituted heteroaryl.

5. The compound of claim 1, wherein $R^2$ is
(1) unsubstituted $C_1$-$C_{10}$ alkyl;
(2) unsubstituted 2 to 10 membered heteroalkyl;
(3) unsubstituted $C_3$-$C_7$ cycloalkyl;
(4) unsubstituted 3 to 7 membered heterocycloalkyl;
(5) unsubstituted aryl;
(6) unsubstituted heteroaryl;
(7) substituted $C_1$-$C_{10}$ alkyl;
(8) substituted 2 to 10 membered heteroalkyl;
(9) substituted $C_3$-$C_7$ cycloalkyl;
(10) substituted 3 to 7 membered heterocycloalkyl;
(11) substituted aryl; or
(12) substituted heteroaryl;
wherein
(7), (8), (9), or (10) is substituted with an oxo, —OH, —$CF_3$, —COOH, halogen, $R^{21}$-substituted or unsubstituted $C_1$-$C_{10}$ alkyl, $R^{21}$-substituted or unsubstituted 2 to 10 membered heteroalkyl, $R^{21}$-substituted or unsubstituted $C_3$-$C_7$ cycloalkyl, $R^{21}$-substituted or unsubstituted 3 to 7 membered heterocycloalkyl, $R^{22}$-substituted or unsubstituted aryl, or $R^{22}$-substituted or unsubstituted heteroaryl, -$L^{22}$-C(O)$R^3$, -$L^{22}$-$OR^4$, -$L^{22}$-$NR^4R^5$, $OR^4$, or -$L^{22}$-S(O)$_m$$R^6$,

(11) or (12) is substituted with an —OH, —$CF_3$, —COOH, halogen, $R^{21}$-substituted or unsubstituted $C_1$-$C_{10}$ alkyl, $R^{21}$-substituted or unsubstituted 2 to 10 membered heteroalkyl, $R^{21}$-substituted or unsubstituted $C_3$-$C_7$ cycloalkyl, $R^{21}$-substituted or unsubstituted 3 to 7 membered heterocycloalkyl, $R^{22}$-substituted or unsubstituted aryl, $R^{22}$-substituted or unsubstituted heteroaryl, -$L^{22}$-C(O)$R^3$, -$L^{22}$-$OR^4$, -$L^{22}$-$NR^4R^5$, or -$L^{22}$-S(O)$_m$$R^6$, $R^3$ is hydrogen, $R^{21}$-substituted or unsubstituted $C_1$-$C_{10}$ alkyl, $R^{21}$-substituted or unsubstituted 2 to 10 membered heteroalkyl, $R^{21}$-substituted or unsubstituted $C_3$-$C_7$ cycloalkyl, $R^{21}$-substituted or unsubstituted 3 to 7 membered heterocycloalkyl, $R^{22}$-substituted or unsubstituted aryl, $R^{22}$-substituted or unsubstituted heteroaryl, —$OR^{31}$, or —$NR^{32}R^{33}$, wherein $R^{31}$, $R^{32}$, and $R^{33}$ are independently hydrogen, $R^{21}$-substituted or unsubstituted $C_1$-$C_{10}$ alkyl, $R^{21}$-substituted or unsubstituted 2 to 10 membered heteroalkyl, $R^{21}$-substituted or unsubstituted $C_3$-$C_7$ cycloalkyl, $R^{21}$-substituted or unsubstituted 3 to 7 membered heterocycloalkyl, $R^{22}$-substituted or unsubstituted aryl, or unsubstituted heteroaryl, $R^4$ and $R^5$ are independently hydrogen, —$CF_3$, $R^{21}$-substituted or unsubstituted $C_1$-$C_{10}$ alkyl, $R^{21}$-substituted or unsubstituted 2 to 10 membered heteroalkyl, $R^{21}$-substituted or unsubstituted $C_3$-$C_7$ cycloalkyl, $R^{21}$-substituted or unsubstituted 3 to 7 membered heterocycloalkyl, $R^{22}$-substituted or unsubstituted aryl, $R^{22}$-substituted or unsubstituted heteroaryl, or —C(O)$R^{41}$, wherein $R^{41}$ is hydrogen, $R^{21}$-substituted or unsubstituted $C_1$-$C_{10}$ alkyl, $R^{21}$-substituted or unsubstituted 2 to 10 membered heteroalkyl, $R^{21}$-substituted or unsubstituted $C_3$-$C_7$ cycloalkyl, $R^{21}$-substituted or unsubstituted 3 to 7 membered heterocycloalkyl, $R^{22}$-substituted or unsubstituted aryl, or $R^{22}$-substituted or unsubstituted heteroaryl, $R^6$ is hydrogen, $R^{21}$-substituted or unsubstituted $C_1$-$C_{10}$ alkyl, $R^{21}$-substituted or unsubstituted 2 to 10 membered heteroalkyl, $R^{21}$-substituted or unsubstituted $C_3$-$C_7$ cycloalkyl, $R^{21}$-substituted or unsubstituted 3 to 7 membered heterocycloalkyl, $R^{22}$-substituted or unsubstituted aryl, or $R^{22}$-substituted or unsubstituted heteroaryl, $L^{22}$ is a bond, unsubstituted $C_1$-$C_{10}$ alkylene or unsubstituted heteroalkylene, m is 0, 1, or 2, $R^{21}$ is oxo, —OH, —COOH, —$CF_3$, amino, halogen, $R^{23}$-substituted or unsubstituted 2 to 10 membered heteroalkyl, $R^{23}$-substituted or unsubstituted $C_3$-$C_7$ cycloalkyl, $R^{23}$-substituted or unsubstituted 3 to 7 membered heterocycloalkyl, $R^{24}$-substituted or unsubstituted aryl, or $R^{24}$-substituted or unsubstituted heteroaryl, $R^{22}$ is —OH, —COOH, amino, halogen, —$CF_3$, $R^{23}$-substituted or unsubstituted 2 to 10 membered heteroalkyl, $R^{23}$-substituted or unsubstituted $C_3$-$C_7$ cycloalkyl, $R^{23}$-substituted or unsubstituted 3 to 7 membered heterocycloalkyl, $R^{24}$-substituted or unsubstituted aryl, or $R^{24}$-substituted or unsubstituted heteroaryl, $R^{23}$ is oxo, —OH, —COOH, amino, halogen, —$CF_3$, unsubstituted $C_1$-$C_{10}$ alkyl, unsubstituted 2 to 10 membered heteroalkyl, unsubstituted $C_3$-$C_7$ cycloalkyl, unsubstituted 3 to 7 membered heterocycloalkyl, unsubstituted aryl, unsubstituted heteroaryl, and $R^{24}$ is —OH, —COOH, amino, halogen, —$CF_3$, unsubstituted $C_1$-$C_{10}$ alkyl, unsubstituted 2 to 10 membered heteroalkyl, unsubstituted $C_3$-$C_7$ cycloalkyl, unsubstituted 3 to 7 membered heterocycloalkyl, unsubstituted aryl, unsubstituted heteroaryl.

6. The compound of claim 5, wherein if $R^{21}$ or $R^{22}$ is substituted or unsubstituted heterocycloalkyl, the heterocycloalkyl is hydantoinyl, dioxolanyl, dioxanyl, trioxanyl, tetrahydrothienyl, tetrahydrofuranyl, tetrahydrothiophenyl, tetrahydropyranyl, tetrahydrothiopyranyl, pyrrolidinyl, morpholino, piperidinyl, or piperazinyl.

7. The compound of claim 5, wherein if $R^{21}$ or $R^{22}$ is substituted or unsubstituted heteroaryl, then the heteroaryl is pyrazolyl, furanyl, imidazolyl, isoxazolyl, oxadiazolyl, oxazolyl, pyrrolyl, pyridyl, pyrazyl, pyrimidyl, pyridazinyl, thiazolyl, isothioazolyl, triazolyl, thienyl, triazinyl, or thiadiazolyl.

8. The compound of claim 5, wherein $R^2$ is substituted or unsubstituted aryl, or substituted or unsubstituted heteroaryl.

9. The compound of claim 5, wherein $R^2$ is substituted or unsubstituted cycloalkyl, substituted or unsubstituted heterocycloalkyl, substituted or unsubstituted alkyl, or substituted or unsubstituted heteroalkyl.

10. The compound of claim 8, wherein the $R^2$ is substituted with a(n)

(1) unsubstituted $C_1$-$C_{10}$ alkyl,
(2) unsubstituted 2 to 10 membered heteroalkyl,
(3) unsubstituted $C_3$-$C_7$ cycloalkyl,
(4) unsubstituted 3 to 7 membered heterocycloalkyl,
(5) unsubstituted aryl,
(6) unsubstituted heteroaryl,
(7) halogen,
(8) —OH,
(9) amino,
(10) —$CF_3$,
(11) 3 to 7 membered heterocycloalkyl substituted with unsubstituted $C_1$—$C_{10}$ alkyl, or
(12) $C_1$-$C_{10}$ alkyl substituted with an unsubstituted aryl.

11. The compound of claim 8, wherein the $R^2$ is substituted with a (1) halogen
(2) -$L^{22}$-C(O)$R^3$
(3) -$L^{22}$-O$R^4$,
(4) -$L^{22}$-NR$^4$R$^5$, or
(5) -$L^{22}$-S(O)$_m$R$^6$.

12. The compound of claim 8, wherein the $R^2$ substituent is (1) -$L^{22}$-C(O)$R^3$, wherein
$R^3$ is hydrogen, unsubstituted $C_1$-$C_{10}$ alkyl, —OR$^{31}$, —NR$^{32}$R$^{33}$, wherein
$R^{31}$, $R^{32}$, and $R^{33}$ are independently hydrogen, unsubstituted $C_1$-$C_{10}$ alkyl, or unsubstituted $C_3$-$C_7$ cycloalkyl, and
$L^{22}$ is unsubstituted $C_1$-$C_{10}$ alkylene, (2) -$L^{22}$-OR$^4$, wherein
$R^4$ is hydrogen, —$CF_3$, —$CHF_2$, unsubstituted $C_1$-$C_{10}$ alkyl, unsubstituted $C_3$-$C_7$ cycloalkyl, unsubstituted $C_1$-$C_{10}$ cycloalkylalkyl, or —C(O)R$^{41}$, wherein
$R^{41}$ is hydrogen, or unsubstituted $C_1$-$C_{10}$ alkyl, (3) -$L^{22}$-NR$^4$R$^5$, wherein
$R^4$ and $R^5$ are independently hydrogen, unsubstituted $C_1$-$C_{10}$ alkyl, or —C(O)R$^{41}$, wherein
$R^{41}$ is independently hydrogen, or unsubstituted $C_1$-$C_{10}$ alkyl, or (4) $L^{22}$-S(O)$_m$—R$^6$, wherein
$R^7$ is hydrogen or unsubstituted $C_1$-$C_{10}$ alkyl.

13. The compound of claim 5, wherein if $R^2$ is substituted or unsubstituted aryl, then the aryl is phenyl, benz[cd]indol-2(1H)-one-yl, oxindolyl, indazolinonyl, benzoimidazolyl, indolyl, benzodioxanyl, coumarinyl, chromonyl, benzopyrazyl, naphthyl, quinolyl, or isoquinolyl;

if $R^2$ is substituted or unsubstituted heteroaryl, then the heteroaryl is pyrazolyl, furanyl, imidazolyl, isoxazolyl, oxadiazolyl, oxazolyl, pyrrolyl, pyridyl, pyrimidyl, pyrazyl, pyridazinyl, thiazolyl, isothioazolyl, triazolyl, thienyl, triazinyl, thiadiazolyl, or if $R^2$ is substituted or unsubstituted heterocycloalkyl, then the heterocycloalkyl is hydantoinyl, dioxolanyl, dioxanyl, trioxanyl, tetrahydrothienyl, tetrahydrofuranyl, tetrahydrothiophenyl, tetrahydropyranyl, tetrahydrothiopyranyl, pyrrolidinyl, morpholino, piperidinyl, or piperazinyl.

14. The compound of claim 5, wherein if (11) or (12) is substituted with a $R^{21}$-substituted or unsubstituted 3 to 7 membered heterocycloalkyl, then the heterocycloalkyl is dioxolanyl, dioxanyl, trioxanyl, tetrahydrofuranyl, tetrahydrothiophenyl, tetrahydropyranyl, tetrahydrothiopyranyl, pyrrolidinyl, morpholino, piperidinyl, or piperazinyl; or if (11) or (12) is substituted with a $R^{22}$-substituted or unsubstituted heteroaryl, then the heteroaryl is pyrazolyl, furanyl, imidazolyl, isoxazolyl, oxadiazolyl, oxazolyl, pyrrolyl, pyridyl, pyrazyl, pyrimidyl, pyridazinyl, thiazolyl, isothioazolyl, triazolyl, or thienyl, triazinyl, or thiadiazolyl.

15. The compound of claim 1, wherein $R^1$ is hydrogen, substituted or unsubstituted $C_1$-$C_{10}$ alkyl, substituted or unsubstituted 2 to 10 membered heteroalkyl, substituted or unsubstituted $C_3$-$C_7$ cycloalkyl, substituted or unsubstituted 3 to 7 membered heterocycloalkyl, substituted or unsubstituted aryl, or substituted or unsubstituted heteroaryl.

16. The compound of claim 1, wherein $R^1$ is (1) —$CF_3$;
(2) unsubstituted $C_1$-$C_{10}$ alkyl;
(3) unsubstituted 2 to 10 membered heteroalkyl;
(4) unsubstituted $C_3$-$C_7$ cycloalkyl;
(5) unsubstituted 3 to 7 membered heterocycloalkyl;
(6) unsubstituted aryl;
(7) unsubstituted heteroaryl;
(8) substituted $C_1$-$C_{10}$ alkyl;
(9) substituted 2 to 10 membered heteroalkyl;
(10) substituted $C_3$-$C_7$ cycloalkyl;
(11) substituted 3 to 7 membered heterocycloalkyl;
(12) substituted aryl; or
(13) substituted heteroaryl;

wherein (8), (9), (10) or (11) is substituted with an oxo, —OH, —$CF_3$, —COOH, halogen, $R^{15}$-substituted or unsubstituted $C_1$-$C_{10}$ alkyl, $R^{15}$-substituted or unsubstituted 2 to 10 membered heteroalkyl, $R^{15}$-substituted or unsubstituted $C_3$-$C_7$ cycloalkyl, $R^{15}$-substituted or unsubstituted 3 to 7 membered heterocycloalkyl, $R^{16}$-substituted or unsubstituted aryl, $R^{16}$-substituted or unsubstituted heteroaryl, -$L^{11}$-C(O)$R^{100}$, -$L^{11}$-OR$^{104}$, -$L^{11}$-NR$^{104}$R$^{105}$, or -$L^{11}$-S(O)$_q$—R$^{107}$,

(12) or (13) is substituted with an —OH, —$CF_3$, —COOH, halogen, $R^{15}$-substituted or unsubstituted $C_1$-$C_{10}$ alkyl, $R^{15}$-substituted or unsubstituted 2 to 10 membered heteroalkyl, $R^{15}$-substituted or unsubstituted $C_3$-$C_7$ cycloalkyl, $R^{15}$-substituted or unsubstituted 3 to 7 membered heterocycloalkyl, R1 6-substituted or unsubstituted aryl, $R^{16}$-substituted or unsubstituted heteroaryl, -$L^{11}$-C(O)$R^{100}$, -$L^{11}$-O$R^{104}$, -$L^{11}$-N$R^{104}R^{105}$, or -$L^{11}$-S(O)$_q$—$R^{107}$, $R^{100}$ is hydrogen, $R^{15}$-substituted or unsubstituted $C_1$-$C_{10}$ alkyl, $R^{15}$-substituted or unsubstituted 2 to 10 membered heteroalkyl, $R^{15}$-substituted or unsubstituted $C_3$-$C_7$ cycloalkyl, $R^{15}$-substituted or unsubstituted 3 to 7 membered heterocycloalkyl, $R^{16}$-substituted or unsubstituted aryl, $R^{16}$-substituted or unsubstituted heteroaryl, —O$R^{101}$, or —N$R^{102}R^{103}$, wherein $R^{101}$, $R^{102}$, and $R^{103}$ are independently hydrogen, $R^{15}$-substituted or unsubstituted $C_1$-$C_{10}$ alkyl, $R^{15}$-substituted or unsubstituted 2 to 10 membered heteroalkyl, $R^{15}$-substituted or unsubstituted $C_3$-$C_7$ cycloalkyl, $R^{15}$-substituted or unsubstituted 3 to 7 membered heterocycloalkyl, $R^{16}$-substituted or unsubstituted aryl, or $R^{16}$-substituted or unsubstituted heteroaryl, $R^{104}$ and $R^{105}$ are independently hydrogen, —$CF_3$, $R^{15}$-substituted or unsubstituted $C_1$-$C_{10}$ alkyl, $R^{15}$-substituted or unsubstituted 2 to 10 membered heteroalkyl, $R^{15}$-substituted or unsubstituted $C_3$-$C_7$ cycloalkyl, $R^{15}$-substituted or unsubstituted 3 to 7 membered heterocycloalkyl, $R^{16}$-substituted or unsubstituted aryl, $R^{16}$-substituted or unsubstituted heteroaryl, or —C(O)$R^{106}$, wherein $R^{106}$ is independently hydrogen, $R^{15}$-substituted or unsubstituted $C_1$-$C_{10}$ alkyl, $R^{15}$-substituted or unsubstituted 2 to 10 membered heteroalkyl, $R^{15}$-substituted or unsubstituted $C_3$-$C_7$ cycloalkyl, $R^{15}$-substituted or unsubstituted 3 to 7 membered heterocycloalkyl, $R^{16}$-substituted or unsubstituted aryl, or $R^{16}$-substituted or unsubstituted heteroaryl, $R^{107}$ is hydrogen, $R^{15}$-substituted or unsubstituted $C_1$-$C_{10}$ alkyl, $R^{15}$-substituted or unsubstituted 2 to 10 membered heteroalkyl, $R^{15}$-substituted or unsubstituted $C_3$-$C_7$ cycloalkyl, $R^{15}$-substituted or unsubstituted 3 to 7 membered heterocycloalkyl, $R^{16}$-substituted or unsubstituted aryl, or $R^{16}$-substituted or unsubstituted heteroaryl, $L^{11}$ is a bond, unsubstituted $C_1$-$C_{10}$ alkylene, or unsubstituted heteroalkylene, q is 0, 1,or2, $R^{15}$ is oxo, —OH, —COOH, —$CF_3$, halogen, $R^{17}$-substituted or unsubstituted $C_1$-$C_{10}$ alkyl, $R^{17}$-substituted or unsubstituted 2 to 10 membered heteroalkyl, $R^{17}$-substituted or unsubstituted $C_3$-$C_7$ cycloalkyl, $R^{17}$-substituted or unsubstituted 3 to 7 membered heterocycloalkyl, $R^{18}$-substituted or unsubstituted aryl, or $R^{18}$-substituted or unsubstituted heteroaryl, $R^{16}$ is —OH, —COOH, —$CF_3$, halogen, $R^{17}$-substituted or unsubstituted $C_1$-$C_{10}$ alkyl, $R^{17}$-substituted or unsubstituted 2 to 10 membered heteroalkyl, $R^{17}$-substituted or unsubstituted $C_3$-$C_7$ cycloalkyl, $R^{17}$-substituted or unsubstituted 3 to 7 membered heterocycloalkyl, $R^{18}$-substituted or unsubstituted aryl, or $R^{18}$-substituted or unsubstituted heteroaryl, $R^{17}$ is oxo, —OH, —COOH, —$CF_3$, halogen, unsubstituted $C_1$-$C_{10}$ alkyl, unsubstituted 2 to 10 membered heteroalkyl, unsubstituted $C_3$-$C_7$ cycloalkyl, unsubstituted 3 to 7 membered heterocycloalkyl, unsubstituted aryl, or unsubstituted heteroaryl, and $R^{18}$ is —OH, —COOH, —$CF_3$, halogen, unsubstituted $C_1$-$C_{10}$ alkyl, unsubstituted 2 to 10 membered heteroalkyl, unsubstituted $C_3$-$C_7$ cycloalkyl, unsubstituted 3 to 7 membered heterocycloalkyl, unsubstituted aryl, or unsubstituted heteroaryl.

17. The compound of claim 16, wherein
if $R^{15}$ or $R^{16}$ is substituted or unsubstituted heterocycloalkyl, the heterocycloalkyl is hydantoinyl, dioxolanyl, dioxanyl, trioxanyl, tetrahydrothienyl, tetrahydrofuranyl, tetrahydrothiophenyl, tetrahydropyranyl, tetrahydrothiopyranyl, pyrrolidinyl, morpholino, piperidinyl, or piperazinyl.

18. The compound of claim 16, wherein
if $R^{15}$ or $R^{16}$ is substituted or unsubstituted heteroaryl, the heteroaryl is pyrazolyl, furanyl, imidazolyl, isoxazolyl, oxadiazolyl, oxazolyl, pyrrolyl, pyridyl, pyrazyl, pyrimidyl, pyridazinyl, thiazolyl, isothioazolyl, triazolyl, or thienyl, triazinyl, or thiadiazolyl.

19. The compound of claim 16, wherein
$R^{15}$ is oxo, —OH, —COOH, —$CF_3$, halogen, unsubstituted $C_1$-$C_{10}$ alkyl, unsubstituted 2 to 10 membered heteroalkyl, unsubstituted $C_3$-$C_7$ cycloalkyl, unsubstituted 3 to 7 membered heterocycloalkyl, unsubstituted aryl, or unsubstituted heteroaryl, and $R^{16}$ is —OH, —COOH, —$CF_3$, halogen, unsubstituted $C_1$-$C_{10}$ alkyl, unsubstituted 2 to 10 membered heteroalkyl, unsubstituted $C_3$-$C_7$ cycloalkyl, unsubstituted 3 to 7 membered heterocycloalkyl, unsubstituted aryl, or unsubstituted heteroaryl.

20. The compound of claim 1, wherein $R^1$ is
(1) unsubstituted $C_1$-$C_{10}$ alkyl;
(2) unsubstituted 2 to 10 membered heteroalkyl;
(3) unsubstituted $C_3$-$C_7$ cycloalkyl;
(4) unsubstituted 3 to 7 membered heterocycloalkyl;
(5) substituted $C_1$-$C_{10}$ alkyl;
(6) substituted 2 to 10 membered heteroalkyl;
(7) substituted $C_3$-$C_7$ cycloalkyl;
(8) substituted 3 to 7 membered heterocycloalkyl;
(9) substituted phenyl; or
(10) substituted heteroaryl;

wherein (5), (6), (7), or (8) is substituted with an oxo, —OH, —$CF_3$, —COOH, halogen, $R^{15}$-substituted or unsubstituted $C_1$-$C_{10}$ alkyl, or $R^{15}$-substituted or unsubstituted 2 to 10 membered heteroalkyl, and wherein (9) or (10) is substituted with an —OH, —$CF_3$, —COOH, halogen, $R^{15}$-substituted or unsubstituted $C_1$-$C_{10}$ alkyl, or $R^{15}$-substituted or unsubstituted 2 to 10 membered heteroalkyl.

21. The compound of claim 20, wherein $R^{15}$ is oxo, —OH, —COOH, —$CF_3$, halogen, unsubstituted $C_1$-$C_{10}$ alkyl, or unsubstituted 2 to 10 membered heteroalkyl.

22. The compound of claim 1, wherein $R^1$ is
(1) unsubstituted $C_1$-$C_{10}$ alkyl,
(2) unsubstituted 2 to 10 membered heteroalkyl,
(3) unsubstituted $C_3$-$C_7$ cycloalkyl,
(4) unsubstituted 3 to 7 membered heterocycloalkyl;
(5) $C_1$-$C_{10}$ alkyl substituted with an oxo, —OH, —COOH, —$CF_3$, halogen, unsubstituted $C_1$-$C_{10}$ alkyl, unsubstituted 2 to 10 membered heteroalkyl, unsubstituted $C_3$-$C_7$ cycloalkyl, unsubstituted 3 to 7 membered heterocycloalkyl, unsubstituted aryl, or unsubstituted heteroaryl;
(6) 2 to 10 membered heteroalkyl substituted with an oxo, —OH, —$CF_3$, —COOH, halogen, unsubstituted $C_1$-$C_{10}$ alkyl, 2 to 10 membered heteroalkyl, unsubstituted $C_3$-$C_7$ cycloalkyl, unsubstituted 3 to 7 membered heterocycloalkyl, unsubstituted aryl, or unsubstituted heteroaryl;
(7) $C_3$-$C_7$ cycloalkyl substituted with —OH, —$CF_3$, —COOH, halogen, unsubstituted $C_1$-$C_{10}$ alkyl, or unsubstituted 2 to 10 membered heteroalkyl;

(8) 3 to 7 membered heterocycloalkyl substituted with —OH, —CF$_3$, —COOH, halogen, unsubstituted C$_1$-C$_{10}$ alkyl, or unsubstituted 2 to 10 membered heteroalkyl;

(9) phenyl substituted with —OH, —CF$_3$, —COOH, halogen, unsubstituted C$_1$-C$_{10}$ alkyl, or unsubstituted 2 to 10 membered heteroalkyl; or

(10) heteroaryl substituted with —OH, —CF$_3$, —COOH, halogen, unsubstituted C$_1$-C$_{10}$ alkyl, or unsubstituted 2 to 10 membered heteroalkyl.

23. The compound of claim 16, wherein if R$^1$ is a substituted or unsubstituted heteroaryl, the heteroaryl is pyrazolyl, furanyl, imidazolyl, isoxazolyl, oxadiazolyl, oxazolyl, pyrrolyl, pyridyl, pyrimidyl, pyrazyl, pyridazinyl, thiazolyl, isothioazolyl, triazolyl, thienyl, triazinyl, or thiadiazolyl.

24. The compound of claim 16, wherein if R$^1$ is a substituted or unsubstituted heterocycloalkyl, then the heterocycloalkyl is hydantoinyl, dioxolanyl, dioxanyl, trioxanyl, tetrahydrothienyl, tetrahydrofuranyl, tetrahydrothiophenyl, tetrahydropyranyl, tetrahydrothiopyranyl, pyrrolidinyl, morpholino, piperidinyl, or piperazinyl.

25. The compound of claim 16, wherein the R$^1$ is substituted with a (1) halogen
(2) -L$^{11}$-C(O)R$^{100}$,
(3) -L$^{11}$-OR$^{104}$,
(4) -L$^{11}$-NR$^{104}$R$^{105}$, or
(5) -L$^{11}$-S(O)$_q$R$^{107}$.

26. The compound of claim 25, wherein

R$^{15}$ is oxo, —OH, —COOH, —CF$_3$, halogen, unsubstituted C$_1$-C$_{10}$ alkyl, unsubstituted 2 to 10 membered heteroalkyl, unsubstituted C$_3$-C$_7$ cycloalkyl, unsubstituted 3 to 7 membered heterocycloalkyl, unsubstituted aryl, or unsubstituted heteroaryl, and R$^{16}$ is —OH, —COOH, —CF$_3$, halogen, unsubstituted C$_1$-C$_{10}$ alkyl, unsubstituted 2 to 10 membered heteroalkyl, unsubstituted C$_3$-C$_7$ cycloalkyl, unsubstituted 3 to 7 membered heterocycloalkyl, unsubstituted aryl, or unsubstituted heteroaryl.

27. A pharmaceutical composition comprising a compound of claim 1 in admixture with a pharmaceutically acceptable excipient.

* * * * *